(12) United States Patent
Zhang et al.

(10) Patent No.: US 9,675,494 B2
(45) Date of Patent: Jun. 13, 2017

(54) ELASTIC TONGUE-DORSUM RETRACTION DEVICE, CLAMPING PLIERS, INSTALLATION PLIERS, LINE GUIDE AND IMPLANTATION METHOD

(71) Applicants: Xiangmin Zhang, Guangzhou (CN); Xing Zhou, Guangzhou (CN)

(72) Inventors: Xiangmin Zhang, Guangzhou (CN); Xing Zhou, Guangzhou (CN)

(73) Assignee: GUANGZHOU T.K. MEDICAL INSTRUMENT CO., LTD., Guangzhou (CN)

( * ) Notice: Subject to any disclaimer, the term of this patent is extended or adjusted under 35 U.S.C. 154(b) by 0 days.

(21) Appl. No.: 14/384,367

(22) PCT Filed: Dec. 31, 2013

(86) PCT No.: PCT/CN2013/091266
§ 371 (c)(1),
(2) Date: Sep. 10, 2014

(87) PCT Pub. No.: WO2014/117631
PCT Pub. Date: Aug. 7, 2014

(65) Prior Publication Data
US 2015/0064651 A1 Mar. 5, 2015

(30) Foreign Application Priority Data

Feb. 4, 2013 (CN) .......................... 2013 1 0043949
Feb. 4, 2013 (CN) ..................... 2013 2 0063137 U
(Continued)

(51) Int. Cl.
*A61F 5/56* (2006.01)
*A61C 3/10* (2006.01)

(52) U.S. Cl.
CPC ................ *A61F 5/566* (2013.01); *A61C 3/10* (2013.01)

(58) Field of Classification Search
CPC ........... A61F 5/566; A61C 3/10; A61H 1/008; A61H 2205/026; A61H 2201/168; A61H 21/00
(Continued)

(56) References Cited

U.S. PATENT DOCUMENTS 5,052,409 A * 10/1991 Tepper .................... A61F 5/566
128/859
8,474,462 B2 * 7/2013 Makower ................ A61F 5/566
128/848
(Continued)

FOREIGN PATENT DOCUMENTS

CN        201271277 Y    7/2009
CN        101578080 A    11/2009
(Continued)

OTHER PUBLICATIONS

Zhang et al., Communication Pursuant to Rules 161(2) and 162-EPC, EP13873591.5, Sep. 11, 2015, 2 pgs.
(Continued)

*Primary Examiner* — Nicholas Lucchesi
(74) *Attorney, Agent, or Firm* — Morgan, Lewis & Bockius LLP

(57) ABSTRACT

The present invention relates to an elastic tongue-dorsum refraction device for treating obstructive sleep apnea/hypopnea syndrome (OSAHS), clamping pliers, installation pliers, a line guide, and an implantation method. The elastic tongue-dorsum refraction device of the present invention includes a tongue dorsum connection mechanism, an elastic retractor and a tooth-side fastener. The tongue dorsum connection mechanism is disposed at the tongue dorsum portion, the tooth-side fastener is fixed to teeth or the alveolar bone or outside the maxilla and mandible lips, one end of the elastic retractor is connected to the tooth-side fastener, and the other end of the elastic retractor is con-
(Continued)

nected to the tongue dorsum connection mechanism. In this way, an elastic retraction device using the tooth-side fastener as a fulcrum is formed. By pulling up the sagging tongue root forward, stenosis and obstruction of the airway at the glossopharyngeal portion are prevented, thereby providing a function of treating snoring and OSAHS. Since the elastic refractor exerts an elastic retraction force on the tongue dorsum portion, the movement of the tongue tip is not affected when the tongue root is properly pulled up, so that a clear language function and an adequate swallowing function can be maintained, and not only the airway at the glossopharyngeal portion is enlarged, but also good comfort is provided. In addition, the present invention further discloses clamping pliers, installation pliers and a line guide for use together with the elastic tongue-dorsum retraction device, and an implantation method of the elastic tongue-dorsum retraction device.

16 Claims, 49 Drawing Sheets

(30) Foreign Application Priority Data

| Sep. 16, 2013 | (CN) | 2013 1 0423258 |
|---|---|---|
| Sep. 16, 2013 | (CN) | 2013 1 0423312 |
| Sep. 16, 2013 | (CN) | 2013 1 0423315 |
| Sep. 16, 2013 | (CN) | 2013 1 0423351 |
| Sep. 16, 2013 | (CN) | 2013 1 0423353 |
| Sep. 16, 2013 | (CN) | 2013 1 0423355 |
| Sep. 16, 2013 | (CN) | 2013 1 0423417 |
| Dec. 26, 2013 | (CN) | 2013 1 0733988 |
| Dec. 27, 2013 | (CN) | 2013 1 0738009 |

(58) Field of Classification Search
USPC .......... 433/7, 18, 19, 21, 140, 159; 128/848, 128/857, 860
See application file for complete search history.

(56) References Cited

U.S. PATENT DOCUMENTS

| 8,656,920 | B1* | 2/2014 | Tannatt | A61F 5/566 128/848 |
|---|---|---|---|---|
| 8,875,713 | B2* | 11/2014 | Metz | A61F 5/566 128/848 |
| 8,882,499 | B2* | 11/2014 | White | A61C 7/00 433/18 |
| 9,204,991 | B1* | 12/2015 | Harkins | A61C 7/08 |
| 9,226,866 | B2* | 1/2016 | Haseley | A61H 1/008 |
| 2003/0031980 | A1* | 2/2003 | Owais | A61C 5/122 433/136 |
| 2005/0287495 | A1* | 12/2005 | Longley | A61F 5/0006 433/140 |
| 2007/0163603 | A1 | 7/2007 | Sikora | |
| 2007/0231766 | A1* | 10/2007 | Cope | A61C 7/10 433/7 |
| 2007/0261701 | A1 | 11/2007 | Sanders | |
| 2007/0289600 | A1 | 12/2007 | Li | |
| 2008/0053461 | A1 | 3/2008 | Hirotsuka et al. | |
| 2008/0058584 | A1 | 3/2008 | Hirotsuka et al. | |
| 2008/0066769 | A1 | 3/2008 | Dineen et al. | |
| 2008/0108008 | A1* | 5/2008 | Chung | A61C 7/00 433/24 |
| 2010/0015565 | A1* | 1/2010 | Carrillo Gonzalez | A61C 5/00 433/7 |
| 2015/0140506 | A1* | 5/2015 | Motamedi | A61C 5/14 433/31 |

FOREIGN PATENT DOCUMENTS

| CN | 102198010 A | 9/2011 |
|---|---|---|
| WO | WO2009/096889 A1 | 8/2009 |
| WO | WO2011/068952 A1 | 6/2011 |

OTHER PUBLICATIONS

Zhang et al., Patent Examination Report No. 1, AU 2013376536, Nov. 20, 2015, 8 pgs.
Zhang et al., Office Action, CA 2,876,027, Oct. 15, 2015, 7 pgs.
Zhang et al., Extended European Search Report, EP13873591.5, Nov. 11, 2016, 11 pgs.
Zhang et al., Partial Supplementary European Search Report, EP13873591.5, Aug. 9, 2016, 7 pgs.
Zhang et al., International Search Report, PCT/CN2013/091266, Mar. 27, 2014, 4 pgs.

* cited by examiner

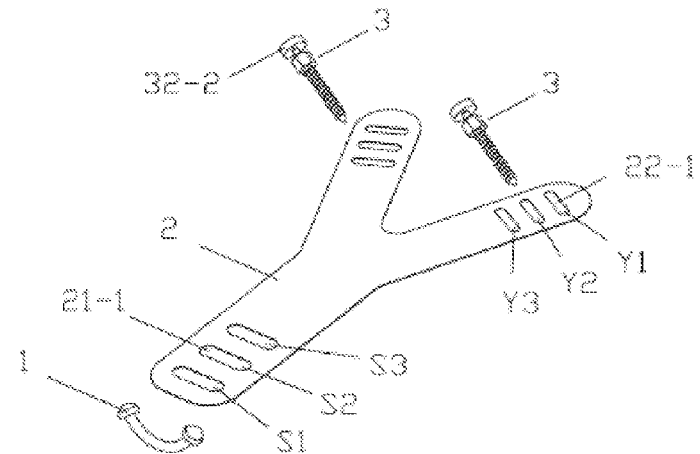
FIG. 9
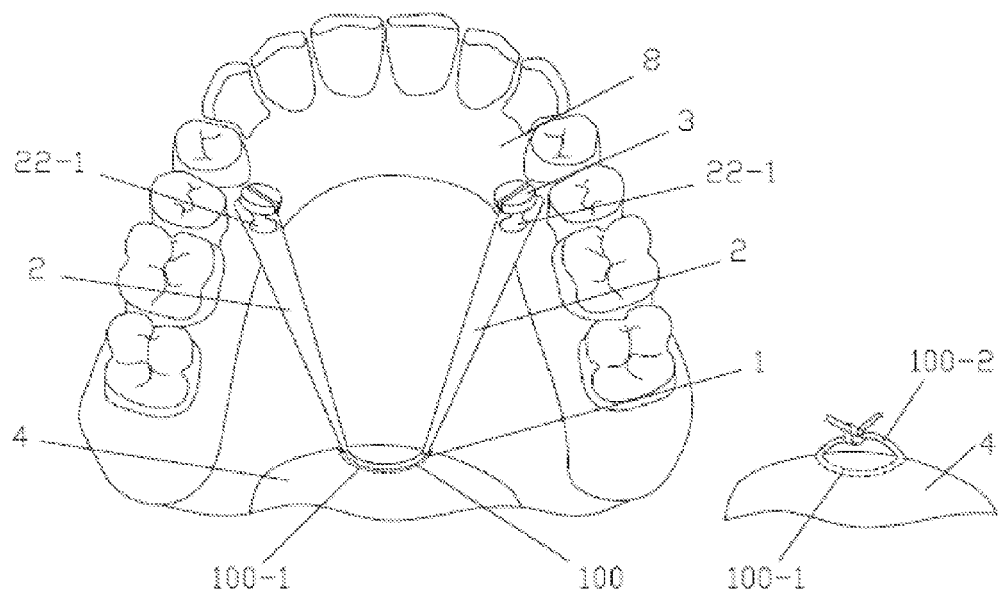
FIG. 10
FIG. 10-1

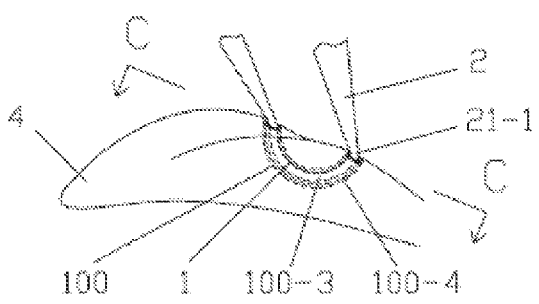
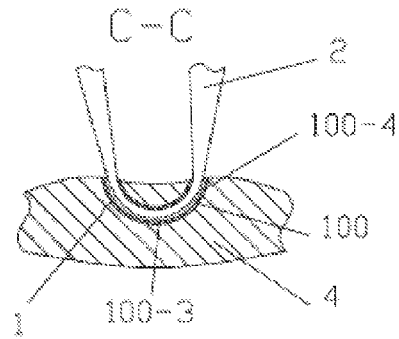
FIG. 11          FIG. 11-1
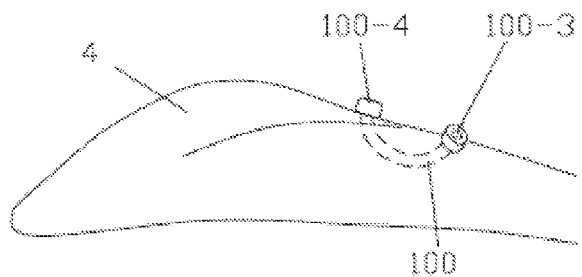
FIG. 11-2
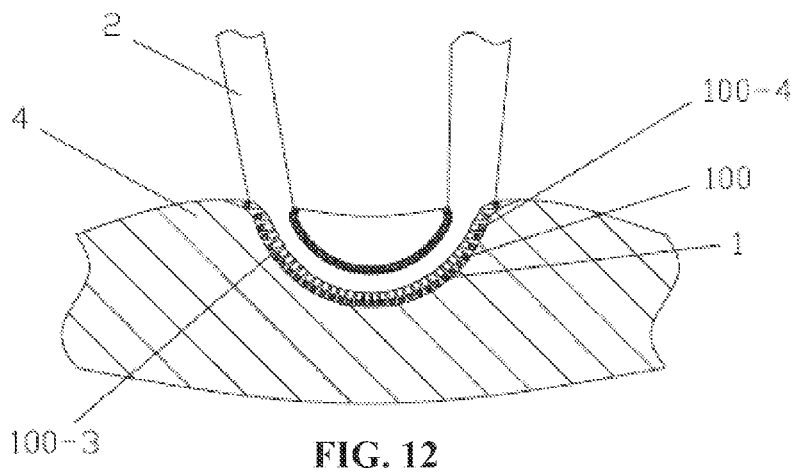
FIG. 12

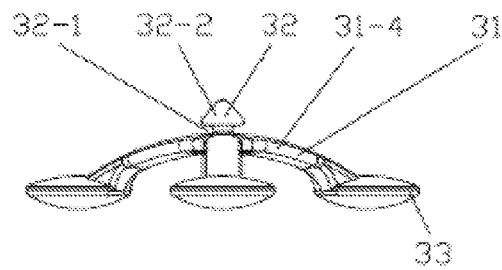
FIG. 21
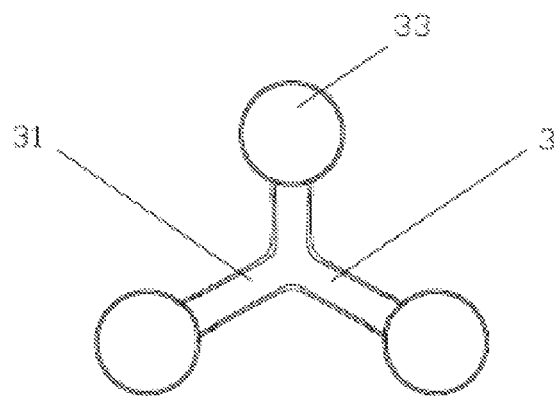
FIG. 21-1
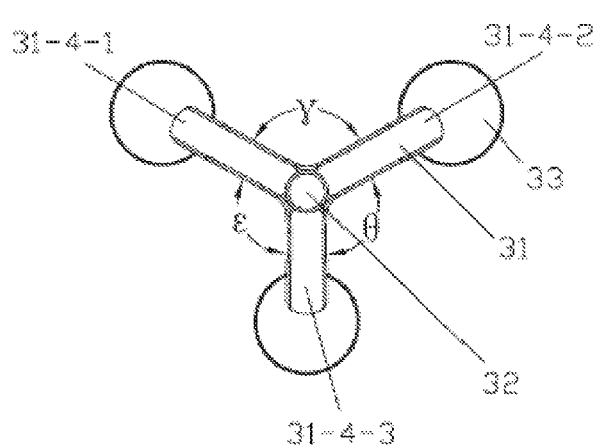
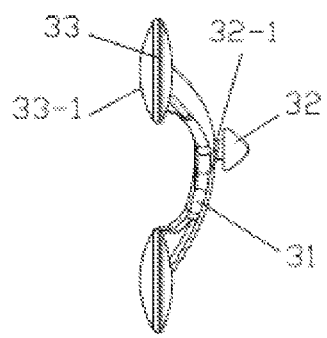
FIG. 21-2  FIG. 21-3

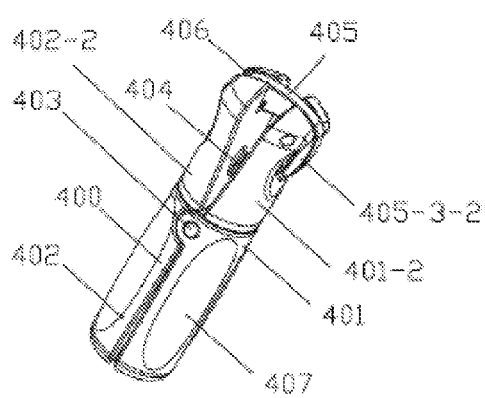
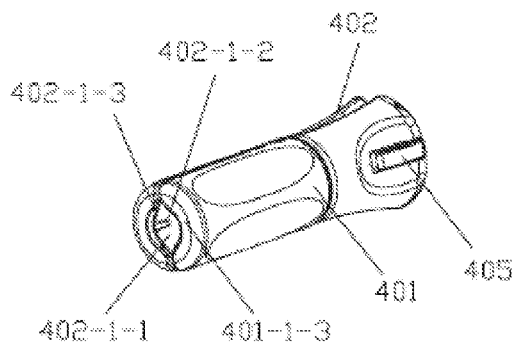
FIG. 23  FIG. 23-1
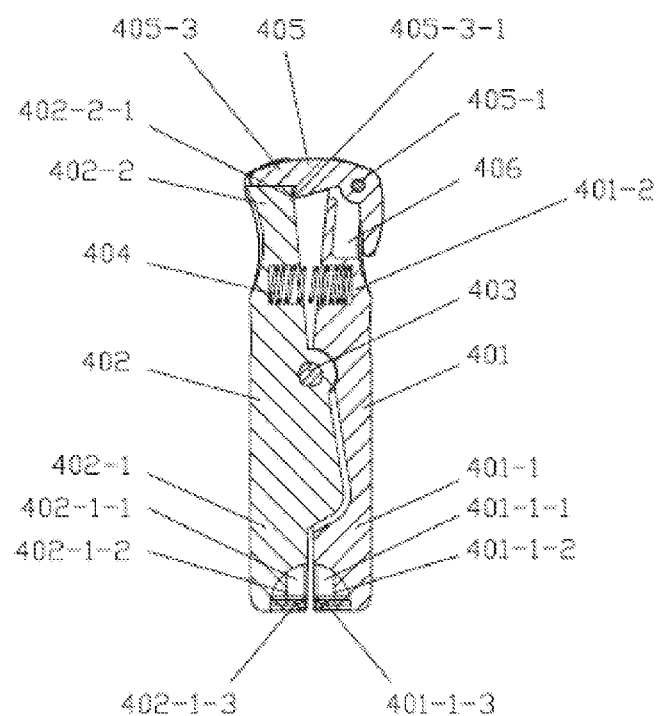
FIG. 23-2

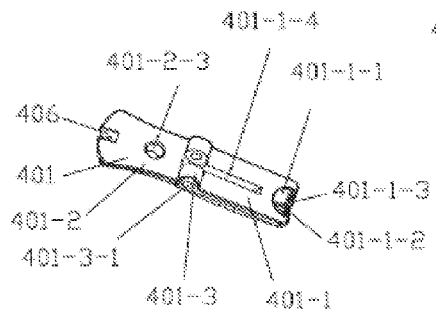
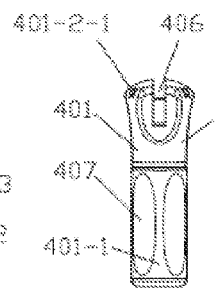
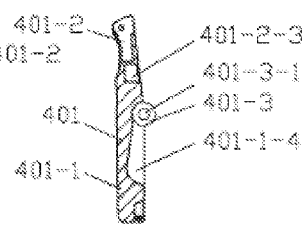
FIG. 23-8   FIG. 23-9   FIG. 23-10
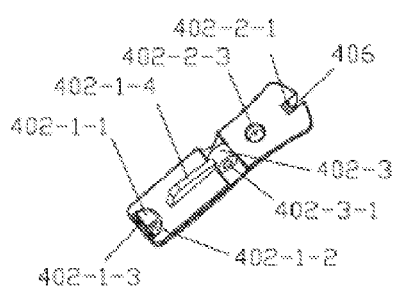
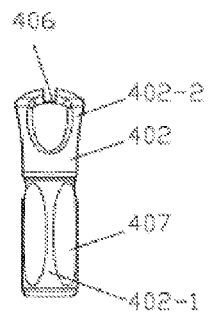
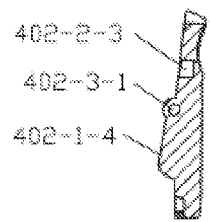
FIG. 23-11   FIG. 23-12   FIG. 23-13
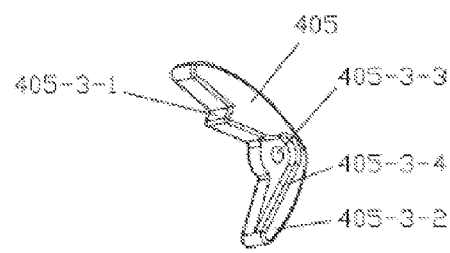
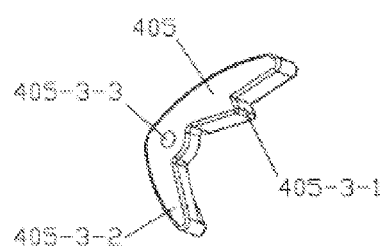
FIG. 23-14   FIG. 23-15

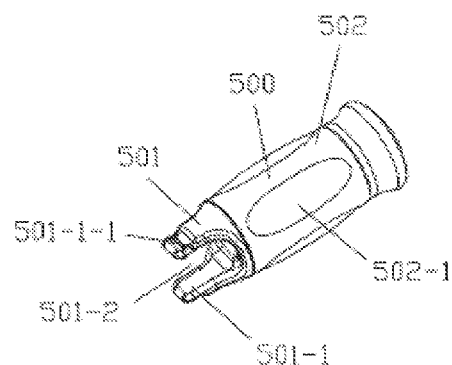
FIG. 24
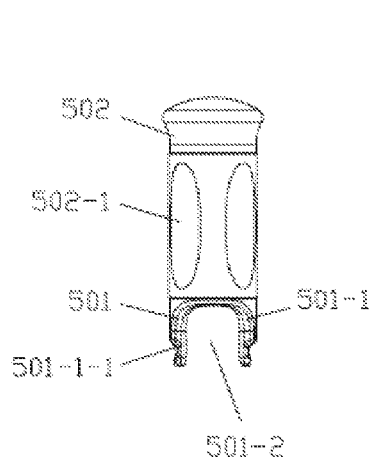 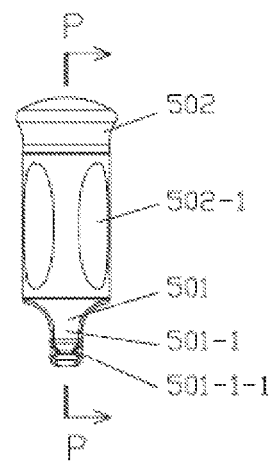 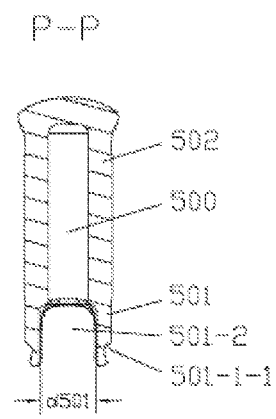
FIG. 24-1    FIG. 24-2    FIG. 24-3

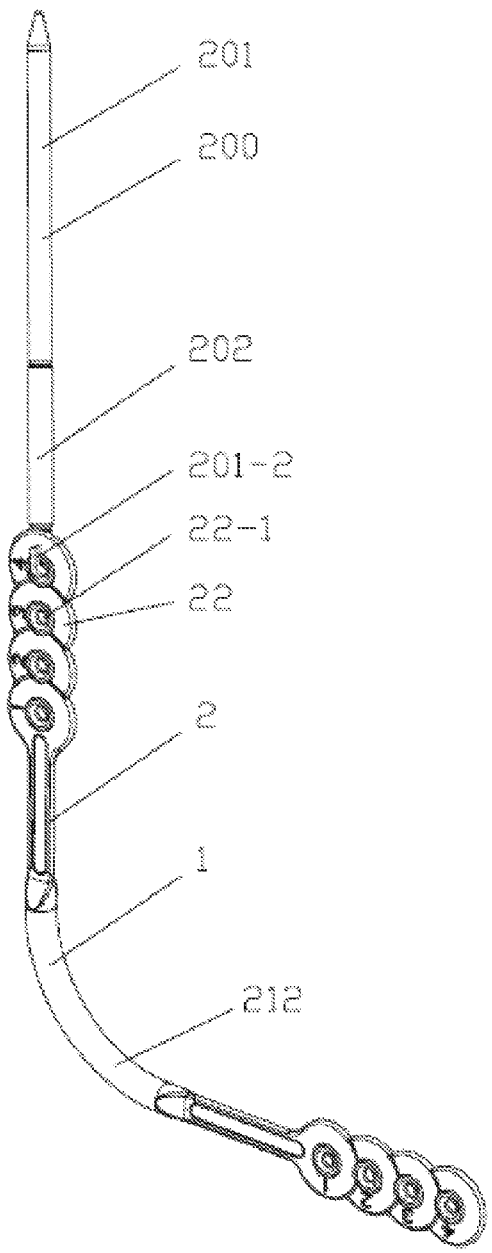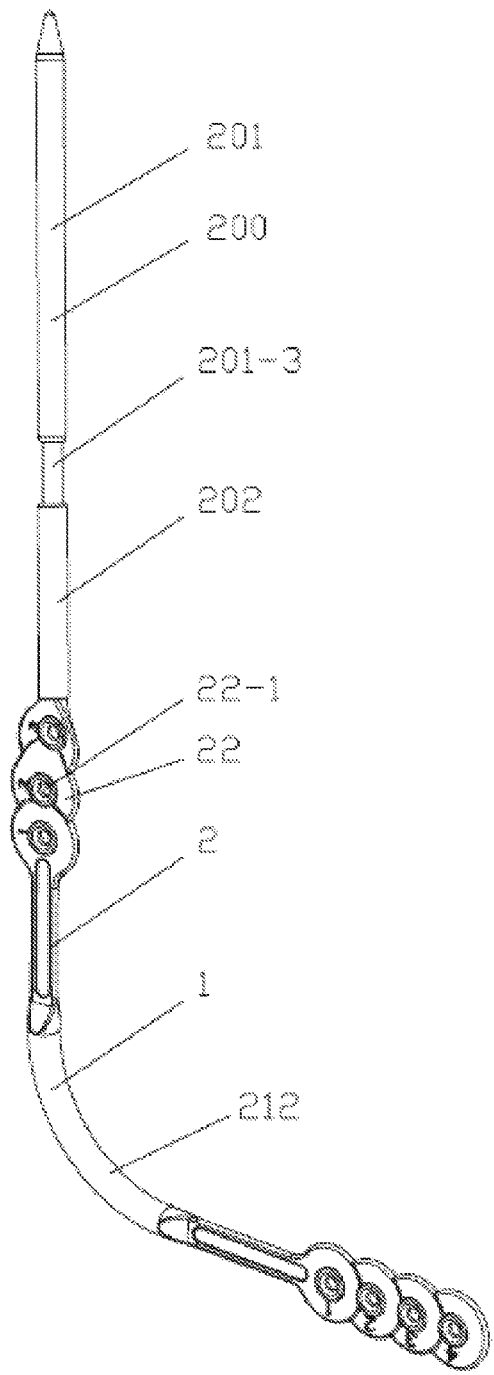
FIG. 25-7  FIG. 25-8

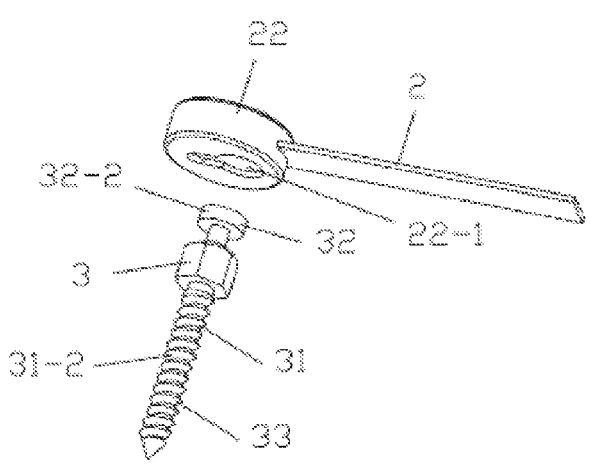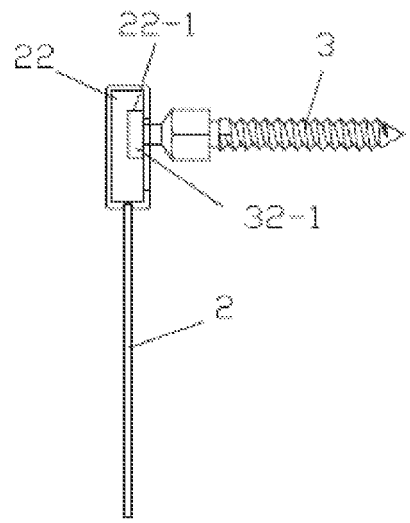
FIG. 29-1  FIG. 29-2
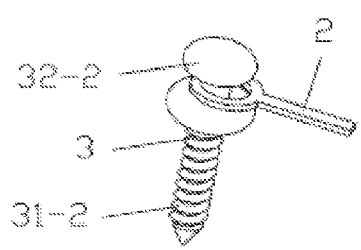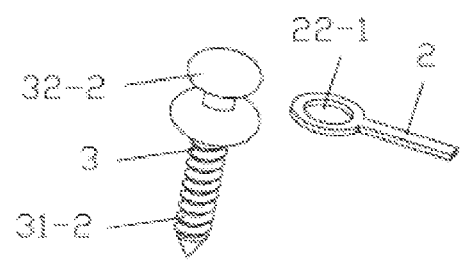
FIG. 30-1  FIG. 30-2

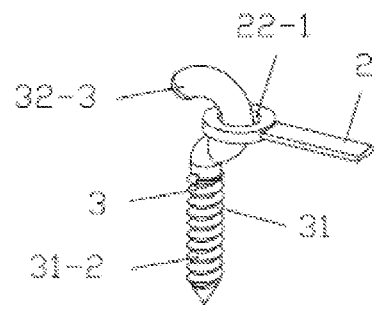
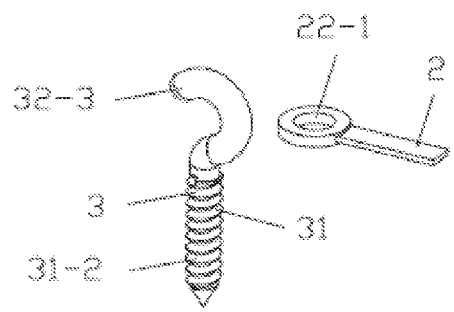
FIG. 31-1    FIG. 31-2
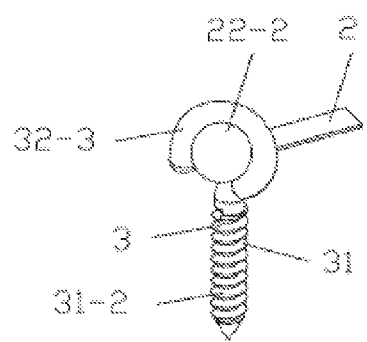
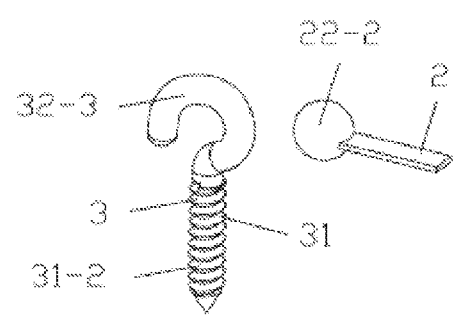
FIG. 32-1    FIG. 32-2

ELASTIC TONGUE-DORSUM RETRACTION DEVICE, CLAMPING PLIERS, INSTALLATION PLIERS, LINE GUIDE AND IMPLANTATION METHOD

CROSS REFERENCE TO RELATED APPLICATIONS

This Application is a United States National Stage Application filed under 35 U.S.C. §371 of PCT Patent Application Serial No. PCT/CN2013/091266 filed on Dec. 31, 2013, which claims the benefit of and priority to Chinese Patent Application No. 201310043949.5 filed Feb. 4, 2013, Chinese Patent Application No. 201320063137.2 filed Feb. 4, 2013, Chinese Patent Application No. 201310423312.9 filed Sep. 16, 2013, Chinese Patent Application No. 201310423315.2 filed Sep. 16, 2013, Chinese Patent Application No. 201310423258.8 filed Sep. 16, 2013, Chinese Patent Application No. 201310423351.9 filed Sep. 16, 2013, Chinese Patent Application No. 201310423355.7 filed Sep. 16, 2013, Chinese Patent Application No. 201310423417.4 filed Sep. 16, 2013, Chinese Patent Application No. 201310423353.8 filed Sep. 16, 2013, Chinese Patent Application No. 201310733988.8 filed Dec. 26, 2013, and Chinese Patent Application No. 201310738009.8 filed Dec. 27, 2013, all of which are hereby incorporated by reference in their entireties.

BACKGROUND OF THE INVENTION

Field of the Invention

The present invention relates to an elastic tongue-dorsum retraction device, clamping pliers, installation pliers, a line guide and an implantation method, and more particularly to an elastic tongue-dorsum retraction device for treating obstructive sleep apnea/hypopnea syndrome (Obstructive Sleep Apnea/Hypopnea Syndrome, OSAHS for short below), tools for use together therewith that include clamping pliers, installation pliers and a line guide, and an implantation method.

Related Art

Obstructive sleep apnea/hypopnea syndrome (OSAHS) is a sleep breathing disorder with clinical features of snoring, apnea and hypopnea caused by collapse and obstruction of soft tissues of the upper airway during sleep.

As for the pathogenesis of OSAHS, it is generally considered that multiple factors work together. Besides the narrow anatomical structure of the upper airway, the main cause is obstruction caused by soft tissue collapse that occurs when pharyngeal muscles for maintaining the upper airway open relax during sleep. The site of obstruction is usually located in the palatopharyngeal and glossopharyngeal planes.

Studies indicate that 20%-25% of OSAHS patients are caused by collapse in the palatopharyngeal plane only, 15%-20% of OSAHS patients are caused by collapse in the glossopharyngeal plane only, and 50%-70% of OSAHS patients suffer from collapse in both the palatopharyngeal and glossopharyngeal planes, that is, are mixed OSAHS patients.

To treat OSAHS caused by sagging and collapse of the tongue, the inventor disclosed an implanted tongue-root retraction device in Chinese Patent Application No. CN102198010 A. This invention has good clinical efficacy, and is particularly suitable for surgical treatment of moderate or severe OSAHS patients caused by collapse of the tongue root.

In addition, there are also various oral appliances for treating snoring and OSAHS in the prior art. For oral appliances in the prior art, generally a device is placed in an oral cavity to move forward the mandible or pull forward the tongue body, so as to enlarge the pharyngeal cavity and release the airway obstruction during sleep. The method has many types and produces a certain effect, but most patients cannot adapt to it. The oral appliance leads to irritation and foreign body sensation, causing that the user cannot fall asleep, and may have temporo-mandibular joint injury with long term use.

SUMMARY OF THE INVENTION

To overcome the defects of the oral appliances in the prior art, the present invention is directed to a tongue dorsum retraction device for treating mild or moderate OSAHS patients caused by sagging and collapse of the tongue, which has advantages of smaller wound, greater comfort, and more convenience in use.

An elastic tongue-dorsum retraction device, where elastic tongue-dorsum retraction device includes a tongue dorsum connection mechanism 1, an elastic retractor 2 and a tooth-side fastener 3, where:

the tongue dorsum connection mechanism 1 is an under-the-tongue-mucosa tunnel-type retraction connection mechanism 100 or a connector 101 disposed at the tongue dorsum, which can prevent sagging of the tongue;

the elastic retractor 2 is made of a medical elastic material, the elastic retractor 2 is an elastic strip-shaped object, an elastic wire-like object or a spring-like object that can stretch and produce a restoring force under the effect of an external force and can restore its original shape after the external force released, or an elastic mechanism including the elastic strip-shaped object, an elastic mechanism including the elastic wire-like object, or an elastic mechanism including the spring-like object;

the tooth-side fastener 3 includes a support bracket 31 capable of supporting the tooth-side fastener 3, an elastic-retractor tooth-side connection mechanism 32 that can be connected to the elastic retractor 2, and a tooth-side fastening mechanism 33 capable of fixing the tooth-side fastener 3 to teeth, the alveolar bone, the maxilla, the mandible, or the maxilla and mandible; and the elastic-retractor tooth-side connection mechanism 32 and the tooth-side fastening mechanism 33 are disposed on the support bracket 31; and the tooth-side fastener 3 serving as a force-bearing fulcrum is fixed to teeth or the alveolar bone through the tooth-side fastening mechanism 33, or the tooth-side fastener 3 is removably fixed outside the maxilla lip, the mandible lip, or the maxilla and mandible lips through the tooth-side fastening mechanism 33; and one end of the elastic retractor 2 is connected to the elastic-retractor tooth-side connection mechanism 32 of the tooth-side fastener 3, and the other end of the elastic retractor 2 is connected to the tongue dorsum connection mechanism 1.

The basic principle of the present invention lies in that: after the tongue dorsum connection mechanism 1 is disposed in a tongue dorsum area in front of circumvallate papillae of the tongue, the elastic retractor 2 is used to elastically retract the tongue dorsum area by using the tooth-side fastener 3 fixed to teeth or the alveolar bone or outside the maxilla and mandible lips as a fulcrum. Since the tongue dorsum connection mechanism 1 is disposed under the mucosa layer of the tongue dorsum and a certain width transversely along the oral cavity, a trench effect can be formed at the tongue root part when the elastic retractor 2 is used to retract the tongue dorsum area, and the sagging tongue root part can be effectively pulled up by using a small retraction force, so as to achieve the objective of enlarging the airway at the glossopharyngeal portion to treat OSAHS. It should be particularly noted that, since the site of retraction is the tongue dorsum area close to the front of circumvallate papillae of the tongue root, and does not extend through the thickness direction of the tongue body, and only elastic retraction over a certain transverse area is provided in a range of the tongue dorsum that has a depth of less than 1 cm under the mucosa of the tongue dorsum and has a transverse width of greater than 1.5 cm along the oral cavity, the movement of the tongue tip and the tongue body is not excessively limited or affected when the tongue root part is effectively pulled up. When the elastic tongue-dorsum retraction device of the present invention is used to retract the tongue, a proper retraction force to the tongue root part is maintained to prevent sagging of the tongue root without excessively affecting the movement of the tongue tip and the tongue body, so that the patient can breathe with mouth closed, which overcomes disadvantages in the prior art that the oral cavity cannot be closed and saliva easily runs out of the mouth due to wearing of an OSAHS oral appliance, and maintains a clear language function and an adequate swallowing function, thereby improving comfort to the patient.

Further, the tongue dorsum connection mechanism 1 is disposed in a tongue dorsum area that is in front of circumvallate papillae of the tongue and has a longitudinal length L of 0 cm to 5 cm, a transverse width W of 0.2 cm to 6 cm and a depth H of 0 cm to 1.0 cm along the oral cavity. The tongue dorsum connection mechanism 1 is disposed and fixed in the above tongue dorsum area, and when the elastic retractor 2 is used to elastically retract the tongue dorsum connection mechanism 1 disposed in the above tongue dorsum area, obstruction of the airway at the glossopharyngeal portion caused by sagging and collapse of the tongue root can be effectively alleviated by using a small elastic retraction force, so as to obtain a good effect of pulling the tongue root forward. When the tongue root is effectively pulled up, and the airway at the glossopharyngeal portion is effectively enlarged, the smaller the used retraction force is, the less the interference with the movement of the tongue is, and the better the comfort is after the tongue is retracted. If the tongue dorsum connection mechanism 1 goes beyond the tongue dorsum retraction area and is adjacent to the tongue root part, strong foreign body sensation is caused, making the patient unable to adapt to or ensure the abruptly increased feeling of discomfort. If the tongue dorsum connection mechanism 1 is adjacent to the tongue tip portion, a large retraction force is required during retraction, and due to good retractability of the tongue tip portion, it is difficult to effectively pull up the tongue root part by the retraction to the tongue tip portion, making it difficult to enlarge the airway at the glossopharyngeal portion and difficult to alleviate obstruction of the airway at the glossopharyngeal portion caused by sagging and collapse of the tongue; in addition, the movement of the tongue tip portion is restricted, affecting sound production and swallowing. Therefore, the tongue dorsum area of the present invention is the optimal area for implanting the tongue dorsum connection mechanism 1, can achieve the optimal effect of enlarging the airway at the glossopharyngeal portion, and does not excessively affect the movement of the tongue, thereby maintaining good sound production and swallowing functions, as shown in FIG. 33.

The elastic retractor 2 forms an elastic retraction force of 15 g to 300 g between the tooth-side fastener 3 and the tongue dorsum connection mechanism 1. The above range of the elastic retraction force is an optimized range of the elastic retraction force, and is selected according to individual differences of patients and the weight of the tongue under the guidance of a doctor, so that not only the sagging tongue can be effectively pulled forward to alleviate stenosis and obstruction of the airway at the glossopharyngeal portion caused by sagging and collapse of the tongue, but also the movement of the tongue is not excessively affected, thereby achieving a good therapeutic effect, maintaining the free movement of the tongue, and ensuring a clear speech function, smooth swallowing and comfortable sleep.

Further, the under-the-tongue-mucosa tunnel-type retraction connection mechanism 100 of the tongue dorsum connection mechanism 1 is an under-the-tongue-mucosa epithelialized tunnel 100-1 left after an implant 100-2 that can form an under-the-tongue-mucosa tunnel after being taken out is removed, or is an under-the-tongue-mucosa tunnel 100-3 that includes a thin-walled tube-shaped implant and is formed under the tongue mucosa after a thin-walled tube-shaped implant 100-4 is implanted. Disclosed herein is a structure of the tongue dorsum connection mechanism 1 of the elastic tongue-dorsum retraction device of the present invention, that is, the tunnel-type retraction connection mechanism 100.

The implant 100-2 that can form an under-the-tongue-mucosa tunnel at the tongue dorsum after being taken out is a medical polymer material tube, a medical polymer material spring tube, a medical polymer material wire, a medical polymer material strip, a medical metal material tube, a medical metal spring tube, a medical metal material wire, or a medical metal material strip.

The thin-walled tube-shaped implant 100-4 is a medical polymer material thin-walled tube, a medical polymer material spring tube, a medical metal thin-walled tube, or a medical metal spring tube.

Further, the tunnel-type retraction connection mechanism 100 is a thin-walled tube-shaped implant 100-4, two ends of the thin-walled tube-shaped implant 100-4 are each provided with an anti-slip positioning convex step 100-4-1, and the anti-slip positioning convex step 100-4-1 has a smooth surface 100-4-2 matching the surface of the tongue mucosa. Since two ends of the thin-walled tube-shaped implant 100-4 of the tunnel-type tongue dorsum connection mechanism 100 are each provided with an anti-slip positioning convex step 100-4-1, the positioning convex step 100-4-1 can prevent the thin-walled tube-shaped implant 100-4 from slipping off from under the tongue mucosa under the effect of an external force, when the thin-walled tube-shaped implant 100-4 is implanted under the tongue mucosa. Moreover, since the positioning convex step 100-4-1 is in surface contact with the tongue mucosa, irritation of the positioning convex step 100-4-1 to the surface of the tongue mucosa is reduced, so that comfort to the user can be enhanced.

An angle β between the two smooth surfaces 100-4-2 at the two ends of the positioning convex steps 100-4-1 is 90° to 180°. After optimization, the angle β is preferably 100° to 150°. The biological shape of the tongue body is an arch structure having a certain angle; therefore, after the two smooth surfaces 100-4-2 of the positioning convex steps 100-4-1 at two ends form an angle β, the positioning convex step 100-4-1 can better conform to the mucosa on the surface of the tongue body after the thin-walled tube-shaped implant 100-4 is implanted under the tongue mucosa, thereby improving comfort to the patient in use.

The tunnel-type retraction connection mechanism 100 is made of a flexible medical material selected from a group consisting of: medical silica gel, medical rubber, medical latex, and medical polyurethane. The tunnel-type tongue dorsum connection mechanism 100 is made of a flexible medical material, and particularly is made of medical silica gel or medical polyurethane; in this case, after the tunnel-type tongue dorsum connection mechanism 100 is implanted under the tongue mucosa, the shape of the tunnel-type tongue dorsum connection mechanism 100 can be properly changed or automatically adjusted according to the movement of the tongue, so as to desirably adapt to the channel under the tongue mucosa. The soft material also provides better flexibility when the positioning convex step 100-4-1 contacts tongue mucosa tissues, which alleviates irritation to tongue mucosa tissues, thereby improving comfort to the patient and compliance of the patient.

Further, the connector 101 of the tongue dorsum connection mechanism 1 is a fully-implantable connector 102 that can be fully implanted under the tongue mucosa, a semi-implantable connector 103 that is partially implanted under the tongue mucosa and partially exposed out of the tongue mucosa, or a mucosa-surface-fixed-type connector 104 that can be fixed to the mucosa of the tongue dorsum. Disclosed herein are three different connection manners between the connector 101 of the tongue dorsum connection mechanism 1 disposed at the tongue dorsum and the tongue: fully-implanted type, semi-implanted type, and surface adhesion type.

The fully-implantable connector 102 is a magnetic flat object 102-1.

The magnetic flat object 102-1 as the fully-implantable connector 102 includes magnetic units 1021-1 and a base body 1021-2, and the magnetic units 1021-1 are distributed on the base body 1021-2. The magnetic units 1021-1 may be connected to the base body 1021-2 in various manners. The magnetic units 1021-1 may be completely wrapped by the base body 1021-2, may be embedded on the soft base body 1021-2, or may be connected in a mesh manner by the base body 1021-2.

The magnetic flat object 102-1 as the fully-implantable connector 102 is magnetically connected to the elastic refractor 2.

The fully-implantable connector 102 or the implanted part of the semi-implantable connector 103 is provided with through holes 106 or convex steps 105 that can prevent displacement of the implant.

The semi-implantable connector 103 includes a support 11 that can be implanted under the mucosa of the tongue dorsum for a long term and an elastic-refractor tongue dorsum connection mechanism 12 that is exposed out of the mucosa of the tongue dorsum and can be connected to the elastic retractor 2, and the elastic-retractor tongue dorsum connection mechanism 12 is disposed on the support 11.

The elastic-retractor tongue dorsum connection mechanism 12 of the semi-implantable connector 103 is a connection concave groove 12-1, a connection convex step 12-2, a connecting hook 12-3, or a connecting ring 12-6 that can be removably connected to the elastic retractor 2.

The support 11 of the semi-implantable connector 103 is one of an arc-shaped support, a U-shaped support, a circular ring-shaped support, or an elliptical ring-shaped support.

Further, when the tongue dorsum connection mechanism 1 is the semi-implantable connector 103, the elastic-refractor tongue dorsum connection mechanism 12 of the semi-implantable connector 103 and the support 11 form a removable integral structure. According to different material properties, the tongue dorsum connection mechanism 1 is generally manufactured by using numerical control machining, precision casting, injection molding or other processes.

When the tongue dorsum connection mechanism 1 is the semi-implantable connector 103, the elastic-retractor tongue dorsum connection mechanism 12 of the semi-implantable connector 103 and the support 11 form a removable combined-type structure. Such an elastic-retractor tongue dorsum connection mechanism 12 and the support 11 form a removable combined-type structure, which can facilitate mounting and removal of the support 11 through the under-the-tongue-mucosa epithelialized tunnel 100-1.

The elastic-retractor tongue dorsum connection mechanism 12 of the semi-implantable connector 103 is mounted on the support 11 by thread connection, concave-convex engagement, interference fit, or adhesion. Definitely, removable structures in other forms may also be used.

Further, when the tongue dorsum connection mechanism 1 is the semi-implantable connector 103, the elastic-retractor tongue dorsum connection mechanism 12 includes a connection convex step 12-2 capable of fixing the elastic retractor 2 and connection concave grooves 12-1 capable of fixing the elastic retractor 2, where at least one connection concave groove 12-1 of the connection concave grooves 12-1 is distributed on the connection convex step 12-2.

The connection concave grooves 12-1 include a transverse connection concave groove 12-1-1 axially perpendicular to the connection convex step 12-2 and longitudinal connection concave grooves 12-1-2 spatially intersecting with the transverse connection concave groove 12-1-1. Generally, the longitudinal connection concave grooves 12-1-2 and the transverse connection concave groove 12-1-1 form an angle of 10° to 90°.

The transverse connection concave groove 12-1-1 and the longitudinal connection concave grooves 12-1-2 can spatially position and fix the tongue-side connection mechanism 21 of the elastic retractor 2 of the elastic tongue-dorsum retraction device. Generally, the elastic retractor 2 has a strip-shaped structure, and when the tongue-side connection mechanism 21 of the elastic retractor 2 having a strip-shaped structure is a tongue-side connection hole 21-1, the tongue-side connection hole 21-1 is passed through the connection convex steps 12-2 and then fixed into the transverse connection concave groove 12-1-1 under the connection convex step 12-2. Moreover, when the elastic retractor 2 having a strip-shaped structure is pulled tight toward the tooth side, the edge of the tongue-side connection hole 21-1 can be automatically locked in the longitudinal connection concave grooves 12-1-2 on the connection convex step 12-2, so as to achieve combined-type fixing through space intersection of the transverse connection concave groove 12-1-1 and the longitudinal connection concave grooves 12-1-2.

The longitudinal connection concave grooves 12-1-2 are perpendicular to the transverse connection concave groove 12-1-1, and evenly distributed on the connection convex step 12-2.

Four longitudinal connection concave grooves 12-1-2 are evenly distributed on the connection convex step 12-2 of the tongue dorsum connection mechanism 1. Such a structure in which four longitudinal connection concave grooves 12-1-2 are evenly distributed on the connection convex step 12-2 cooperate with the transverse connection concave groove 12-1-1, which can provide a function of fixing the elastic retractor 2 through space intersection, thereby preventing the phenomenon of falling during movement of the tongue.

The connection convex step 12-2 of the tongue dorsum connection mechanism 1 is of a semispherical or conical shape having a smooth surface. The so-called connection convex step 12-2 having a smooth surface may be designed into various shapes, among which a semispherical or conical shape that has no sharp edge or barb on its surface is preferred.

A conical transition mechanism 12-4 capable of alleviating irritation of edges of the elastic-refractor tongue dorsum connection mechanism 12 to the mucosa on the surface of the tongue is provided between the elastic-retractor tongue dorsum connection mechanism 12 of the tongue dorsum connection mechanism 1 and the support 11, a diameter d12 of the conical transition mechanism 12-4 close to the elastic-retractor tongue dorsum connection mechanism 12 is greater than a diameter d11 of the conical transition mechanism 12-4 close to the support 11, and a transverse connection concave groove 12-1-1 capable of fixing the elastic retractor 2 is provided between the conical transition mechanism 12-4 and the connection convex step 12-2. By means of the conical transition mechanism 12-4 disposed on the tongue dorsum connection mechanism of the present invention, surface contact between the tongue dorsum connection mechanism 1 and the mucosa on the surface of the tongue can be achieved, so as to alleviate irritation of edges of the elastic-retractor tongue dorsum connection mechanism 12 to the mucosa on the surface of the tongue, thereby improving comfort.

The mucosa-surface-fixed-type connector 104 includes a support base 104-1 that can be adhered or adsorbed to the surface of the mucosa of the tongue dorsum and a connection mechanism 104-2 connected to the elastic retractor 2, the connection mechanism 104-2 is a connection concave groove 1042-1, a connection convex step 1042-2 or a connecting hook 1042-3, and the connection mechanism 104-2 is disposed on the support base 104-1.

The elastic retractor 2 includes a tongue-side connection mechanism 21 that can be connected to the tongue dorsum connection mechanism 1.

The elastic retractor 2 includes a tooth-side connection mechanism 22 that can be connected to the tooth-side fastener 3.

Further, the tongue-side connection mechanism 21 on the elastic refractor 2 and the tongue dorsum connection mechanism 1 form a removable connection, and the tongue-side connection mechanism 21 is a structure such as a tongue-side connection hole 21-1, a tongue-side connection convex step 21-2, a tongue-side connecting hook 21-3, or a tongue-side connecting line 21-4. Disclosed herein are several specific connection manners between the elastic retractor 2 and the tongue dorsum connection mechanism 1.

The tooth-side connection mechanism 22 on the elastic retractor 2 and the tooth-side fastener 3 form a removable connection, and the tooth-side connection mechanism 22 is a structure such as a tooth-side connection hole 22-1, a tooth-side connection convex step 22-2, a tooth-side connecting hook 22-3, or a tooth-side connecting line 22-4. Disclosed herein are several specific connection manners between the elastic retractor 2 and the tooth-side fastener 3.

Further, the elastic retractor 2 is a medical elastic film or elastic strip-shaped object, the medical elastic film or elastic strip-shaped object is made of a medical silica gel film, a medical latex film, a medical polyurethane film, a medical rubber film or an elastic medical material braid, and the medical elastic film or elastic strip-shaped object has a thickness of 0.01 mm to 3 mm. Disclosed herein is an optimized thin-film thickness of the elastic retractor 2, and a required elastic retraction force, that is, a retraction force of less than 300 g, can be obtained in the above thickness range.

The elastic retractor 2 is a medical elastic wire-like object, the medical elastic wire-like object is made of medical silica gel, medical latex, medical polyurethane, medical rubber or an elastic medical material braid, and the medical elastic wire-like object has a diameter of 0.05 mm to 5 mm. Disclosed herein is an optimized diameter of the elastic retractor 2, and a required elastic retraction force, that is, a retraction force of less than 300 g, can be obtained in the above diameter range.

Further, the elastic retractor 2 includes a tongue-side connection mechanism 21, an elastic deformation mechanism 20 and a tooth-side connection mechanism 22; the tongue-side connection mechanism 21 and the tooth-side connection mechanism 22 are separately disposed at two ends of the elastic retractor 2, the tongue-side connection mechanism 21 is provided with one tongue-side connection hole 21-1, and the tooth-side connection mechanism 22 is provided with at least one tooth-side connection hole 22-1; and the elastic deformation mechanism 20 is disposed between the tongue-side connection mechanism 21 and the tooth-side connection mechanism 22. Since the tooth-side connection mechanism 22 is provided with a plurality of tooth-side connection holes 22-1, the magnitude of the elastic retraction force of the elastic deformation mechanism 20 can be conveniently adjusted by using the tooth-side connection holes 22-1 at different positions of the tooth-side connection mechanism 22.

Under the same force conditions, the amount of elastic deformation of the elastic deformation mechanism 20 of the elastic refractor 2 that undergoes elastic deformation is greater than the amount of elastic deformation of the tooth-side connection mechanism 22 or the tongue-side connection mechanism 21; and when the elastic deformation mechanism 20 undergoes elastic deformation, the tongue-side connection mechanism 21 or the tooth-side connection mechanism 22 almost does not undergo elastic deformation. Generally, under the same force conditions, the amount of elastic deformation of the elastic deformation mechanism 20 that undergoes elastic deformation is preferable more than three times the amount of elastic deformation of the tongue-side connection mechanism 21 or the tooth-side connection mechanism 22.

When the elastic refractor 2 is made of elastic materials having same properties, the area of the cross-section of the elastic deformation mechanism 20 is not only less than the area of the cross-section of the tooth-side connection mechanism 22, but also is less than the area of the cross-section of the tongue-side connection mechanism 21. Generally, the area of the cross-section of the elastic deformation mechanism 20 is only 30% or less of the area of the cross-section of the tooth-side connection mechanism 22 or the tongue-side connection mechanism 21.

A protruding edge 21-1-1 capable of increasing the tensile resistance is provided around the tongue-side connection hole 21-1 provided on the tongue-side connection mechanism 21 of the elastic retractor 2. The protruding edge 21-1-1 around the tongue-side connection hole 21-1 can effectively encircle the elastic-retractor tongue dorsum connection mechanism 12, which is connected to the elastic retractor, on the tongue dorsum connection mechanism 1, so as to prevent the three-stage elastic retractor 2 from accidentally falling off from the elastic-retractor tongue dorsum connection mechanism 12.

A protruding edge 22-1-1 capable of increasing the tensile resistance is provided around the tooth-side connection hole 22-1 provided on the tooth-side connection mechanism 22 of the elastic retractor 2. The protruding edge 22-1-1 around the tooth-side connection hole 22-1 can effectively encircle the tooth-side fastener 3, so as to prevent the three-stage elastic retractor 2 from accidentally falling off from the tongue dorsum connection mechanism 1.

The tongue dorsum connection mechanism 1 and the elastic retractor 2 can be integrally formed by using an integral manufacturing technology so as to form an integral-type elastic retraction mechanism 212, and the integral-type elastic retraction mechanism 212 includes the tongue dorsum connection mechanism 1 and the elastic retractor 2.

The integral-type elastic refraction mechanism 212 includes a tooth-side connection mechanism 22, an elastic deformation mechanism 20 and a tongue-side connection mechanism 21; the tooth-side connection mechanism 22 is located at two ends of the integral-type elastic retraction mechanism 212, and the tooth-side connection mechanism 22 is provided with at least one tooth-side connection hole 22-1; the tongue dorsum connection mechanism 1 is located in the middle of the integral-type elastic retraction mechanism 212; the elastic deformation mechanism 20 is disposed between the tongue dorsum connection mechanism 1 and the tooth-side connection mechanism 22; and the elastic deformation mechanism 20 is connected to the tongue dorsum connection mechanism 1 through the tongue-side connection mechanism 21.

Under the same force conditions, the amount of elastic deformation of the elastic deformation mechanism 20 of the integral-type elastic retraction mechanism 212 that undergoes elastic deformation is greater than the amount of elastic deformation of the tongue dorsum connection mechanism 1. When the elastic deformation mechanism 20 undergoes elastic deformation, the tongue dorsum connection mechanism 1 almost does not undergo elastic deformation. Generally, under the same force conditions, the amount of elastic deformation of the elastic deformation mechanism 20 that undergoes elastic deformation is preferably more than three times the amount of elastic deformation of the tongue dorsum connection mechanism 1. In other words, the elastic deformation resistance of the tongue dorsum connection mechanism 1 is at least more than three times that of the elastic deformation mechanism 20.

Under the same force conditions, the amount of elastic deformation of the elastic deformation mechanism 20 of the integral-type elastic retraction mechanism 212 that undergoes elastic deformation is greater than the amount of elastic deformation of the tooth-side connection mechanism 22. When the elastic deformation mechanism 20 undergoes elastic deformation, the tooth-side connection mechanism 22 almost does not undergo elastic deformation. Generally, under the same force conditions, the amount of elastic deformation of the elastic deformation mechanism 20 that undergoes elastic deformation is preferably more than three times the amount of elastic deformation of the tooth-side connection mechanism 22. In other words, the elastic deformation resistance of the tooth-side connection mechanism 22 is at least more than three times that of the elastic deformation mechanism 20.

The integral-type elastic retraction mechanism 212 is a strip-shaped elastic object, and the tooth-side connection mechanism 22, the elastic deformation mechanism 20, the tongue-side connection mechanism 21 and the tongue dorsum connection mechanism 1 are arranged in the following order:

the tooth-side connection mechanism 22-the elastic deformation mechanism 20-the tongue-side connection mechanism 21-the tongue dorsum connection mechanism 1-the tongue-side connection mechanism 21-the elastic deformation mechanism 20-the tooth-side connection mechanism 22.

A protruding edge 22-1-1 capable of increasing the tensile resistance is provided around the tooth-side connection hole 22-1 provided on the tooth-side connection mechanism 22 of the integral-type elastic retraction mechanism 212. The protruding edge 22-1-1 can effectively encircle the tooth-side fastener 3, so as to prevent the integral-type elastic retraction mechanism 212 from accidentally falling off from the tooth-side fastener 3.

When the integral-type elastic retraction mechanism 212 is made of elastic materials having same properties, the area of the cross-section of the elastic deformation mechanism 20 is not only less than the area of the cross-section of the tooth-side connection mechanism 22, but also is less than the area of the cross-section of the tongue dorsum connection mechanism 1. Generally, the area of the cross-section of the elastic deformation mechanism 20 is only 30% or less of the area of the cross-section of the tooth-side connection mechanism 22 or the tongue dorsum connection mechanism 1. The integral-type elastic retraction mechanism 212 may be integrally made of an elastic material, and it is achieved by changing the area of the cross-section that the deformation resistance of the elastic deformation mechanism 20 is less than the deformation resistance of the tooth-side connection mechanism 22 or the tongue dorsum connection mechanism 1. In a working state in which a pull force of below 300 g is exerted on the integral-type elastic retraction mechanism 212, the elastic deformation mechanism 20 undergoes elastic deformation, and the tooth-side connection mechanism 22 or the tongue dorsum connection mechanism 1 almost does not undergo elastic deformation. In addition, the transition area between the tongue dorsum connection mechanism 1 and the elastic deformation mechanism 20 forms the tongue-side connection mechanism 21.

The integral-type elastic retraction mechanism 212 can be passed through the under-the-tongue-mucosa epithelialized tunnel 100-1, and the tongue dorsum connection mechanism 1 has an arc segment matching the under-the-tongue-mucosa epithelialized tunnel 100-1.

The integral-type elastic retraction mechanism 212 can be passed through the epithelialized tunnel 100-1 under the tongue mucosa of the tongue dorsum, and the tongue dorsum connection mechanism 1 can provide an effective supporting and fixing function for the under-the-tongue-mucosa epithelialized tunnel 100-1; the two tooth-side connection mechanisms 22 are located at two ends of the integral-type elastic retractor 2, and conveniently fix it to the tooth-side fastener 3; and the elastic deformation mechanism 20 disposed between the tooth-side connection mechanism 22 and the tongue dorsum connection mechanism 1 exerts a proper elastic retraction force on the tongue, which can not only pull up forward the collapsed tongue root to prevent OSAHS caused by collapse of the tongue root, but also does not affect the movement of the tongue, so that good language ability is maintained during treatment of snoring or OSAHS, thereby improving comfort to the patient.

The tooth-side connection mechanism 22 on the elastic retractor 2 is connected to the tooth-side fastener 3 by magnetic connection. For example, the tooth-side connection mechanism 22 on the elastic retractor 2 is made of a neodymium-iron-boron magnetic material wrapped by medical silica gel, and the tooth-side fastener 3 is made of a ferromagnetic medical stainless steel material, so that the tooth-side connection mechanism 22 that includes the magnetic material on the elastic retractor 2 can be magnetically attracted to the tooth-side fastener 3. Definitely, magnetic connection mechanisms having other specific structures may also be designed to achieve the technical solution of the present invention.

The tongue-side connection mechanism 21 on the elastic retractor 2 is connected to the tongue dorsum connection mechanism 1 by magnetic connection. For example, the tongue-side connection mechanism 21 on the elastic refractor 2 is made of a neodymium-iron-boron magnetic material wrapped by medical silica gel, the tongue dorsum connection mechanism 1 is made of a ferromagnetic medical stainless steel material, and the tongue dorsum connection mechanism 1 is implanted in the tongue dorsum area, so that the tongue-side connection mechanism 21 that includes the magnetic material on the elastic retractor 2 can be magnetically attracted to the tongue dorsum connection mechanism 1. Definitely, magnetic connection mechanisms having other specific structures may also be designed to achieve the technical solution of the present invention.

The support bracket 31 of the tooth-side fastener 3 is a tooth-side fixing support bracket 31-1 fixed to upper teeth or lower teeth, a dental bone nail-type fixing support bracket 31-2 fixed to the alveolar bone, a dental sleeve-type fixing support bracket 31-3 removably fit to upper teeth or lower teeth, or a support bracket 31-4 fixed outside the lip that is removably fit outside the upper and lower lips. Four manners of fixing the tooth-side fastener 3 to the oral cavity are described herein by way of example: adhered to teeth, implanted on the alveolar bone, sleeved over teeth, and fixed outside the maxilla and mandible lips.

Further, according to the technical solution of the present invention, a triangular outside-the-lip type tooth-side fastener 3 is described by way of example, where the tooth-side fastener 3 is characterized in that:

A. the elastic-retractor tooth-side connection mechanism 32 of the tooth-side fastener 3 includes a positioning concave groove 32-1 and a positioning convex step 32-2 that are capable of fixing the tooth-side fastener of the elastic refractor 2;

B. the tooth-side fastener 3 at least includes three support brackets 31-4 fixed outside the lip; and C. the support bracket 31-4 fixed outside the lip is an arch structure; the support bracket 31-4 fixed outside the lip has one end intersecting with and connected to the elastic-retractor tooth-side connection mechanism 32, and the other end provided with the tooth-side fastening mechanism 33; and the tooth-side fastener 3 forms a radiated arch structure that uses the elastic-retractor tooth-side connection mechanism 32 as the center, uses the support brackets 31-4 fixed outside the lip as arch-shaped supporting legs, and uses surfaces at the bottom of the tooth-side fastening mechanism 33 that are in contact with the skin outside the maxilla and mandible as supporting points.

The support bracket 31-4 fixed outside the lip is an arch structure. When the elastic retractor 2 is fixed to the outside-the-lip type tooth-side fastener 3, the outward protruding arch structure of the support bracket 31-4 prevents direct contact of the support bracket 31-4 fixed outside the lip with sensitive tissues such as the upper and lower lips. In this way, the upper and lower lips do not contact the support bracket 31-4 fixed outside the lip even during speaking or breathing through the mouth, and only the smooth curved surface 33-1 at the bottom of the tooth-side fastening mechanism 33 disposed at the bottom of the support bracket 31-4 contacts the skin outside the maxilla, the skin outside the mandible, and the skin outside the lip corners. Since these supporting points experience a small amount of movement during speaking or breathing through the mouth, comfort to the patient during wearing and use is improved.

The tooth-side fastener 3 includes three support brackets 31-4 fixed outside the lip, including a support bracket 31-4-1 fixed outside the maxilla lip, a support bracket 31-4-2 fixed outside the mandible lip, and a support bracket 31-4-3 at the lip corner; an angle γ between the support bracket 31-4-1 fixed outside the maxilla lip and the support bracket 31-4-2 fixed outside the mandible lip is not less than an angle ε between the support bracket 31-4-1 fixed outside the maxilla lip and the support bracket 31-4-3 at the lip corner; and the angle γ between the support bracket 31-4-1 fixed outside the maxilla lip and the support bracket 31-4-2 fixed outside the mandible lip is not less than an angle θ between the support bracket 31-4-2 fixed outside the mandible lip and the support bracket 31-4-3 at the lip corner.

The length of the support bracket 31-4-1 fixed outside the maxilla lip or the support bracket 31-4-2 fixed outside the mandible lip is not less than the length of the support bracket 31-4-3 at the lip corner.

The support bracket 31-4-1 fixed outside the maxilla lip, the support bracket 31-4-2 fixed outside the mandible lip, and the support bracket 31-4-3 at the lip corner of the outside-the-lip type tooth-side fastener 3 are respectively supported outside the maxilla lip, outside the mandible lip and outside the lip corner to form a triangular supporting structure. Such a triangular supporting structure used by the outside-the-lip type tooth-side fastener of the present invention not only provides stable fixing and support, but also has a light weight, enabling the outside-the-lip type tooth-side fastener of the present invention to meet requirements of human biology.

A surface of the tooth-side fastening mechanism 33 in contact with the skin surface is a smooth curved surface 33-1. When the outside-the-lip type tooth-side fastener 3 is fixed outside the maxilla and mandible through the elastic retractor 2, the tooth-side fastening mechanism 33 is in surface contact with the skin surface, so that the skin surface receives a small force per unit area. In addition, the smooth contact with the curved surface can reduce irritation of the tooth-side fastening mechanism 33 to the skin surface, and the user can improve comfort to the user by using the outside-the-lip type tooth-side fastener 3.

The positioning convex step 32-2 is a smooth conical structure. The smooth conical structure has a guiding function, and when the elastic retractor 2 is fixed to the positioning concave groove 32-1 through the positioning convex step 32-2, the smooth conical structure of the positioning convex step 32-2 can facilitate fixing of the elastic retractor 2, and the smooth surface does no harm to the tooth-side connection hole 22-1 of the elastic retractor 2, thereby improving safety of the elastic retractor 2 in use.

Further, according to the technical solution of the present invention, an I-shaped tooth-side fastener 3 adhered to teeth is described by way of example, where the tooth-side fastener 3 is characterized in that:

A. the elastic-retractor tooth-side connection mechanism 32, the support bracket 31 and the tooth-side fastening mechanism 33 form a tooth-side fastener 3 having an I-shaped cross-section;

B. the elastic-retractor tooth-side connection mechanism 32, which is connected to the elastic retractor 2, of the tooth-side fastener 3 is a spherical crown-shaped positioning convex step 32-2 having a smooth surface;

C. the support bracket 31 is a smooth column; and

D. the tooth-side fastening mechanism 33 is a housing 33-1 having a radian matching the surface of teeth.

Since the tooth-side connection mechanism 32 uses the spherical crown-shaped design having a smooth surface, when the tooth-side connection mechanism 32 is fixed to the surface of teeth, contact between the tooth-side connection mechanism 32 and mucosa tissues in the oral cavity of the human body is smooth surface contact, which can minimize irritation to mucosa tissues in the oral cavity of the human body, thereby ensuring comfort to the patient in long-term use.

When the elastic retractor 2 is connected to the tooth-side fastener 3 through the tooth-side connection mechanism 22, the tooth-side connection hole 22-1 of the tooth-side connection mechanism 22 encircles the support bracket 31 and is embedded in the positioning concave groove 32-1. Since the support bracket 31 uses the design of a smooth column, the smooth surface does no harm to the tooth-side connection hole 22-1 of the elastic retractor 2, thereby improving safety of the elastic retractor 2 in use.

Since the part of the tooth-side fastening mechanism 33 adhered to teeth has a radian matching the surface of teeth, the tooth-side fastening mechanism 33 can better conform to the surface of teeth, which better ensures the reliability of adhesion of the tooth-side fastening mechanism 33 to the surface of teeth, thereby improving safety of the tooth-side fastener 3 in use.

The housing 33-1 having a radian matching the surface of teeth of the tooth-side fastening mechanism 33 is provided with glue accommodating holes 33-1-1. Since the housing 33-1 of the tooth-side fastening mechanism 33 is provided with the glue accommodating holes 33-1-1, the contact area between the adhesive and the tooth-side fastening mechanism 33 during adhesion of the tooth-side fastening mechanism 33 to the surface of teeth can be increased, so that the tooth-side fastening mechanism 33 is adhered to the surface of teeth more firmly, thereby better ensuring safety of the tooth-side fastener 3 in use.

Further, the tooth-side fastener 3 includes a retraction-force adjustment mechanism 34 capable of adjusting the magnitude of the retraction force of the elastic retractor.

The retraction-force adjustment mechanism 34 is a rotation mechanism 34-1 capable of pulling up the elastic retractor 2 or loosening the elastic retractor 2 through rotational movement.

The refraction-force adjustment mechanism 34 is a sliding mechanism 34-2 capable of tightening or loosening the elastic retractor 2 through sliding.

The elastic retractor 2, the tongue dorsum connection mechanism 1 or the tooth-side fastener 3 is in a color matching that of human tissues. For example, the tongue dorsum connection mechanism 1 is transparent or in a color close to that of the tongue mucosa, so as to achieve invisibility. Likewise, the medical elastic film serving as the elastic retractor 2 may also be transparent or in a color matching that of the mucosa of the oral cavity, so as to achieve invisibility. In addition, the tooth-side fastener 3 adhesively fixed to the tooth side may be in a color close to that of teeth, and the tooth-side fastener 3 fixed to gums by using a dental nail is in a color close to that of the mucosa of gums. These designs and changes in color are for the purpose of achieving invisibility and pleasing appearance.

The present invention further discloses tools for mounting an elastic tongue-dorsum retraction device of the present invention, which include clamping pliers 400, installation pliers 500, and a line guide 200.

Further, clamping pliers 400 for mounting an elastic tongue-dorsum retraction device, characterized in that:

A. the clamping pliers 400 include a right arm 401, a left arm 402 and a rotating shaft 403;

B. the right arm 401 includes a right clamp head 401-1, a right-arm tail 401-2, and a right-arm rotating-shaft mounting convex step 401-3; the right clamp head 401-1 includes a right working groove 401-1-1, right anti-detachment restricting convex steps 401-1-3, and at least one right rotation restricting convex step 401-1-2; and the right-arm rotating-shaft mounting convex step 401-3 is provided with a through hole 401-3-1 for mounting the rotating shaft;

C. the left arm 402 includes a left clamp head 402-1, a left-arm tail 402-2, and a left-arm rotating-shaft mounting convex step 402-3; the left clamp head 402-1 includes a left working groove 402-1-1, left anti-detachment restricting convex steps 402-1-3, and at least one left rotation restricting convex step 402-1-2; and the left-arm rotating-shaft mounting convex step 402-3 is provided with a through hole 402-3-1 for mounting the rotating shaft; and D. the right-arm rotating-shaft mounting convex step 401-3 and the left-arm rotating-shaft mounting convex step 402-3 match each other in shape; midlines of the through hole 401-3-1 of the right arm for mounting the rotating shaft and the through hole 402-3-1 of the left arm for mounting the rotating shaft are in a same straight line; and the rotating shaft 403 can be sequentially passed through the through hole 401-3-1 on the right-arm rotating-shaft mounting convex step and the through hole 402-3-1 on the left-arm rotating-shaft mounting convex step, so that the right arm 401 and the left arm 402 can be opened or closed by means of the rotating shaft 403.

Further, a space formed by the right working groove 401-1-1 and the left working groove 402-1-1 of the clamping pliers 400 when the clamping pliers 400 are maintained in a closed state can accommodate a connection convex step 12-2 of a tongue dorsum connection mechanism 1 of the elastic tongue-dorsum retraction device; the right anti-detachment restricting convex steps 401-1-3 and the left anti-detachment restricting convex steps 402-1-3 can be removably embedded in a transverse connection concave groove 12-1-1 of the connection convex step 12-2; and the right rotation restricting convex step 401-1-2 and the left rotation restricting convex step 402-1-2 can be removably embedded in longitudinal connection concave grooves 12-1-2.

When maintained in the closed state, the clamping pliers 400 can desirably encircle the connection convex step 12-2 of the tongue dorsum connection mechanism 1; and the right anti-detachment restricting convex steps 401-1-3 and the left anti-detachment restricting convex steps 402-1-3 are embedded in the transverse connection concave groove 12-1-1 of the connection convex step 12-2, which can effectively prevent the connection convex steps 12-2 from accidentally falling off from the clamping pliers 400. In addition, in the working state, the right rotation restricting convex step 401-1-2 and the left rotation restricting convex step 402-1-2 are embedded in the longitudinal connection concave grooves 12-1-2, and during rotation of the clamping pliers 400, the connection convex step 12-2 can be effectively fixed in the clamping pliers 400 through the right rotation restricting convex step 401-1-2 and the left rotation restricting convex step 402-1-2, so that the connection convex step 12-2 does not rotate relative to the clamping pliers 400. By rotating the clamping pliers 400, the connecting nut 12-7 of the connection convex step 12-2 of the tongue dorsum connection mechanism 1 of the elastic tongue-dorsum retraction device can be conveniently screwed onto the connecting bolt 11-7 of the support 11 of the tongue dorsum connection mechanism 1 of the elastic tongue-dorsum retraction device. In addition, the existence of the right anti-detachment restricting convex steps 401-1-3 and the left anti-detachment restricting convex steps 402-1-3 can prevent the connecting nut 12-7 of the connection convex step 12-2 from accidentally slipping to fall into the human body to become a foreign body.

The clamping pliers 400 include a restoring spring 404; the restoring spring 404 is disposed between the right-arm tail 401-2 and the left-arm tail 402-2, and has one end supported on the right-arm tail 401-2, and the other end supported on the left-arm tail 402-2, or the restoring spring 404 is wound on the rotating shaft 403, and has one end supported on the right-arm tail 401-2, and the other end supported on the left-arm tail 402-2; and the restoring spring 404 can exert an opening force between the right-arm tail 401-2 and the left-arm tail 402-2.

The clamping pliers 400 include a self-lock mechanism 405, and the self-lock mechanism 405 is characterized in that:

A. the self-lock mechanism 405 is disposed on the right-arm tail 401-2 and the left-arm tail 402-2; and a mounting groove 406 of the self-lock mechanism is provided on the right-arm tail 401-2 and the left-arm tail 402-2;

B. the self-lock mechanism 405 includes a pin 405-1, a torsion spring 405-2, and a self-lock positioning block 405-3;

C. the right-arm tail 401-2 is provided with a pin hole 401-2-1 for mounting the self-lock mechanism 405;

D. after the pin 405-1 is sequentially passed through the pin hole 401-2-1, the torsion spring 405-2 and the self-lock positioning block 405-3, the self-lock mechanism 405 is fixed in the mounting groove 406 of the right-arm tail 401-2; and the torsion spring 405-2 is disposed in the torsion-spring mounting groove 405-3-4 on the self-lock positioning block 405-3, and has one end supported on the right-arm tail 401-2, and the other end supported on the self-lock positioning block 405-3, so as to form a closing force for the self-lock positioning block 405-3; and E. the self-lock positioning block 405-3 includes a lock tooth 405-3-1, a self-lock switch 405-3-2, and a mounting through hole 405-3-3; the lock tooth 405-3-1 forms concave-convex engagement with a positioning convex step 402-2-1 of the mounting groove 406 of the self-lock mechanism on the left-arm tail 402-2; and the self-lock switch 405-3-2 protrudes out of the unlocking groove 401-2-2, and the pin 405-1 can be passed through the mounting through hole 405-3-3, so as to movably mount the self-lock positioning block 405-3 into the mounting groove 406 of the right arm 401.

When the lock tooth 405-3-1 on the self-lock positioning block 405-3 is disposed on the positioning convex step 402-2-1 of the mounting groove 406 of the self-lock mechanism on the left arm 402, it can be ensured that the right clamp head 401-1 and the left clamp head 402-1 of the clamping pliers 400 are maintained in a closed state. Only when the operator intentionally presses down the self-lock switch 405-3-2 on the self-lock positioning block 405-3, the lock tooth 405-3-1 can be removed from the positioning convex step 402-2-1, so as to open the right clamp head 401-1 and the left clamp head 402-1 of the clamping pliers 400. During working, opening of the right clamp head 401-1 and the left clamp head 402-1 of the clamping pliers 400 due to an incorrect operation can be effectively avoided, thereby preventing the connecting nut 12-7 of the connection convex step 12-2 of the tongue dorsum connection mechanism 1 of the elastic tongue-dorsum retraction device from accidentally falling off from the clamping pliers 400.

An outer side of the right arm 401 and an outer side of the left arm 402 of the clamping pliers 400 are provided with an anti-slip pattern or an anti-slip groove 407. In the working state, the anti-slip pattern or anti-slip groove 407 can increase the friction force between the operator and the right arm 401 and the left arm 402 of the clamping pliers 400, so that the slipping phenomenon of the clamping pliers 400 can be effectively avoided during working.

The right arm 401 and the left arm 402 of the clamping pliers 400 are provided with a positioning and guiding block 402-1-4 and a positioning and guiding groove 401-1-4 that cooperate with each other in pair to provide a guiding function and a positioning function. When the right arm 401 and the left arm 402 are closed, the positioning and guiding block 402-1-4 and the positioning and guiding groove 401-1-4 form concave-convex engagement, which can ensure that the right arm 401 and the left arm 402 will not be dislocated during the closing process, so that the right rotation restricting convex step 401-1-2 and the left rotation restricting convex step 402-1-2 can be accurately embedded into the longitudinal connection concave grooves 12-1-2 on the tongue dorsum connection mechanism 1 of the elastic tongue-dorsum retraction device, thereby ensuring smooth operation.

The clamping pliers 400 include a right arm 401, a left arm 402 and a rotating shaft 403. A cavity formed by the right working groove 401-1-1 and the left working groove 402-1-1 when the clamping pliers 400 are maintained in a closed state can accommodate the connection convex step 12-2 of the tongue dorsum connection mechanism 1. The right rotation restricting convex step 401-1-2 and the left anti-detachment restricting convex steps 402-1-3 are embedded in the transverse connection concave groove 12-1-1 of the tongue dorsum connection mechanism 1; the right rotation restricting convex step 401-1-2 and the left rotation restricting convex step 402-1-2 can be embedded in the longitudinal connection concave grooves 12-1-2 of the tongue dorsum connection mechanism 1; and the connecting nut 12-7 of the connection convex step 12-2 of the tongue dorsum connection mechanism 1 of the elastic tongue-dorsum retraction device can be conveniently screwed onto the connecting bolt 11-7 of the support 11 of the tongue dorsum connection mechanism 1. The self-lock mechanism 405 of the clamping pliers 400 can prevent opening of the clamping pliers 400 in case of an incorrect operation, so as to prevent the connection convex step 12-2 from accidentally falling off from the clamping pliers 400.

Further, installation pliers 500 for mounting an elastic refractor of an elastic tongue-dorsum retraction device, characterized in that:

A. the installation pliers 500 include an opening end 501 and a handle end 502;

B. the opening end 501 at least includes one bracket 501-1; and

C. a receiving space 501-2 formed by the bracket 501-1 can accommodate a connection convex step 12-2 on a tongue dorsum connection mechanism 12 of the elastic tongue-dorsum retraction device.

Further, the bracket 501-1 is provided with a groove 501-1-1 that can prevent a tongue-side connection mechanism 21 of the elastic retractor 2 from falling. The bracket 501-1 is designed with the groove 501-1-1; therefore, when the tongue-side connection mechanism 21 of the elastic retractor 2 is disposed on the bracket 501-1 of the installation pliers 500, the tongue-side connection mechanism 21 of the elastic retractor 2 does not fall off from the installation pliers 500 during movement of the installation pliers 500 because the groove 501-1-1 on the bracket 501-1 of the installation pliers 500 provides a positioning function, thereby making the installation pliers 500 safer and more convenient in the working process.

Further, two brackets 501-1 are symmetrically distributed on the opening end 501, and a distance d501 between the two symmetrically distributed brackets 501-1 is greater than the greatest diameter of the connection convex step 12-2 of the elastic-retractor tongue dorsum connection mechanism 12. During operation, the tongue-side connection hole 21-1 of the elastic retractor 2 is enlarged and then sleeved over two symmetrical brackets 501-1, the connection convex step 12-2 on the tongue dorsum connection mechanism 1 is disposed in the enlarged tongue-side connection hole 21-1, and the installation pliers 500 are taken out, so that the elastic retractor 2 slips off from the bracket 501-1, and the tongue-side connection hole 21-1 is embedded in the transverse connection concave groove 12-1-1 of the connection convex step 12-2 of the tongue dorsum connection mechanism 1. In this way, connection of the elastic retractor 2 to the tongue dorsum connection mechanism 1 is completed.

A surface of the handle end 502 is provided with an anti-slip groove, an anti-slip fin or an anti-slip pattern 502-1. The anti-slip groove, anti-slip fin or anti-slip pattern on the surface of the handle end 502 enhances the friction force between the operator and the installation pliers 500, which can effectively prevent the installation pliers 500 from falling off from the hand of the operator during use.

The installation pliers 500 are made of a medical material that can directly contact the human body, including: a medical metal material, a medical polymer material, or a composite material of a medical metal material and a medical polymer material. The installation pliers 500 are made of a medical polymer material that can directly contact the human body, so that when the installation pliers 500 are used to mount the elastic retractor 2, no harmful effect will be produced upon the user even if the brackets 500-1 of the installation pliers 500 often directly contact the tongue mucosa of the human body.

The installation pliers 500 include an opening end 501 and a handle end 502, the opening end 501 includes at least one bracket 501-1, and a receiving space 501-2 formed by the bracket 501-1 can accommodate the connection convex step 12-2 on the tongue dorsum connection mechanism 12 of the elastic tongue-dorsum retraction device 1. The bracket 501-1 is provided with a groove 501-1-1 that can prevent the tongue-side connection mechanism 21 of the elastic retractor 2 from falling. A surface of the handle end 502 is provided with an anti-slip groove, an anti-slip fin or an anti-slip pattern 502-1, which effectively prevents the installation pliers 500 from slipping out of the hand of the operator in use. The installation pliers 500 is made of a medical polymer material, and produces no harmful effect on the human body even if it frequently contact human tissues.

Further, a line guide 200 for mounting an integral-type elastic retraction mechanism of an elastic tongue-dorsum retraction device, characterized in that:

A. the line guide 200 includes a line guiding rod 201 and a slide block 202;

B. the line guiding rod 201 includes a smooth guide head 201-1, a mounting hook 201-2 for mounting an elastic refractor 2, and a limiting groove 201-3 for limiting a sliding distance of the slide block 202;

C. the slide block 202 includes a sliding convex step 202-1; and the sliding convex step 202-1 of the slide block 202 can slide in the limiting groove 201-3 of the line guiding rod 201; and D. when the sliding convex step 202-1 is located at one end of the limiting groove 201-3 adjacent to the guide head 201-1, the slide block 202 cannot cover the mounting hook 201-2; and when the sliding convex step 202-1 is located at one end of the limiting groove 201-3 adjacent to the mounting hook 201-2, the slide block 202 can cover the mounting hook 201-2.

Further, the limiting groove 201-3 has a circular cross-section. Since the limiting groove 201-3 uses a round rod-shaped structure having a smooth surface, and the slide block 202 encircles and slides on the surface of the limiting groove 201-3, no additional guiding mechanism is required, thereby achieving a simple structure. Moreover, the guiding function of the limiting groove 201-3 for the slide block 202 is effectively enhanced, so that sliding of the slide block 202 on the surface the limiting groove 201-3 is more stable, making it less probable for the phenomenon of unsmooth guiding due to the deviation in guiding to occur in the guiding process of the elastic retractor 2.

The slide block 202 is a thin-walled tube provided with an inward flange at one end adjacent to the guide head 201-1, and the inward flange forms the sliding convex step 202-1. Since the slide block 202 uses an inwardly flanged structure to form the sliding convex step 202-1, smooth transition of the sliding convex step 202-1 is achieved, so that the line guide 200 is in surface contact with the surface of the under-the-tongue-mucosa epithelialized tunnel 100-1 during working, which alleviates irritation to the mucosa on the surface of the tongue, and can improve comfort to the human body in the working process of the line guide 200.

The mounting hook 201-2 is a U-shaped or J-shaped hook. Further, a guiding design may be additionally provided at the tail of the mounting hook 201-2, so that the integral-type elastic refraction mechanism 212 can be disposed in the mounting hook 201-2 more conveniently in the process of using the line guide 200.

The line guide 200 includes a line guiding rod 201 and a slide block 202, and the sliding convex step 202-1 of the slide block 202 can slide in the limiting groove 201-3 of the line guiding rod 201. When the slide block 202 is at one end adjacent to the guide head 201-1, the slide block 202 cannot cover the mounting hook 201-2; when the slide block 202 is at one end adjacent to the mounting hook 201-2, the slide block 202 can cover the mounting hook 201-2. When the integral-type elastic retraction mechanism 212 of the elastic tongue-dorsum refraction device 1 is connected to the line guide of the present invention, the line guide 200 can drive the integral-type elastic retraction mechanism 212 to conveniently pass through the under-the-tongue-mucosa epithelialized tunnel 100-1.

The top end of the guide head 201-1 is a cone having a smooth surface; therefore, in the process of guiding out the integral-type elastic refraction mechanism 212 by using the line guide 200, the guide head 201-1 is in surface contact with the under-the-tongue-mucosa epithelialized tunnel 100-1, which can effectively alleviate irritation to the mucosa on the surface of the tongue. Moreover, when the line guide 200 is obstructed in the process of guiding out the integral-type elastic retraction mechanism 212, the guide head 201-1 can easily bypass the obstruction, thereby achieving a smooth guiding process.

In a working state, first, the slide block 202 is slid to an end portion of the limiting groove 201-3 adjacent to the guide head 201-1, and the tooth-side connection hole 22-1 of the integral-type elastic retraction mechanism 212 is disposed in the mounting hook 201-2. Then, the slide block 202 is slid to an end portion of the limiting groove 201-3 adjacent to the mounting hook 201-2, and the mounting hook 201-2 is completely covered by the slide block 202. After the assembled line guide 200 for the integral-type elastic refraction mechanism 212 is smoothly guided out through the under-the-tongue-mucosa epithelialized tunnel 100-1 by using the guide head 201-1, the slide block 202 is slid to the end portion of the limiting groove 201-3 adjacent to the guide head 201-1 to expose the mounting hook 201-2; then, the tooth-side connection hole 22-1 of the integral-type elastic retraction mechanism 212 is removed from the mounting hook 201-2, thereby completing the process of guiding out the integral-type elastic retraction mechanism 212 by using the line guide 200.

In the working state, by sliding the slide block 202, the mounting hook 201-2 can be completely covered, and the integral-type elastic retraction mechanism 212 can be desirably fixed to the mounting hook 201-2, so that when the line guide 200 is passed through the under-the-tongue-mucosa epithelialized tunnel 100-1, the integral-type elastic retraction mechanism 212 does not fall off from the mounting hook 201-2. Moreover, since the mounting hook 201-2 is not exposed out of the slide block 202, the mounting hook 201-2 is effectively prevented from directly contacting and irritating the surface of the tongue mucosa, thereby greatly improving comfort and smoothness of the guiding process.

IMPLANTATION METHODS OF THE PRESENT INVENTION

There are five implantation methods of an elastic tongue-dorsum retraction device of the present invention according to structural types of specific products, including: an implantation method of an elastic tongue-dorsum retraction device that uses under-the-tongue-mucosa epithelialized tunnel-type refraction and connection, an implantation method of an elastic tongue-dorsum retraction device that uses under-the-tongue-mucosa thin-walled tube tunnel-type retraction and connection, an implantation method of an elastic tongue-dorsum retraction device that includes an under-the-tongue-mucosa fully-implantable connector, an implantation method of an elastic tongue-dorsum retraction device that includes an under-the-tongue-mucosa semi-implantable connector, and an implantation method of an elastic tongue-dorsum retraction device that includes a mucosa-surface-fixed-type connector.

Implantation Method 1: Implantation Method of an Elastic Tongue-Dorsum Retraction Device of the Present Invention that Uses Under-the-Tongue-Mucosa Epithelialized Tunnel-Type Retraction and Connection Step 1: An under-the-mucosa tunnel-type retraction connection mechanism is disposed in front of circumvallate papillae of the tongue.

Through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, an implant 100-2, which can form an under-the-tongue-mucosa tunnel, of a tongue dorsum connection mechanism 1 is implanted and fixed, so that two ends of the implant 100-2 are exposed out of the tongue mucosa.

After 15 days to 60 days after the surgery, after the implant 100-2 is removed, an under-the-tongue-mucosa epithelialized tunnel 100-1 that can bear a certain pull force is formed under the mucosa of the tongue dorsum, and the under-the-tongue-mucosa epithelialized tunnel 100-1 is used as an under-the-tongue-mucosa tunnel-type retraction connection mechanism 100 of the present invention.

For example, a medical silica gel tube or medical silica gel strip is used as the implant 100-2 of the present invention that can form an under-the-tongue-mucosa tunnel and implanted at the tongue dorsum, and then two ends of the medical silica gel tube or medical silica gel strip that are exposed out of the mucosa of the tongue dorsum are connected to form a ring and fixed. After 15 days to 60 days after the surgery, the medical silica gel tube or medical silica gel strip is removed. In this way, an epithelialized tunnel 100-1 can be formed under the tongue mucosa. The under-the-tongue-mucosa epithelialized tunnel 100-1 is used as the under-the-tongue-mucosa tunnel-type retraction connection mechanism 100 of the present invention.

Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient. In addition, the tooth-side fasteners 3 of the present invention have different structural types and corresponding fixing methods, and are respectively mounted and fixed by using teeth, the alveolar bone, the maxilla, the mandible, or positions outside the maxilla and mandible lips as supporting and fixing points of the tooth-side fastener 3.

Step 3: Before sleep, the elastic tongue-dorsum retraction device of the present invention is worn.

Before sleep, by using an auxiliary tool, an elastic retractor 2 is passed through the under-the-tongue-mucosa epithelialized tunnel 100-1 formed at the tongue dorsum. After the elastic retractor 2 is passed through the under-the-tongue-mucosa epithelialized tunnel 100-1, two ends of the elastic retractor 2 or the integral-type elastic retraction mechanism 212 are fixed to the tooth-side fastener 3, thereby completing the process of mounting and wearing the elastic tongue-dorsum retraction device of the present invention.

Step 4: After getting up, the elastic tongue-dorsum retraction device of the present invention is removed.

The elastic retractor 2 or the integral-type elastic retraction mechanism 212 is taken off from the tooth-side fastener 3, and drawn out from the under-the-tongue-mucosa epithelialized tunnel 100-1, so as to release refraction to the tongue dorsum.

Implantation Method 2: Implantation Method of an Elastic Tongue-Dorsum Retraction Device of the Present Invention that Uses Under-the-Tongue-Mucosa Thin-Walled Tube Tunnel-Type Retraction and Connection Step 1: An under-the-mucosa tunnel-type retraction connection mechanism is disposed in front of circumvallate papillae of the tongue.

Through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, a thin-walled tube-shaped implant 100-4 of a tongue dorsum connection mechanism 1 is implanted and fixed, so that tube openings at two ends of the thin-walled tube-shaped implant 100-4 are exactly exposed out of the surface of the tongue mucosa. After 15 days to 60 days after the surgery, if a patient does not feel pain or discomfort when the surgically implanted thin-walled tube-shaped implant 100-4 is pulled, refraction to the tongue dorsum can be carried out. The under-the-tongue-mucosa tunnel 100-3 that includes a thin-walled tube-shaped implant formed after the thin-walled tube-shaped implant 100-4 is implanted and fixed under the tongue mucosa is used as an under-the-tongue-mucosa tunnel-type retraction connection mechanism 100 of the present invention.

Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient. In addition, the tooth-side fasteners 3 of the present invention have different structural types and corresponding fixing methods, and are respectively mounted and fixed by using teeth, the alveolar bone, the maxilla, the mandible, or the maxilla and mandible as supporting and fixing points of the tooth-side fastener 3.

Step 3: Before sleep, the elastic tongue-dorsum retraction device of the present invention is worn.

Before sleep, by using an auxiliary tool, an elastic retractor 2 or an integral-type elastic retraction mechanism 212 is passed through an under-the-tongue-mucosa tunnel 100-3 that includes a thin-walled tube-shaped implant and is formed at the tongue dorsum. After the elastic retractor 2 or the integral-type elastic retraction mechanism 212 is passed through the tunnel 100-3, two ends of the elastic retractor 2 or the integral-type elastic retraction mechanism 212 are fixed to the tooth-side fastener 3, thereby completing the process of mounting and wearing the elastic tongue-dorsum retraction device of the present invention.

Step 4: After getting up, the elastic tongue-dorsum retraction device of the present invention is removed.

After getting up, the elastic retractor 2 or the integral-type elastic retraction mechanism 212 is taken off from the tooth-side fastener 3, and drawn out from the under-the-tongue-mucosa tunnel 100-3 that includes a thin-walled tube-shaped implant, so as to release retraction to the tongue dorsum.

Implantation Method 3: Implantation Method of an Elastic Tongue-Dorsum Retraction Device of the Present Invention that Includes an Under-the-Tongue-Mucosa Fully-Implantable Connector Step 1: A fully-implantable connector is implanted in front of circumvallate papillae of the tongue.

Through a minimally invasive surgery under local anesthesia, on two sides that are about 0 cm to 5 cm in front of circumvallate papillae on the surface of the mucosa of the tongue dorsum and are at a distance of about 0.5 cm to 2 cm from the midline, a surgical instrument is used to transversely cut the tongue mucosa to make an incision having a width of about 0.5 cm. Then a special instrument is used to implant a fully-implantable connector 102 under the tongue mucosa from front to back. At least one fully-implantable connector 102 having a magnetic material of the present invention is implanted on each of the left and right sides of the midline of the tongue. The fully-implantable connector 102 of the present invention has a magnetic material.

Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient. In addition, the tooth-side fasteners 3 of the present invention have different structural types and corresponding fixing methods, and are respectively mounted and fixed by using teeth, the alveolar bone, the maxilla, the mandible, or the maxilla and mandible as supporting and fixing points of the tooth-side fastener 3.

Step 3: Before sleep, the elastic tongue-dorsum retraction device of the present invention is worn.

Before sleep, one end of an elastic retractor 2 is fixed to the tooth-side fastener 3, and the other end, which has a magnetic material, of the elastic retractor 2 is inserted into a part of the tongue dorsum portion that is adjacent to the fully-implantable connector 102 of the present invention. Under the effect of a magnetic force, the end, which has the magnetic material, of the elastic retractor 2 and the magnetic fully-implantable connector 102 are attracted to each other form a magnetic connection. The tongue is pulled up forward under the effect of an elastic restoring force of the elastic retractor 2, thereby completing the process of mounting and wearing the elastic tongue-dorsum retraction device of the present invention.

Step 4: After getting up, the elastic tongue-dorsum retraction device of the present invention is removed.

After getting up, the elastic retractor 2 is taken off from the tooth-side fastener 3, and the end, which has the magnetic material, of the elastic retractor 2 is also separated and removed from the tongue dorsum portion, so as to release retraction to the tongue dorsum.

Implantation Method 4: Implantation Method of an Elastic Tongue-Dorsum Retraction Device of the Present Invention that Includes an Under-the-Tongue-Mucosa Semi-Implantable Connector Step 1: A semi-implantable connector is implanted in front of circumvallate papillae of the tongue.

Through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, a semi-implantable connector 103 of a tongue dorsum connection mechanism 1 is implanted and fixed, so that a support 11 of the semi-implantable connector 103 is buried under the tongue mucosa, and an elastic-refractor tongue dorsum connection mechanism 12 is exposed out of the surface of the tongue mucosa. After 15 days to 60 days after the surgery, if a patient does not feel pain or discomfort when the surgically implanted semi-implantable connector 103 is pulled, retraction to the tongue dorsum can be carried out Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient. In addition, the tooth-side fasteners 3 of the present invention have different structural types and corresponding fixing methods, and are respectively mounted and fixed by using teeth, the alveolar bone, the maxilla, the mandible, or the maxilla and mandible as supporting and fixing points of the tooth-side fastener 3.

Step 3: Before sleep, the elastic tongue-dorsum retraction device of the present invention is worn.

Before sleep, one end of an elastic refractor 2 is fixed to the tooth-side fastener 3, the other end of the elastic retractor 2 is fixed to the elastic-retractor tongue dorsum connection mechanism 12 of the semi-implantable connector 103, and by using the tooth-side fastener 3 as a fulcrum, the elastic retractor 2 exerts an elastic pull force on the semi-implantable connector 103. The tongue is pulled up forward under the effect of an elastic restoring force of the elastic retractor 2, thereby completing the process of mounting and wearing the elastic tongue-dorsum retraction device of the present invention.

Step 4: After getting up, the elastic tongue-dorsum retraction device of the present invention is removed.

After getting up, the elastic retractor 2 is taken off from the tooth-side fastener 3, and the elastic retractor 2 is also separated and removed from the elastic-retractor tongue dorsum connection mechanism 12 of the semi-implantable connector 103 of the tongue dorsum connection mechanism 1, so as to release retraction to the tongue dorsum.

Implantation Method 5: Implantation Method of an Elastic Tongue-Dorsum Retraction Device of the Present Invention that Includes a Mucosa-Surface-Fixed-Type Connector Step 1: A mucosa-surface-fixed-type connector of the present invention is adhesively fixed in front of circumvallate papillae of the tongue.

A patient performs actions before a mirror, that is, opens the mouth, protrudes the tongue, cleans and dries the surface of the tongue dorsum, and applies a medical adhesive. Then, a medical adhesive is applied on an adhesion surface of a support base 104-1 of a fixed-outside-the-mucosa type connector 104 of the present invention. Then, the fixed-outside-the-mucosa type connector 104 of the present invention on which the medical adhesive is applied is adhesively fixed to the surface of the tongue dorsum.

Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient. In addition, the tooth-side fasteners 3 of the present invention have different structural types and corresponding fixing methods, and are respectively mounted and fixed by using teeth, the alveolar bone, the maxilla, the mandible, or the maxilla and mandible as supporting and fixing points of the tooth-side fastener 3.

Step 3: Before sleep, the elastic tongue-dorsum retraction device of the present invention is worn.

Before sleep, one end of an elastic refractor 2 is fixed to the tooth-side fastener 3, the other end of the elastic refractor 2 is connected and fixed to an elastic-retractor tongue dorsum connection mechanism 104-2 of the fixed-outside-the-mucosa type connector 104, and by using the tooth-side fastener 3 as a fulcrum, the elastic retractor 2 exerts an elastic pull force on the fixed-outside-the-mucosa type connector 104. The tongue is pulled up forward under the effect of an elastic restoring force of the elastic retractor 2, thereby completing the process of mounting and wearing the elastic tongue-dorsum retraction device of the present invention.

Step 4: After getting up, the elastic tongue-dorsum retraction device of the present invention is removed.

After getting up, the elastic retractor 2 is taken off from the tooth-side fastener 3, and the elastic retractor 2 and the fixed-outside-the-mucosa type connector 104 of the present invention are separated and removed from the tongue dorsum, so as to release refraction to the tongue dorsum.

Advantages of the Present Invention

The elastic tongue-dorsum retraction device of the present invention includes a tongue dorsum connection mechanism 1, an elastic retractor 2 and a tooth-side fastener 3. The elastic retractor 2 has one end fixed to the tooth-side fastener 3, and the other end connected to the tongue dorsum connection mechanism 1. The elastic retractor 2 forms an elastic retraction force between the tongue dorsum connection mechanism 1 and the tooth-side fastener 3. The elastic retractor 2 generates a pull force of 15 g to 300 g, and by elastic retraction of the elastic retractor 2, the tongue dorsum is directly pulled up forward to prevent sagging of the tongue and enlarge the airway at the glossopharyngeal portion, thereby achieving the objective of treating snoring and OSAHS.

Since the elastic retractor 2 elastically retracts the tongue dorsum connection mechanism 1, the movement of the tongue is not affected when the tongue dorsum is properly pulled up, and certain swallowing and speech functions can be maintained, so that not only the airway at the glossopharyngeal portion is enlarged, but also good comfort is provided. Particularly, for the elastic tongue-dorsum retraction device with the retraction-force adjustment mechanism 34 of the present invention, the retraction force to the tongue dorsum portion can be adjusted to an optimal value. In addition, the elastic tongue-dorsum retraction device of the present invention is easy to mount and convenient to use, clean and sterilize.

BRIEF DESCRIPTION OF THE DRAWINGS

FIG. 1-1 is an enlarged view of part A of FIG. 1;

FIG. 1-2 is an enlarged view of part B of FIG. 1;

FIG. 1-3 is a schematic structural view of a tongue dorsum connection mechanism of FIG. 1;

FIG. 1-4 is a schematic structural view of an elastic retractor of FIG. 1;

FIG. 1-5 is a schematic structural view of a tooth-side fastener of FIG. 1;

FIG. 1-6 is a schematic structural view of the tooth-side fastener of FIG. 1 that is adhesively fixed to the inner side of upper teeth;

FIG. 1-7 is a schematic structural view of the tongue dorsum connection mechanism of FIG. 1 that is implanted at the tongue dorsum;

FIG. 1-8 is a schematic view of a position of the tooth-side fastener of FIG. 1 that is fixed to the inner side of upper teeth;

FIG. 2 is a schematic structural view of an elastic tongue-dorsum retraction device of the present invention that is adhesively fixed to the outer side of teeth;

FIG. 3 is a schematic structural view of an elastic tongue-dorsum retraction device of the present invention that is fixed to the inner side of the alveolar bone by using a dental nail;

FIG. 3-1 is a schematic structural view of a tooth-side fastener and an elastic refractor of FIG. 3;

FIG. 3-2 is a schematic structural view of an elastic tongue-dorsum retraction device of the present invention where an elliptical ring-shaped tongue dorsum connection mechanism is connected using a single thin-film strip-shaped elastic retractor;

FIG. 4 is a schematic structural view of an elastic tongue-dorsum retraction device of the present invention that is fixed to the outer side of the alveolar bone by using a dental nail;

FIG. 5 is a schematic structural view of a dental sleeve-fixing type elastic tongue-dorsum retraction device of the present invention;

FIG. 6 is a schematic structural view of an elastic tongue-dorsum retraction device of the present invention that is fixed outside the lip by using silica gel;

FIG. 7 is a schematic structural view of an elastic tongue-dorsum retraction device of the present invention that is fixed outside the lip and adjustable by rotation;

FIG. 7-1 is an exploded view of FIG. 7;

FIG. 8 is a schematic structural view of an elastic tongue-dorsum retraction device of the present invention that is fixed outside the lip and adjustable by sliding;

FIG. 8-1 is an exploded view of FIG. 8;

FIG. 10-1 is a schematic structural view when an implant that can form an under-the-tongue-mucosa tunnel is implanted at the tongue;

FIG. 11-1 is a cross-sectional view of FIG. 11;

FIG. 11-2 is a schematic structural view when an under-the-tongue-mucosa tunnel of the present invention that includes a thin-walled tube-shaped object is on the tongue;

FIG. 13-1 is a schematic structural view of the fully-implantable connector of FIG. 13;

FIG. 14-1 is an enlarged view of part E of FIG. 14;

FIG. 14-2 is a schematic structural view of a magnetic fully-implantable connector of FIG. 14;

FIG. 14-3 is a D-D cross-sectional view of FIG. 14-2;

FIG. 14-4 is a view showing the position distribution of the magnetic fully-implantable connector of FIG. 14 that is implanted at the tongue dorsum;

FIG. 15-1 is a schematic structural view of FIG. 15 when a connection concave groove is used instead;

FIG. 15-2 is a schematic structural view of FIG. 15 when a connecting hook is used instead;

FIG. 15-3 is a schematic structural view of an elastic tongue-dorsum retraction device of the present invention where a distal end of an elastic retractor is directly adhered to the tongue dorsum;

FIG. 17-1 is a schematic structural view of a tunnel-type tongue dorsum connection mechanism of the present invention;

FIG. 17-2 is a top view of FIG. 17-1;

FIG. 17-3 is a cross-sectional view of FIG. 17-1;

FIG. 18-1 is a schematic structural view of an elastic retractor fixed by a transverse connection concave groove and longitudinal connection concave grooves of a tongue dorsum connection mechanism of the present invention;

FIG. 18-2 is a schematic structural view of a removable 4-groove thread-type tongue dorsum connection mechanism of the present invention, where in this embodiment, a connection convex step 12-2 at one end of a support 11 of the tongue dorsum connection mechanism 1 uses a removable thread connection structure, and the other end of the support 11 is an integrally manufactured non-removable 4-groove connection convex step 12-2; and such a structure can facilitate thread connection and disconnection;

FIG. 18-3 is an exploded view of FIG. 18-2;

FIG. 18-4 is a cross-sectional view of FIG. 18-2;

FIG. 18-5 is a schematic structural view of a removable 4-groove concave-convex engagement-type tongue dorsum connection mechanism of the present invention;

FIG. 18-6 is an exploded view of FIG. 18-5;

FIG. 18-7 is a cross-sectional view of FIG. 18-5;

FIG. 18-8 is a schematic structural view of an integrally formed 4-groove tongue dorsum connection mechanism of the present invention, where in this embodiment, four longitudinal connection concave grooves 12-1-2 are evenly distributed on the connection convex step 12-2 of the tongue dorsum connection mechanism 1;

FIG. 18-9 is a cross-sectional view of FIG. 18-8;

FIG. 18-10 is a schematic structural view of a tongue dorsum connection mechanism of the present invention being a 4-groove conical connection convex step, where in this embodiment, the connection convex step 12-2 has a conical structure, and four longitudinal connection concave grooves 12-1-2 are evenly distributed on the connection convex step 12-2 having a conical structure.

FIG. 18-11 is a schematic structural view of a 2-groove tongue dorsum connection mechanism of the present invention, where in this embodiment, two longitudinal connection concave grooves 12-1-2 are evenly distributed on the connection convex step 12-2 of the tongue dorsum connection mechanism 1;

FIG. 18-12 is a schematic structural view of a 3-groove tongue dorsum connection mechanism of the present invention, where in this embodiment, three longitudinal connection concave grooves 12-1-2 are evenly distributed on the connection convex step 12-2 of the tongue dorsum connection mechanism 1;

FIG. 18-13 is a schematic structural view of a 5-groove tongue dorsum connection mechanism of the present invention, where in this embodiment, five longitudinal connection concave grooves 12-1-2 are evenly distributed on the connection convex step 12-2 of the tongue dorsum connection mechanism 1;

FIG. 19-1 is a cross-sectional view of FIG. 19;

FIG. 19-2 is a view depicting the working principle of the three-stage elastic retractor of the present invention;

FIG. 20-1 is an F-F cross-sectional view of FIG. 20 at the tooth-side connection mechanism;

FIG. 20-2 is a G-G cross-sectional view of FIG. 20 at the elastic deformation mechanism;

FIG. 20-3 is a J-J cross-sectional view of FIG. 20 at the tongue dorsum connection mechanism;

FIG. 20-4 is a K-K cross-sectional view of FIG. 20;

FIG. 20-5 is a view depicting the working principle of the integral-type elastic retraction mechanism of the present invention;

FIG. 21-1 is a bottom view of FIG. 21;

FIG. 21-2 is a top view of FIG. 21;

FIG. 21-3 is a side view of FIG. 21-2;

FIG. 21-4 is a view depicting the working principle of the tripod-type tooth-side fastener that is fixed outside the lip of the present invention;

FIG. 22-1 is a front view of the tooth-side fastener of the present invention;

FIG. 22-2 is a cross-sectional view of FIG. 22-1;

FIG. 22-3 is a view depicting the working principle of the I-shaped tooth-side fastener of the present invention;

FIG. 23-1 is a schematic structural view of a head portion of the clamping pliers of FIG. 23;

FIG. 23-2 is a cross-sectional view of FIG. 23;

FIG. 23-3 is a schematic structural view of the clamping pliers of the present invention in an open state;

FIG. 23-4 is a schematic structural view of a head portion of the clamping pliers of FIG. 23-3;

FIG. 23-5 is a cross-sectional view of FIG. 23-3;

FIG. 23-6 is an exploded view of the clamping pliers of the present invention;

FIG. 23-7 is an exploded view of the clamping pliers of the present invention;

FIG. 23-8 is a schematic structural view of a right arm of the clamping pliers of the present invention;

FIG. 23-9 is an elevation view of FIG. 23-8;

FIG. 23-10 is a cross-sectional view of FIG. 23-8;

FIG. 23-11 is a schematic structural view of a left arm of the clamping pliers of the present invention;

FIG. 23-12 is an elevation view of FIG. 23-11;

FIG. 23-13 is a cross-sectional view of FIG. 23-11;

FIG. 23-14 is a schematic structural view of a self-lock positioning block of the clamping pliers of the present invention;

FIG. 23-15 is a three-dimensional schematic structural view of FIG. 23-14;

FIG. 23-16 is a view depicting the working principle of a connection convex step of a tongue dorsum connection mechanism is to be inserted into the clamping pliers of the present invention that are opened;

FIG. 23-17 is a view depicting the working principle after the connection convex steps of the tongue dorsum connection mechanism is inserted into the clamping pliers of the present invention of FIG. 23-16;

FIG. 23-18 is a view depicting the working principle of screwing the connection convex step of the tongue dorsum connection mechanism into a support of the tongue dorsum connection mechanism through thread connection by using the clamping pliers of the present invention;

FIG. 23-19 is a view depicting the working principle of removing the connection convex step of the tongue dorsum connection mechanism from the clamping pliers of the present invention after a self-lock switch is pressed;

FIG. 23-20 is an exploded view of the clamping pliers of the present invention where the restoring spring is mounted on a rotating shaft;

FIG. 23-21 is a three-dimensional schematic structural view of the right arm of FIG. 23-20, where in the embodiment shown by FIG. 23-20 and FIG. 23-21, the restoring spring 404 of the clamping pliers 400 is wound on the rotating shaft 403, with one end supported in a right restoring-spring mounting groove 401-2-3 of the right-arm tail 401-2, and the other end supported in a left restoring-spring mounting groove 402-2-3 of the left-arm tail 402-2;

FIG. 24 is a schematic structural view of installation pliers of the present invention;

FIG. 24-1 is a front view of the installation pliers of the present invention;

FIG. 24-2 is a left view of the installation pliers of the present invention;

FIG. 24-3 is a P-P cross-sectional view of FIG. 24-2;

FIG. 24-4 shows the first step of the working principle of the installation pliers of the present invention;

FIG. 24-5 shows the second step of the working principle of the installation pliers of the present invention;

FIG. 24-6 shows the third step of the working principle of the installation pliers of the present invention;

FIG. 24-7 shows the fourth step of the working principle of the installation pliers of the present invention;

In FIG. 24-4 to FIG. 24-7, the tongue dorsum connection mechanism 1, the elastic retractor 2, and the installation pliers 500 of the present invention are arranged in sequence from left to right. The tongue dorsum connection mechanism 1 includes a support 11 and an elastic-retractor tongue dorsum connection mechanism 12 connected to the elastic retractor, and the elastic-retractor tongue dorsum connection mechanism 12 includes connection convex steps 12-2, where the connection convex step 12-2 on the right side is thread-connected to the support 11. An upper end of the elastic retractor 2 has one tongue-side connection hole 21-1, and the tongue-side connection hole 21-1 can be sleeved over the connection convex step 12-2, so as to establish a removable connection between the elastic retractor 2 and the tongue dorsum connection mechanism 1. The installation pliers of the present invention include an opening end 501 and a handle end 502, the opening end 501 includes a pair of brackets 501-1, and a receiving space 501-2 formed by the brackets 501-1 can accommodate the connection convex step 12-2. After being stretched and enlarged, the tongue-side connection hole 21-1 on the elastic retractor 2 can be sleeved over a groove 501-1-1 of the bracket 501-1 of the installation pliers 500; then the installation pliers 500 with the elastic retractor 2 sleeved over its head portion is sleeved on the connection convex step 12-2, and the installation pliers are pulled out. Due to the existence of the connection convex step 12-2, the tongue-side connection hole 21-1 of the elastic retractor 2 shrinks, and is sleeved on the support 11, and embedded in the transverse connection concave groove 12-1-1 under the connection convex step 12-2 of the tongue dorsum connection mechanism 12, thereby connecting the elastic refractor 2 to the elastic-retractor tongue dorsum connection mechanism 12 on the tongue dorsum connection mechanism 1;

FIG. 24-8 is a view depicting the working principle of mounting the elastic retractor onto the tongue dorsum connection mechanism by using the installation pliers of the present invention;

FIG. 25-1 is a cross-sectional view of FIG. 25;

FIG. 25-2 is a partially enlarged view of part X of FIG. 25-1;

FIG. 25-3 is a schematic structural view of an integral-type elastic-retraction-mechanism line guide of the present invention that uses welding connection, where in this embodiment, a guide head portion of a line guiding rod 201 is connected to a mounting hook portion of the line guiding rod 201 by welding;

FIG. 25-4 is a partially enlarged view of part T of FIG. 25-3;

FIG. 25-5 is a schematic structural view of an integral-type elastic-retraction-mechanism line guide of the present invention that uses thread connection, where in this embodiment, the guide head portion of the line guiding rod 201 is connected to the mounting hook portion of the line guiding rod 201 by thread connection;

FIG. 25-6 is a partially enlarged view of part Z of FIG. 25-5;

FIG. 25-7 is a schematic structural view when a tooth-side connection hole on a tooth-side connection mechanism of an integral-type elastic retraction mechanism is disposed in a mounting hook of an elastic-retractor line guide of the present invention, where in this embodiment, first, the slide block 202 is made adjacent to a guide head 201-1, and a mounting hook 201-2 is exposed out of the slide block 202; then, a tooth-side connection hole 22-1 on a tooth-side connection mechanism 22 of the integral-type elastic retraction mechanism 212 is disposed in the mounting hook 201-2 of the integral-type elastic-retraction-mechanism line guide 200;

FIG. 25-8 is a schematic structural view when a mounting hook of an integral-type elastic-retraction-mechanism line guide of the present invention and a part of an end portion of an integral-type elastic retraction mechanism are wrapped by the slide block, where in this embodiment, after a tooth-side connection hole 22-1 on a tooth-side connection mechanism 22 of an integral-type elastic retraction mechanism 212 is disposed in a mounting hook 201-2 of the integral-type elastic-retraction-mechanism line guide 200, and the slide block 202 is slid toward the mounting hook 201-2, so as to completely wrap the mounting hook 201-2 and the part of the tooth-side connection hole 22-1 on the tooth-side connection mechanism 22 of the integral-type elastic retraction mechanism 212 that is disposed in the mounting hook 201-2, thereby completing the preparation work before line guiding using the elastic-retractor line guide 200;

FIG. 27-1 is a schematic structural view of a U-shaped tongue dorsum connection mechanism of the present invention;

FIG. 27-2 is a schematic structural view of an elliptical ring-shaped tongue dorsum connection mechanism of the present invention;

FIG. 27-3 is a schematic structural view of a circular ring-shaped tongue dorsum connection mechanism of the present invention;

FIG. 27-4 is a schematic structural view of a tongue dorsum connection mechanism with connection concave grooves of the present invention;

FIG. 27-5 is a schematic structural view of a tongue dorsum connection mechanism with connecting hooks of the present invention;

FIG. 27-6 is a schematic structural view of a tongue dorsum connection mechanism with thread connection-type connecting hooks of the present invention;

FIG. 27-7 is a schematic structural view of a connection concave groove a tongue dorsum connection mechanism of the present invention and a matching tongue-side connection convex step on an elastic retractor;

FIG. 27-8 is a schematic structural view of a tongue dorsum connection mechanism with connecting rings of the present invention;

FIG. 27-9 is a schematic structural view of a tongue dorsum connection mechanism of the present invention that has a connecting ring mounted on a strip-shaped support;

FIG. 28-1 is a schematic structural view of a dual-hook elastic retractor of the present invention;

FIG. 28-2 is a schematic structural view of a dual-hook elastic retractor of the present invention that includes a spring;

FIG. 28-3 is a schematic structural view of an elastic retractor with a connecting line of the present invention;

FIG. 28-4 is a schematic structural view of a four-hook elastic retractor of the present invention that includes a spring;

FIG. 28-5 is a schematic structural view of a three-hook Y-shaped elastic refractor of the present invention;

Figure 1:
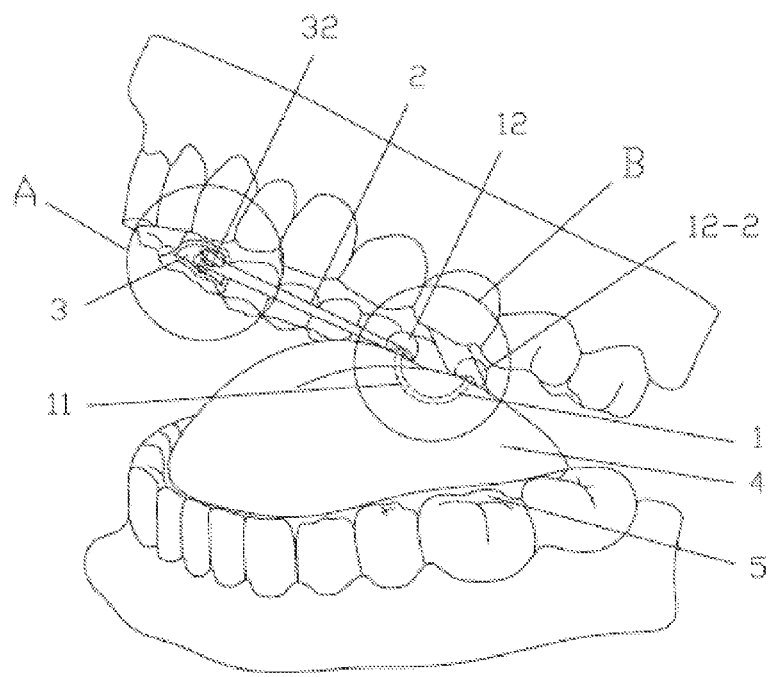
FIG. 1 is a schematic structural view of an elastic tongue-dorsum retraction device of the present invention that is fixed to the inner side of upper teeth.
Figures 1, 2:
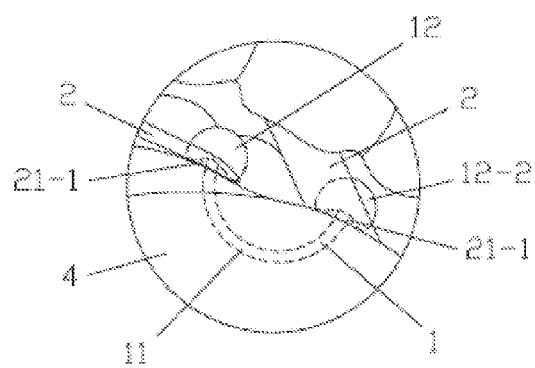

FIG. 29-1 is a schematic structural view of a tooth-side fastener and an elastic retractor of the present invention, where the tooth-side fastener is magnetically connected to the elastic retractor;

FIG. 29-2 is an assembled view of FIG. 29-1;

FIG. 30-1 is a schematic structural view of a manner of connection between an elastic retractor and a tooth-side fastener of the present invention;

FIG. 30-2 is an exploded view of FIG. 30-1;

FIG. 31-1 is a schematic structural view of a manner of connection between an elastic retractor and a tooth-side fastener of the present invention;

FIG. 31-2 is an exploded view of FIG. 31-1;

FIG. 32-1 is a schematic structural view of a manner of connection between an elastic retractor and a tooth-side fastener of the present invention;

FIG. 32-2 is an exploded view of FIG. 32-1; and

Figure 33:
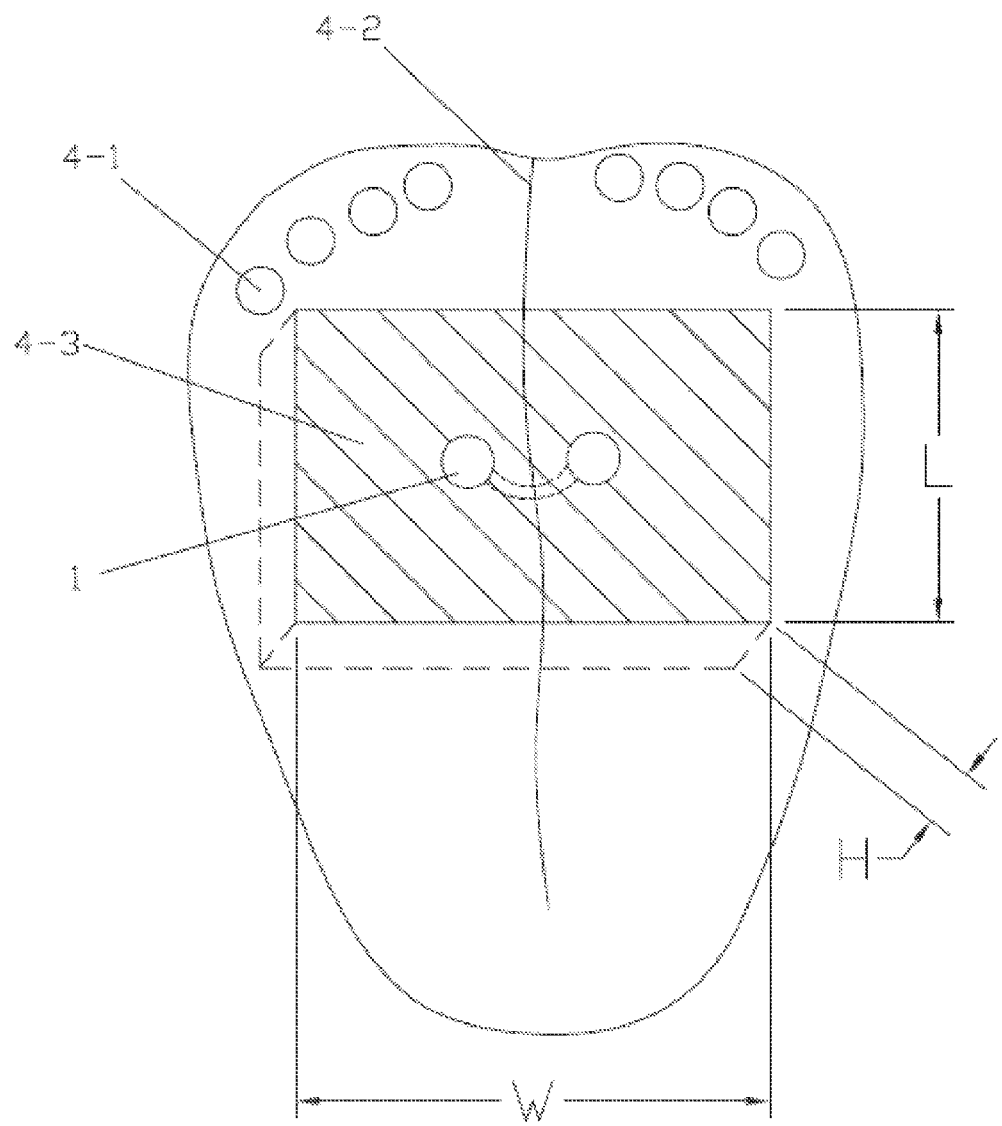

FIG. 33 is a view showing distribution of an area for implanting a tongue dorsum connection mechanism of an elastic tongue-dorsum retraction device of the present invention.

THE MEANINGS OF THE SERIAL NUMBERS IN THE ABOVE DRAWINGS ARE AS FOLLOWS 1. tongue dorsum connection mechanism; 2. elastic retractor; 3. tooth-side fastener; 4. tongue; 5. teeth; 6. lip; 7. airway at the glossopharyngeal portion; 8. gums; 9. coil spring. 4-1. circumvallate papillae of the tongue; 4-2. midline of the tongue; 4-3. tongue dorsum area for an implanted tongue dorsum connection mechanism. L. length of the tongue dorsum area for implanting the tongue dorsum connection mechanism; W. width of the tongue dorsum area for implanting the tongue dorsum connection mechanism; H. height of the tongue dorsum area for implanting the tongue dorsum connection mechanism.

On the Tongue Dorsum Connection Mechanism 1:

100. tunnel-type retraction connection mechanism; 101. connector fixed to the tongue; 102. fully-implantable connector; 103. semi-implantable connector; 104. mucosa-surface-fixed-type connector; 105. convex step for preventing displacement of the implanted connector; 106. through hole for preventing displacement of the implanted connector.

100-1. under-the-tongue-mucosa epithelialized tunnel; 100-2. implant that can form an under-the-tongue-mucosa tunnel; 100-3. under-the-tongue-mucosa tunnel that includes a thin-walled tube-shaped implant; 100-4. thin-walled tube-shaped implant.

100-4-1. positioning convex step; 100-4-2. smooth surface at the bottom of the positioning convex step that matches the surface of the tongue mucosa; 100-4-3. center hole of the thin-walled tube-shaped implant.

102-1. flat object. 1021-1. magnetic unit; 1021-2. base body.

104-1. support base of the mucosa-surface-fixed-type connector; 104-2. connection mechanism, which is connected to the elastic retractor, on the mucosa-surface-fixed-type connector; 1042-1. connection concave groove; 1042-2. connection convex step; 1042-3. connecting hook.

11. support; 11-5. concave-convex engagement mounting convex step on the support; 11-6. slot hole on the support; 11-7. connecting bolt on the support;

12. elastic-retractor tongue dorsum connection mechanism connected to the elastic retractor; 12-1. connection concave groove; 12-2. connection convex step; 12-3. connecting hook. 12-4. conical transition mechanism for alleviating irritation of edges to the mucosa on the surface of the tongue; 12-5. concave-convex engagement mounting convex groove on the connection convex step; 12-6. connecting ring; 12-7. connecting nut on the connection convex step. 12-1-1. transverse connection concave groove; 12-1-2. longitudinal connection concave groove.

d12. diameter of the conical transition mechanism close to the elastic-retractor tongue dorsum connection mechanism; d11. diameter of the conical transition mechanism close to the support; β angle between two smooth surfaces of the positioning convex steps at two ends of the tunnel-type tongue dorsum connection mechanism.

On the Elastic Retractor 2:

20. elastic deformation mechanism; 21. tongue-side connection mechanism, which is connected to the tongue dorsum connection mechanism, on the elastic retractor; 22. tooth-side connection mechanism, which is connected to the tooth-side fastener, on the elastic retractor; 212. integral-type elastic retraction mechanism.

21-1. tongue-side connection hole; 21-2. tongue-side connection convex step; 21-3. tongue-side connecting hook; 21-4. tongue-side connecting line; 21-5. tongue-side connection end portion; 22-1. tooth-side connection hole; 22-2. tooth-side connection convex step; 22-3. tooth-side connecting hook; 22-4. tooth-side connecting line.

21-1-1. protruding edge on the tongue-side connection hole; 22-1-1. protruding edge on the tooth-side connection hole.

S1. tongue-side connection through hole formed on the tongue-side end of the elastic retractor; S2. tongue-side connection through hole formed on the tongue-side end of the elastic retractor; S3. tongue-side connection through hole formed on the tongue-side end of the elastic retractor. Y1. tooth-side connection through hole formed on the tooth-side end of the elastic retractor; Y2. tooth-side connection through hole formed on the tooth-side end of the elastic retractor; Y3. tooth-side connection through hole formed on the tooth-side end of the elastic retractor.

On the Tooth-Side Fastener 3:

31. support bracket; 32. elastic-retractor tooth-side connection mechanism connected to the elastic retractor; 33. tooth-side fastening mechanism fixed to the tooth-side fastener; 34. retraction-force adjustment mechanism;

31-1. tooth-side fixing support bracket; 31-2. dental bone nail-type fixing support bracket; 31-3. dental sleeve-type fixing support bracket; 31-4. support bracket fixed outside the lip. 32-1. positioning concave groove of the tooth-side fastener; 32-2. positioning convex step of the tooth-side fastener; 32-3. positioning hook of the tooth-side fastener; 33-1. housing having a radian matching the surface of teeth on the tooth-side fastening mechanism; 34-1. rotation mechanism; 34-2. sliding mechanism;

31-1-1. tooth-side adhesion surface of the tooth-side fixing support bracket; 31-1-2. support base of the tooth-side fixing support bracket; 31-2-1. tooth groove on a dental sleeve-fixing type tooth-side fastener; 31-4-1. support bracket fixed outside the maxilla lip; 31-4-2. support bracket fixed outside the mandible lip; 31-4-3. support bracket at the lip corner; 33-1-1. glue accommodating hole provided on the housing; 3411. rotating shaft; 3411-1. positioning polygon on the rotating shaft; 3411-2. restoring spring; 3411-3. positioning nut; 3411-4. elastic-retractor fixing groove; 3411-5. knob; 3412. rotating-shaft mounting and positioning groove; 3412-1. positioning-polygon groove; 3412-2. restoring-spring mounting hole; 3412-3. positioning-nut mounting hole; 3421. slide block of the sliding mechanism; 3422. positioning block of the sliding mechanism; 3421-1. positioning tooth groove of the slide block; 3421-2. handle of the slide block; 3421-3. slide-block bracket.

γ. angle between the support bracket 31-4-1 fixed outside the maxilla lip and the support bracket 31-4-2 fixed outside the mandible lip; ϵ. angle between the support bracket 31-4-1 fixed outside the maxilla lip and the support bracket 31-4-3 at the lip corner; θ. angle between the support bracket 31-4-2 fixed outside the mandible lip and the support bracket 31-4-3 at the lip corner.

200. line guide; 400. clamping pliers; 500. installation pliers.

On the Line Guide 200:

200. integral-type elastic-refraction-mechanism line guide; 212. integral-type elastic retraction mechanism.

201. line guiding rod; 202. slide block.

201-1. guide head; 201-2. mounting hook; 201-3. limiting groove;

202-1. sliding convex step.

On the Clamping Pliers 400:

400. clamping pliers; 401. right arm; 402. left arm; 403. rotating shaft; 404. restoring spring; 405. self-lock mechanism; 406. mounting groove of the self-lock mechanism; 407. anti-slip pattern or anti-slip groove.

401-1. right clamp head; 401-2. right-arm tail; 401-3. right-arm rotating-shaft mounting convex step.

402-1. left clamp head; 402-2. left-arm tail; 402-3. left-arm rotating-shaft mounting convex step.

405-1. pin; 405-2. torsion spring; 405-3. self-lock positioning block.

401-1-1. right working groove; 401-1-2. right rotation restricting convex step; 401-1-3. right anti-detachment restricting convex step; 401-1-4. positioning and guiding groove; 401-2-1. pin hole; 401-2-2. unlocking groove; 401-2-3. right restoring-spring mounting groove; 401-3-1. through hole on the right rotating-shaft mounting convex step.

402-1-1. left working groove; 402-1-2. left rotation restricting convex step; 402-1-3. left anti-detachment restricting convex step; 402-1-4. positioning and guiding block; 402-2-1. positioning convex step; 402-2-3. left restoring-spring mounting groove; 402-3-1. through hole on the left rotating-shaft mounting convex step.

405-3-1. lock tooth; 405-3-2. self-lock switch; 405-3-3. mounting through hole; 405-3-4. torsion-spring mounting groove.

On the Installation Pliers 500:

501. opening end; 502. handle end. 501-1. bracket; 501-2. receiving space; 502-1. anti-slip groove, anti-slip fin or anti-slip pattern; 501-1-1. groove.

d501. distance between brackets.

DETAILED DESCRIPTION OF THE INVENTION

The principle of the present invention for treating OSAHS lies in that: by using teeth, gums, or positions outside the maxilla and mandible lips as supporting points, a tooth-side fastener 3 is fixed to teeth or gums, or outside the lip; a tongue dorsum connection mechanism 1 is disposed on the tongue; one end of an elastic retractor 2 is connected to the tooth-side fastener 3, and the other end of the elastic retractor 2 is connected to the tongue dorsum connection mechanism 1; the elastic retractor 2 forms an elastic refraction force between the tongue dorsum connection mechanism 1 and the tooth-side fastener 3 to pull up the sagging tongue, so as to enlarge the space of the airway at the glossopharyngeal portion, thereby treating snoring and OSAHS that are caused by sagging and collapse of the tongue, as shown in FIG. 1.

Since the elastic retractor 2 has quite good elasticity, elastic retraction can be achieved between the tooth-side fastener 3 and the tongue dorsum connection mechanism 1 to provide enough freedom of movement for the tongue. In this way, when the tongue root is properly pulled up without excessively affecting movement of the tongue tip and the tongue body, not only the airway at the glossopharyngeal portion is enlarged to achieve the objective of treating OSAHS, but also a good movement function of the tongue tip portion is maintained, which ensures a clear language function and an adequate swallowing function and provides good comfort. When the tongue-side fastener 3 is provided with a retraction-force adjustment mechanism 34, the magnitude of the retraction force to the tongue dorsum portion can be adjusted according to the actual need of a patient, which further improves comfort and efficacy. In addition, when the tooth-side fastener 3 is fixed to the inner side of teeth, a good invisible effect is provided, and the elastic tongue-dorsum retraction device of the present invention is invisible unless the patient breathes through the mouth, thereby greatly alleviating the psychological stress of the patient and relatives of the patient.

Embodiment 1: Elastic Tongue-Dorsum Retraction Device of the Present Invention that is Fixed to the Inner Side of Teeth in an Invisible Manner Referring to FIG. 1, this embodiment shows an elastic tongue-dorsum retraction device of the present invention that is fixed to the inner side of teeth in an invisible manner.

Figures 1, 2, 3:
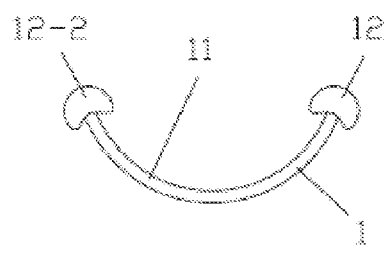

Referring to FIG. 1-3, the tongue dorsum connection mechanism 1 is formed by a support 11 and an elastic-retractor tongue dorsum connection mechanism 12. The support 11 is an arc-shaped metal wire made of medical titanium metal. Two ends of the support 11 are each provided with a connection convex step 12-2. The size of the connection convex step 12-2 is greater than the diameter of the arc-shaped metal wire, which facilitates mounting and fixation of an elastic retractor 2. The connection convex steps 12-2 form the elastic-retractor tongue dorsum connection mechanism 12 of the tongue dorsum connection mechanism 1.

The connection convex steps 12-2 may be fixed to end portions of the support 11 by thread connection, concave-convex engagement, interference fit, or adhesion using an adhesive; alternatively, the connection convex steps 12-2 and the support 11 may be made of a same piece of metal by mechanical processing. For example, in this embodiment, the connection convex steps 12-2 and the support 11 are made of a same piece of metal by mechanical processing.

Referring to FIG. 1-4, the elastic retractor 2 is made of a medical elastic film, for example, a medical silica gel film or a medical latex film is selected. The film has a thickness of 0.01 mm to 3 mm, and generally a medical latex film having a thickness of 0.10 mm is selected. The elastic retractor 2 has a rectangular strip-shaped structure, and is provided with a tongue-side connection hole 21-1 and a tooth-side connection hole 22-1. The tongue-side connection hole 21-1 may be mounted and fixed to the connection convex step 12-2 or removed from the connection convex step 12-2. The tongue-side connection hole 21-1 forms a tongue-side connection mechanism 21 on the elastic retractor 2, which is connected to the tongue dorsum connection mechanism 1, as shown in FIG. 1-2 and FIG. 1-7. The tooth-side connection hole 22-1 may be mounted and fixed to a positioning convex step 32-2 of a tooth-side fastener 3 or removed from the positioning convex step 32-2 of the tooth-side fastener 3. The tooth-side connection hole 22-1 forms a tooth-side connection mechanism 22 on the elastic retractor 2, which is connected to the tooth-side fastener 3, as shown in FIG. 1-1 and FIG. 1-6.

Referring to FIG. 1-5, the tooth-side fastener 3 is formed by a support bracket 31, an elastic-retractor tooth-side connection mechanism 32 and a tooth-side fastening mechanism 33. The support bracket 31 is a tooth-side fixing support bracket 31-1. The tooth-side fixing support bracket 31-1 is formed by a tooth-side adhesion surface 31-1-1 and a support base 31-1-2. The tooth-side adhesion surface 31-1-1 has a shape matching that of the inner side surface of upper teeth, and can be fixed to the inner surface of upper teeth by adhesion using a dental adhesive. The tooth-side adhesion surface 31-1-1 forms the tooth-side fastening mechanism 33 of the tooth-side fastener, as shown in FIG. 1-6. The elastic-retractor tooth-side connection mechanism 32 is a positioning convex step 32-2. The positioning convex step 32-2 is connected to the support base 31-1-2. The tooth-side connection hole 22-1 on the elastic retractor 2 may be mounted and fixed to the positioning convex step 32-2 or removed from the positioning convex step 32-2, as shown in FIG. 1-1 and FIG. 1-6.

During clinical use, first, the tongue dorsum connection mechanism 1 is implanted at the tongue dorsum through a minimally invasive surgery, so that the support 11 of the tongue dorsum connection mechanism 1 is implanted under the mucosa of the tongue dorsum, and the elastic-retractor tongue dorsum connection mechanism 12 of the tongue dorsum connection mechanism 1 is exposed out of the mucosa of the tongue dorsum. After 15 days to 45 days after the surgery, the support 11 can be firmly fixed under the mucosa of the tongue dorsum, and at this time, the sagging tongue can be pulled up by pulling the elastic-retractor tongue dorsum connection mechanism 12 that is exposed out of the mucosa of the tongue dorsum, as shown in FIG. 1-7.

Secondly, two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is selected as an adhesive fixing point of the tooth-side fastener 3. Definitely, other upper teeth or a lower tooth may also be selected as the adhesive fixing point of the tooth-side fastener 3 according to the actual condition of the patient, as shown in FIG. 1-8.

Before sleep, one end of the elastic retractor 2 is removably connected to the tooth-side fastener 3, and the other end of the elastic retractor 2 is removably connected to the elastic-retractor tongue dorsum connection mechanism 12 of the tongue dorsum connection mechanism 1; the elastic retractor 2 forms an elastic refraction force between the tongue dorsum connection mechanism 1 and the tooth-side fastener 3 to pull up the sagging tongue, so as to enlarge the airway at the glossopharyngeal portion, thereby treating snoring and OSAHS that are caused by sagging and collapse of the tongue, as shown in FIG. 1. A specific connection manner is as follows:

The tongue-side connection hole 21-1 on the elastic retractor 2 having a rectangular strip-shaped structure is fixed to the connection convex step 12-2 of the tongue dorsum connection mechanism, that is, connection of the elastic retractor 2 to the tongue dorsum connection mechanism 1 is completed, as shown in FIG. 1-7. Then, the tooth-side connection hole 22-1 on the elastic retractor 2 is fixed to the positioning convex step 32-2 on the tooth-side fastener 3, that is, a connection between the elastic retractor 2 and the tooth-side fastener 3 is formed, as shown in FIG. 1-6.

Since the elastic retractor 2 elastically retracts the tongue dorsum connection mechanism 1, the movement of the tongue is not affected when the sagging tongue is properly pulled up; therefore, not only the airway at the glossopharyngeal portion is enlarged, but also good comfort is provided.

In addition, the two tooth-side fasteners 3 of the elastic tongue-dorsum retraction device of the present invention are respectively mounted and fixed to the inner side of a left upper tooth and a right upper tooth, which provides an invisible effect. If the patient does not open the mouth during sleep, the elastic tongue-dorsum refraction device of the present invention that has been disposed in the oral cavity is invisible, which greatly alleviates the psychological stress of the patient and relatives of the patient. The elastic tongue-dorsum retraction device of the present invention that is fixed to the inner side of teeth in an invisible manner is not only easy to mount and convenient to use, clean and sterilize, but also is pleasing in appearance and comfortable to use.

Embodiment 2: Elastic Tongue-Dorsum Retraction Device of the Present Invention that is Adhesively Fixed to the Outer Side of Teeth Referring to FIG. 2, a difference between this embodiment and Embodiment 1 lies in that: in Embodiment 1, the tooth-side fasteners 3 are adhesively fixed to the inner side of upper teeth; while in this embodiment, two tooth-side fasteners 3 are respectively fixed to the outer side of one upper tooth on the left and the outer side of one upper tooth on the right. Generally, the fourth upper tooth counted leftward starting from incisors or the fourth upper tooth counted rightward starting from incisors is selected as an adhesive fixing point of the tooth-side fastener 3. Definitely, other upper teeth may also be selected as the adhesive fixing point of the tooth-side fastener 3 according to the actual condition of the patient. Such a method is advantageous in that the elastic retractor 2 can be mounted on the tooth-side fastener 3 more conveniently, but the tooth-side fastener 3 may sometimes be exposed outside the lip, affecting the appearance.

Another difference lies in that, the tooth-side adhesion surface 31-1-1 has a shape matching that of the outer surface of upper teeth, and can be fixed to the outer surface of upper teeth by adhesion using a dental adhesive.

Embodiment 3: Elastic Tongue-Dorsum Retraction Device of the Present Invention that is Fixed to the Inner Side of Gums by Using a Dental Nail Referring to FIG. 3, a difference between this embodiment and Embodiment 1 lies in that: in Embodiment 1, the tooth-side fasteners 3 are fixed to the teeth by adhesion using a dental adhesive; while in this embodiment, the tooth-side fastener 3 is a dental nail-type structure, and the tooth-side fastener 3 is fixed to the inner side of the upper gums through a dental bone nail-type fixing support bracket 31-2 on the tooth-side fastener 3.

In the structure of the tooth-side fastener 3, the dental bone nail-type fixing support bracket 31-2 that can be fixed to gums is used. One of the tooth-side fasteners 3 is fixed to the inner side of the upper gums between the fourth tooth and the fifth tooth counted leftward starting from incisors through the dental bone nail-type fixing support bracket 31-2, and the other tooth-side fastener 3 is fixed to the inner side of the upper gums between the fourth tooth and the fifth tooth counted rightward starting from incisors through the dental bone nail-type fixing support bracket 31-2, as shown in FIG. 3.

Referring to FIG. 3-1, the tooth-side fastener 3 is formed by a support bracket 31, an elastic-retractor tooth-side connection mechanism 32 and a tooth-side fastening mechanism 33. The support bracket 31 is a dental bone nail-type fixing support bracket 31-2, and has a structure similar to that of a dental anchorage nail. The elastic-retractor tooth-side connection mechanism 32 is a positioning convex step 32-2. The tooth-side fastening mechanism 33 is a titanium metal screw 33-1 that can be fixed to gums. The tooth-side fastener 3 may be fixed to gums through the titanium metal screw 33-1, and the tooth-side connection hole 22-1 of the elastic retractor 2 may be sleeved over a groove formed between the positioning convex step 32-2 and the support bracket 31, so as to establish a fixed connection relationship between the tooth-side fastener 3 and the elastic retractor 2.

As a change to this embodiment, the tongue dorsum connection mechanism 1 implanted at the tongue dorsum may be changed from the arc-shaped support to an elliptical ring-shaped support bracket, as shown in FIG. 3-2. When an elliptical ring-shaped support bracket is used as the tongue dorsum connection mechanism 1, a part of the elliptical ring-shaped support bracket is implanted under the mucosa of the tongue dorsum to serve as the support 11 of the tongue dorsum connection mechanism 1. The other part of the elliptical ring-shaped support bracket is exposed out of the mucosa of the tongue dorsum to serve as the elastic-retractor tongue dorsum connection mechanism 12. After the elastic retractor 2 is passed through the elliptical ring-shaped support bracket that is exposed out of the mucosa of the tongue dorsum, a positioning hole 22-1 at one end of the elastic refractor 2 is sleeved over the tooth-side fastener 3 on the gums on the left side of upper teeth, and the positioning hole 22-1 at the other end of the elastic refractor 2 is sleeved over the tooth-side fastener 3 on the gums on the right side of upper teeth, so as to achieve elastic refraction of the elastic retractor 2 to the tongue dorsum connection mechanism 1, where only one elastic retractor 2 is used in this elastic tongue retraction method, as shown in FIG. 3-2.

Embodiment 4: Elastic Tongue-Dorsum Retraction Device of the Present Invention that is Fixed to the Outer Side of Gums by Using a Dental Nail Referring to FIG. 4, a difference between this embodiment and Embodiment 3 lies in that: one of the tooth-side fasteners 3 is fixed to the outer side of the upper gums between the fourth tooth and the fifth tooth counted leftward starting from incisors through the dental bone nail-type fixing support bracket 31-2, and the other tooth-side fastener 3 is fixed to the outer side of the upper gums between the fourth tooth and the fifth tooth counted rightward starting from incisors through the dental bone nail-type fixing support bracket 31-2. The tongue dorsum connection mechanism 1 is fixed to the tongue dorsum portion in a semi-implanted manner, so that the support 11 on the tongue dorsum connection mechanism 1 is implanted under the tongue mucosa, and the elastic-retractor tongue dorsum connection mechanism 12 of the tongue dorsum connection mechanism 1 is exposed out of the mucosa of the tongue dorsum; one end of the elastic refractor 2 is connected to the tooth-side fastener 3, and the other end of the elastic retractor 2 is removably connected to the elastic-retractor tongue dorsum connection mechanism 12 of the tongue dorsum connection mechanism 1; the elastic retractor 2 forms an elastic retraction force between the tongue dorsum connection mechanism 1 and the tooth-side fastener 3 to pull up the sagging tongue, so as to enlarge the space of the airway at the glossopharyngeal portion, thereby treating OSAHS caused by sagging and collapse of the tongue.

Embodiment 5: Dental Sleeve-Fixing Type Elastic Tongue-Dorsum Retraction Device of the Present Invention Referring to FIG. 5, a difference between this embodiment and Embodiment 1 lies in that: in Embodiment 1, the tooth-side fastener is a tooth-side fastener 3 that is fixed to the inner side of teeth, and is adhesively fixed to the inner side of upper teeth; while in this embodiment, a dental sleeve-fixing type tooth-side fastener 3. The support bracket 31 of the tooth-side fastener, which is the dental sleeve-fixing type tooth-side fastener 3, has a tooth groove 31-2-1 having a shape matching arrangement of upper teeth, and the tooth groove 31-2-1 serves as the tooth-side fastening mechanism 33 of the tooth-side fastener, so that the tooth-side fastener 3 can be removably mounted on upper teeth.

The dental sleeve-fixing type tooth-side fastener 3 may be made of a medical shape memory polymer material. First, the dental sleeve-fixing type tooth-side fastener 3 made of a medical shape memory polymer material is soaked in hot water at about 45° C., and is then bitten by teeth. When the temperature drops to the body temperature, the shape memory polymer material is automatically shape-set, so that a tooth groove 31-2-1 having a shape matching arrangement of upper teeth is formed. The tooth groove 31-2-1 may serve as the tooth-side fastening mechanism 33, and is used for fixing the tooth-side fastener 3 by using upper teeth as supporting points.

In this embodiment, the elastic retractor 2 is made of a medical elastic film, a tongue-side connection end of the elastic refractor 2 is directly mounted and fixed to an dental sleeve-type fixing support bracket 31-3, the tongue-side connection end is provided with a tongue-side connection hole 21-1, and the tongue-side connection hole 21-1 can be removably fixed to the elastic-retractor tongue dorsum connection mechanism 12 of the tongue dorsum connection mechanism 1.

Embodiment 6: Elastic Tongue-Dorsum Retraction Device of the Present Invention that is Fixed Outside the Lip by Using Silica Gel Referring to FIG. 6, a difference between this embodiment and Embodiment 1 lies in that: in this embodiment, a tooth-side fastener 3 that is fixed outside the lip and integrally made of medical silica gel is used as the tooth-side fastener 3.

The tooth-side fastener 3 is integrally made of medical silicon rubber, and includes a support bracket 31, an elastic-retractor tooth-side connection mechanism 32 and a tooth-side fastening mechanism 33. The support bracket 31 is a support bracket 31-4 fixed outside the lip. The support bracket 31-4 fixed outside the lip is a force-bearing elliptical-shaped silica gel ring, and is not only equivalent to the support bracket 31 of the tooth-side fastener 3, but also may be disposed outside the lip to serve as the tooth-side fastening mechanism 33 by using the oral cavity as a supporting point. A transition area with through holes is provided between the force-bearing elliptical-shaped silica gel ring and the silica gel film strip that serves as the elastic retractor 2. The support bracket 31 and the elastic retractor 2 are connected by the transition area to form the elastic-retractor tooth-side connection mechanism 32. The elastic retractor 2 and the support bracket 31-4 fixed outside the lip are connected together by the elastic-retractor tooth-side connection mechanism 32. The other end of the elastic refractor 2 is provided with a tongue-side connection hole 21-1 connected to the tongue dorsum connection mechanism 1.

The tooth-side fastener 3 is disposed outside the lip and uses the oral cavity as the supporting point, and by means of refraction of the elastic retractor 2 to the tongue dorsum connection mechanism 1, the sagging tongue is pulled up to enlarge the space of the airway at the glossopharyngeal portion, thereby treating OSAHS caused by sagging and collapse of the tongue.

Embodiment 7: Elastic Tongue-Dorsum Retraction Device of the Present Invention that is Fixed Outside the Lip and Adjustable by Rotation Referring to FIG. 7, a difference between this embodiment and Embodiment 6 lies in that: in this embodiment, the tooth-side fastener 3 is provided with a retraction-force adjustment mechanism 34. The retraction-force adjustment mechanism 34 uses a rotary adjustment manner, and includes a rotation mechanism 34-1.

The rotation mechanism 34-1 is formed by a rotating shaft 3411 and a rotating-shaft mounting and positioning groove 3412.

Figures 1, 2, 3, 4:
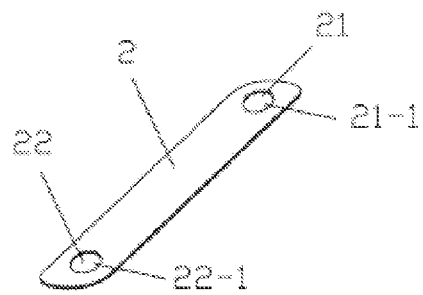
Figures 1, 2, 3, 4, 5:
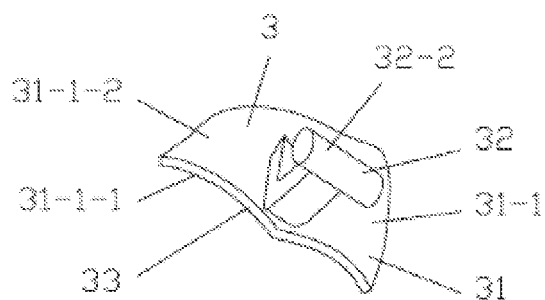
Figures 1, 2, 3, 4, 5, 6:
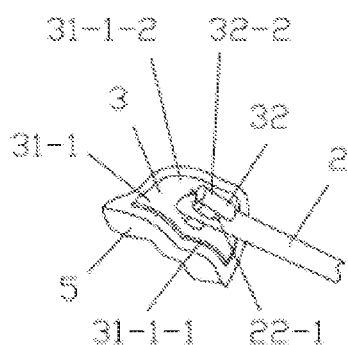
Figures 1, 2, 3, 4, 5, 6, 7:
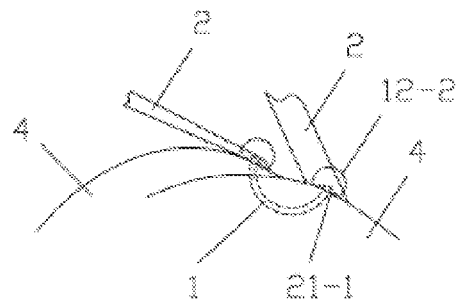

The rotating shaft 3411 is provided with a positioning polygon 3411-1, a restoring spring 3411-2, a positioning nut 3411-3, an elastic-refractor fixing groove 3411-4, and a knob 3411-5, as shown in FIG. 7-1.

The rotating-shaft mounting and positioning groove 3412 is provided with a positioning-polygon groove 3412-1, a restoring-spring mounting hole 3412-2, and a positioning-nut mounting hole 3412-3.

The rotating shaft 3411 is mounted in the rotating-shaft mounting and positioning groove 3412, the restoring spring 3411-2 is mounted in the restoring-spring mounting hole 3412-2, and the restoring spring 3411-2 is fixed to a distal end of the rotating shaft 3411 by using the positioning nut 3411-3. The tongue-side connection end of the elastic retractor 2 is fixed to the elastic-retractor fixing groove 3411-4 of the rotating shaft 3411.

When a force is applied to pull the knob 3411-5 toward the outside, the restoring spring 3411-2 deforms due to compression, and the positioning polygon 3411-1 is released from restriction of the positioning-polygon groove 3412-1, so that the rotating shaft 3411 can be rotated. Since the elastic retractor 2 is connected to the elastic-retractor fixing groove 3411-4, the knob 3411-5 is rotated clockwise to enable the rotating shaft 3411 to rotate clockwise, so that the elastic retractor 2 can be pulled up, to increase the retraction force of the elastic retractor 2. On the contrary, the knob 3411-5 is rotated anticlockwise to enable the rotating shaft 3411 to rotate anticlockwise, so that the elastic retractor 2 can be loosened, to reduce the retraction force of the elastic retractor 2. After the retraction force is adjusted to proper magnitude, the knob 3411-5 is loosened, and under the effect of an elastic force of the restoring spring 3411-2, the positioning polygon 3411-1 slides into the positioning-polygon groove 3412-1 to provide a function of restricting rotation of the rotating shaft 3411. The knob 3411-5 of the refraction-force adjustment mechanism 34 is disposed outside the oral cavity, thereby facilitating manual adjustment.

Embodiment 8: Elastic Tongue-Dorsum Retraction Device of the Present Invention that is Fixed Outside the Lip and Adjustable by Sliding Referring to FIG. 8, a difference between this embodiment and Embodiment 7 lies in that: the tooth-side fastener 3 is provided with a retraction-force adjustment mechanism 34. The retraction-force adjustment mechanism 34 uses a sliding adjustment manner, and includes a sliding mechanism 34-2.

The sliding mechanism 34-2 is formed by a slide block 3421 and a positioning block 3422.

Figures 1, 2, 3, 4, 5, 6, 7, 8:
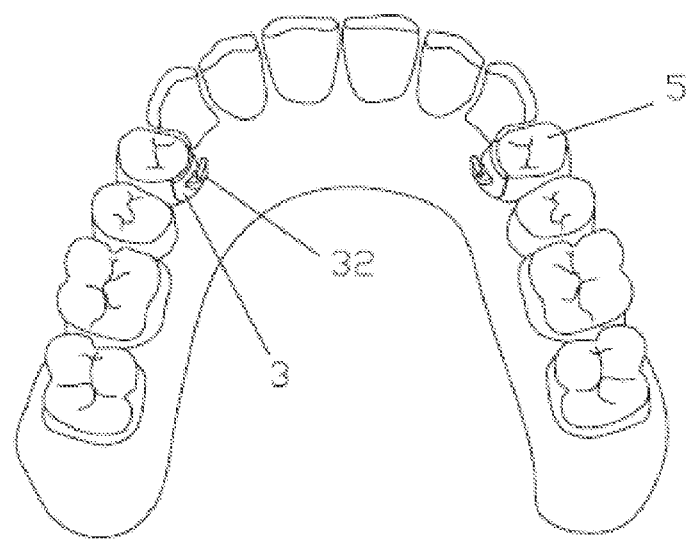
Figure 2:
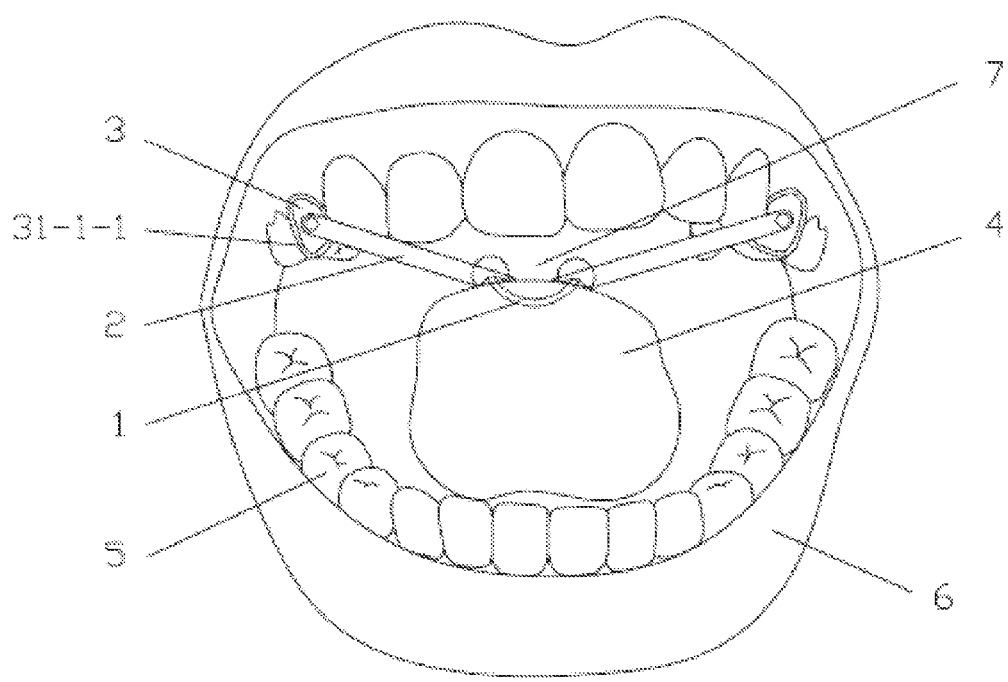
Figure 3:
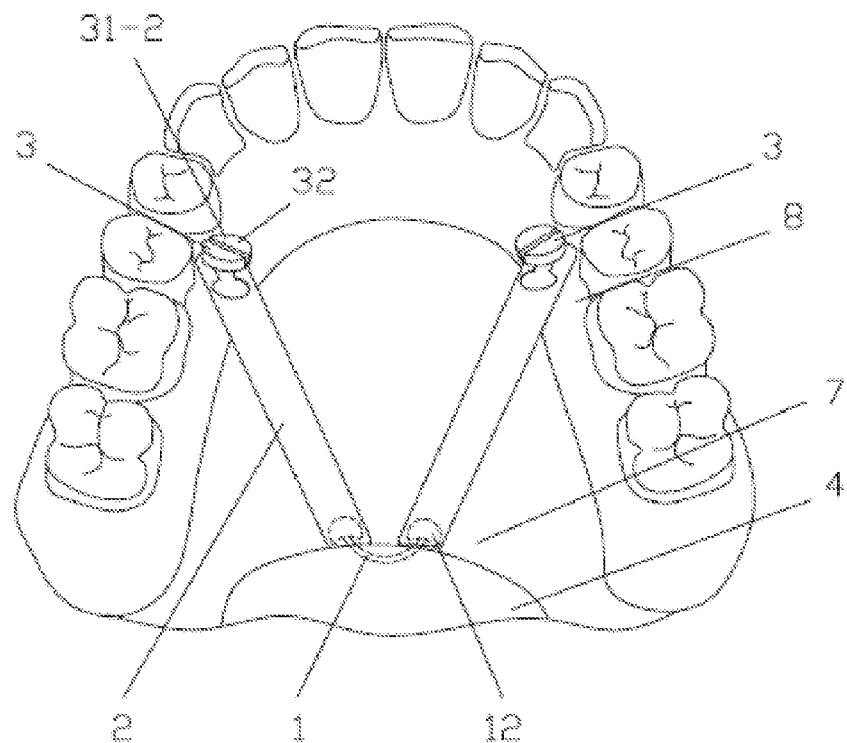
Figures 1, 3:
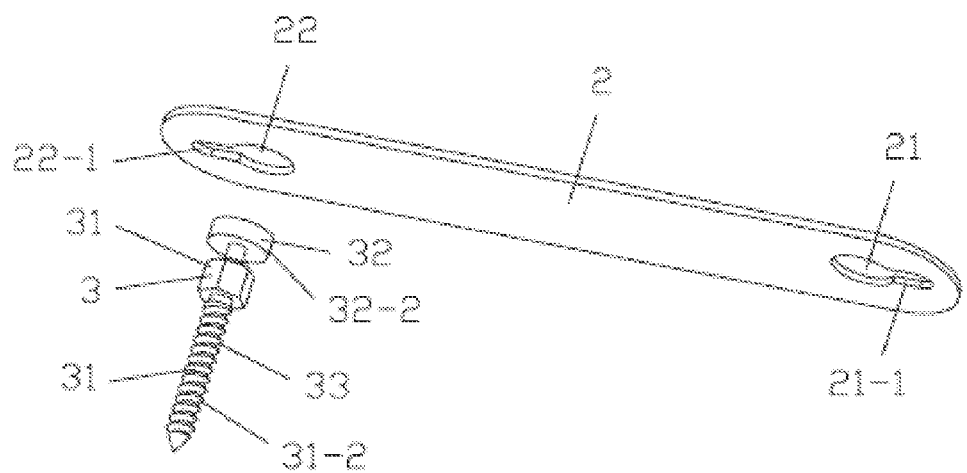
Figures 2, 3:
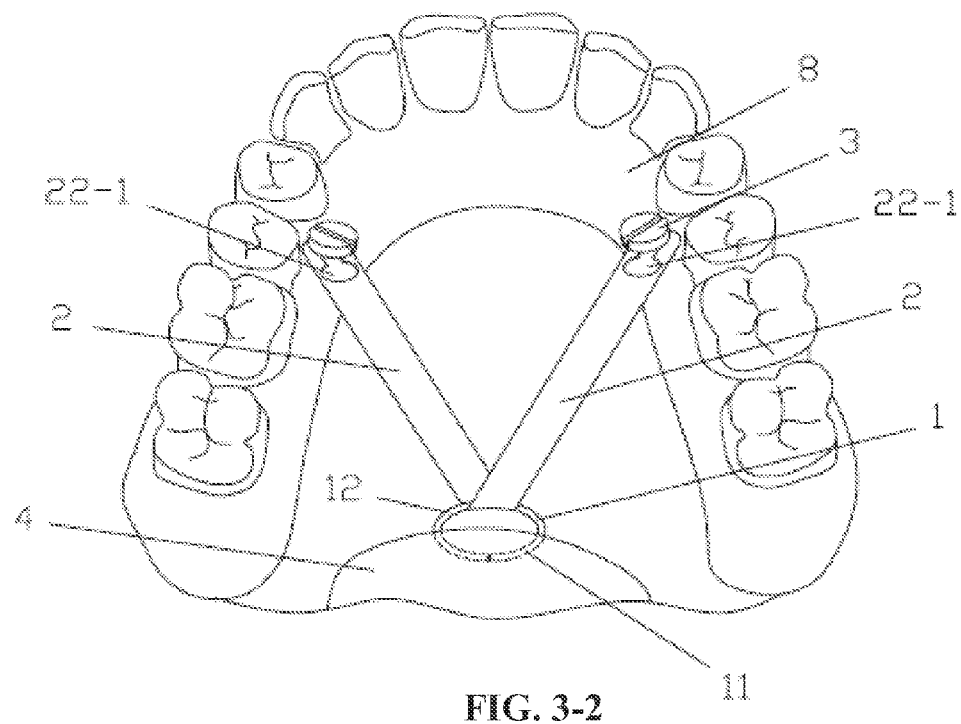
Figure 4:
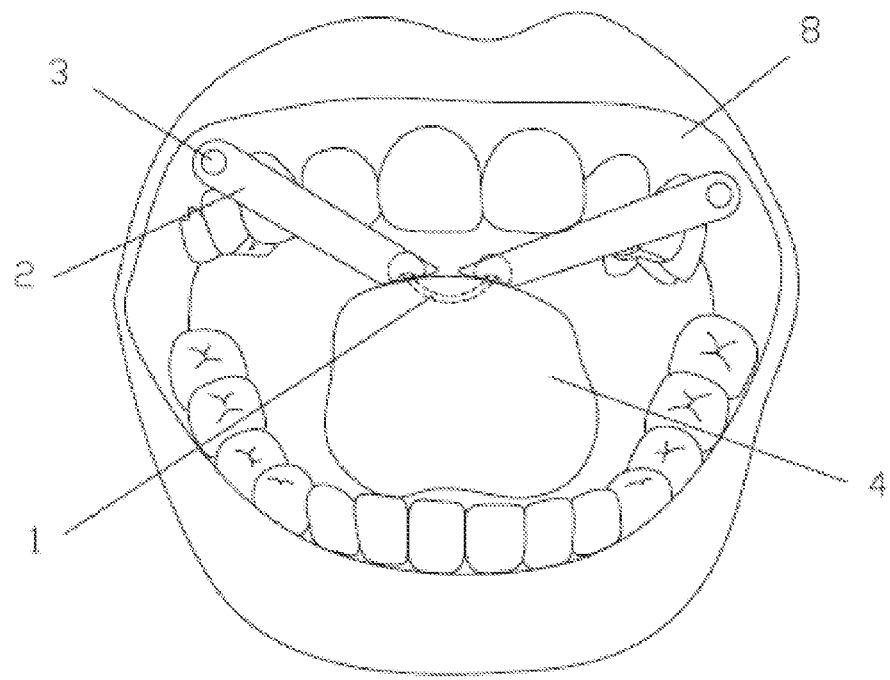
Figure 5:
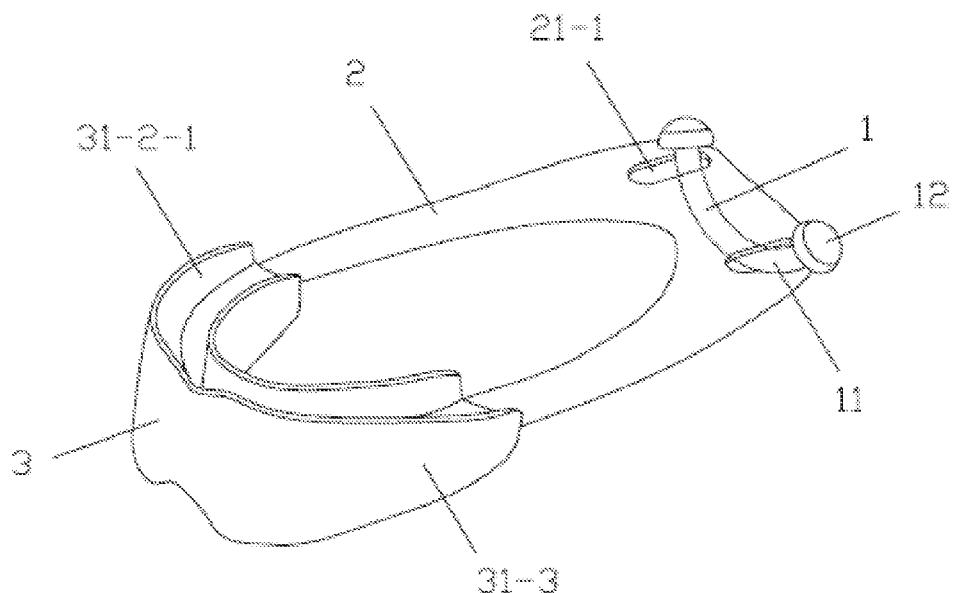
Figure 6:
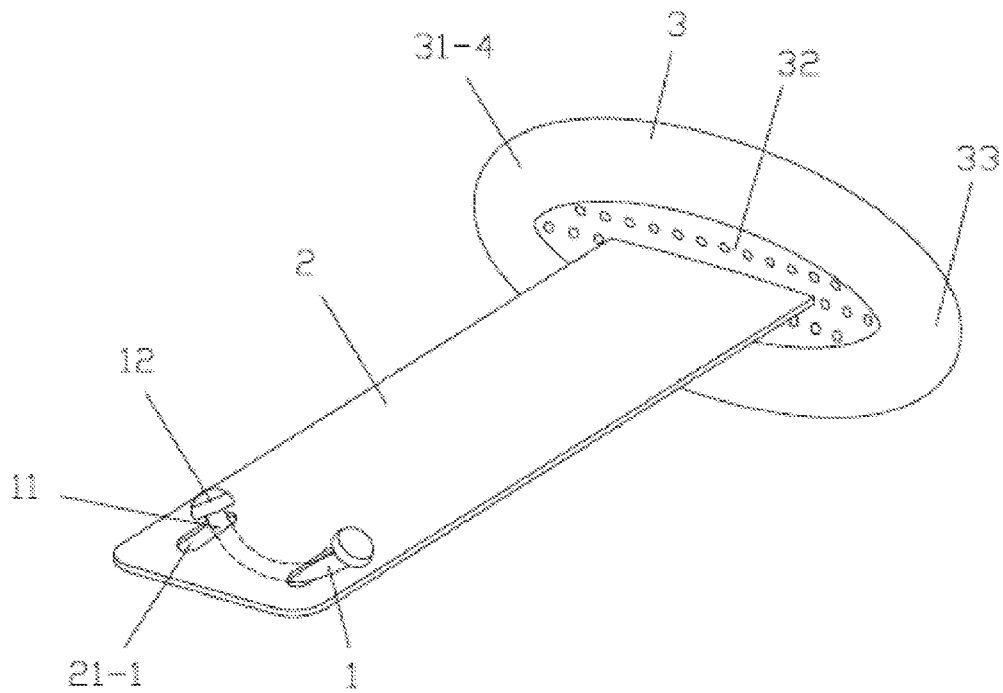
Figure 7:
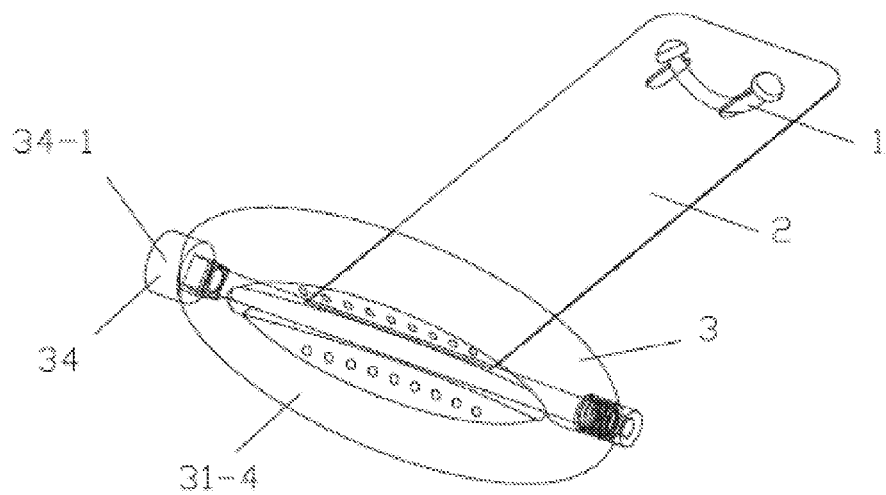
Figures 1, 7:
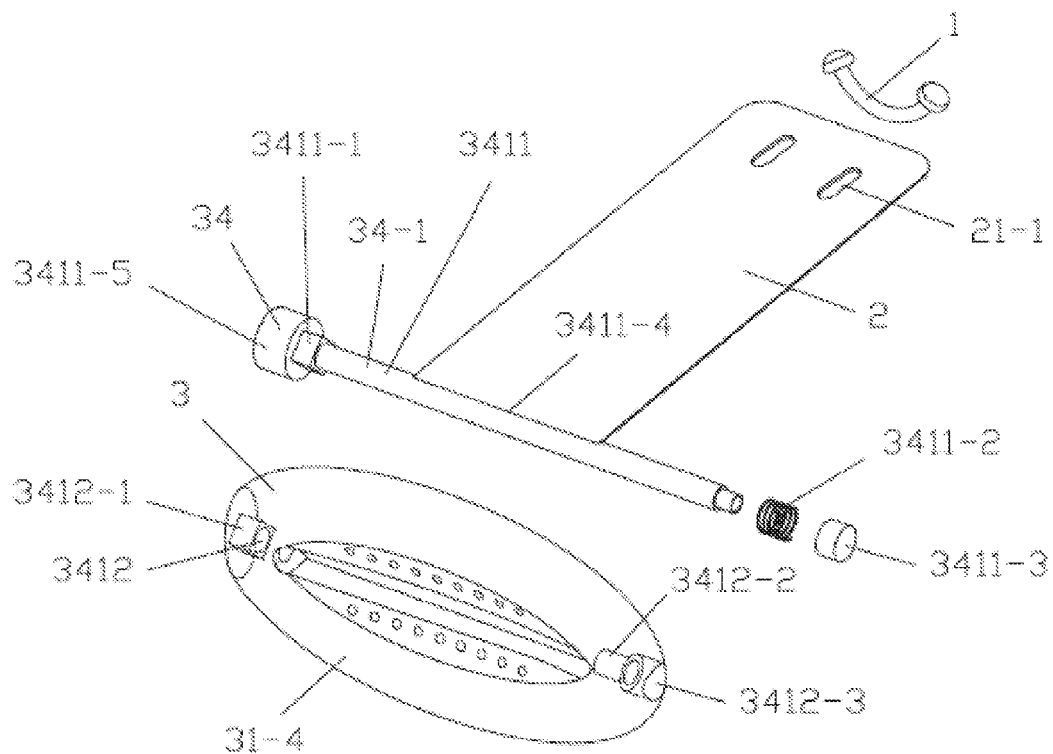
Figure 8:
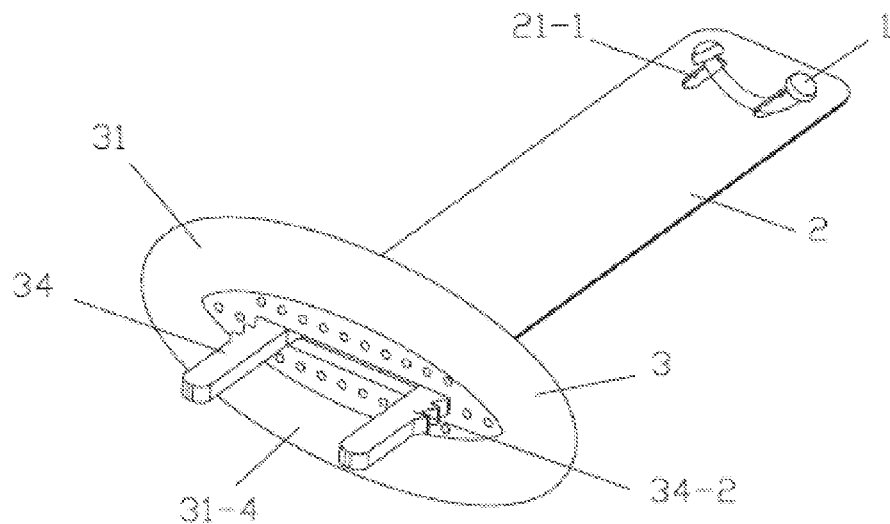
Figures 1, 8:
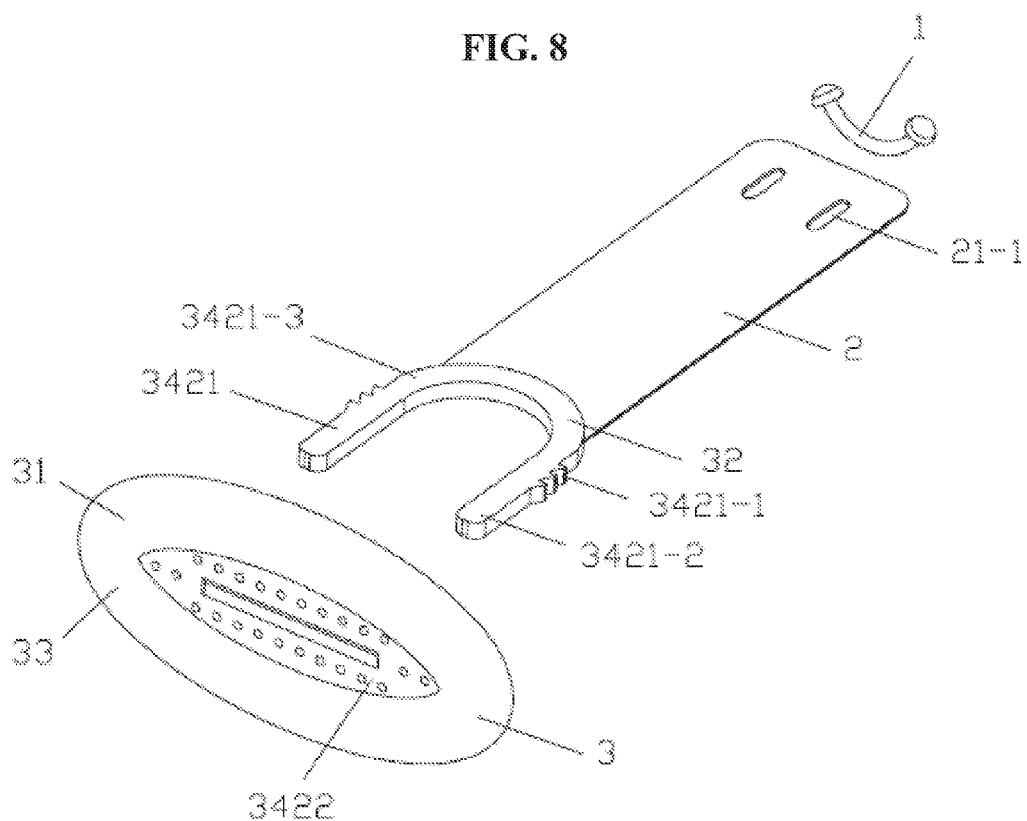

The slide block 3421 includes a positioning tooth groove 3421-1, a handle 3421-2, and a slide-block bracket 3421-3. The slide-block bracket 3421-3 is a bracket having a U-shaped structure. The handle 3421-2 is located at two ends of the U-shaped slide-block bracket 3421-3, the handle 3421-2 is pressed to move toward the inner side, and the U-shaped slide-block bracket 3421-3 shrinks inward, so that the positioning tooth groove 3421-1 can detach from the positioning block 3422, and the slide block 3421 can move back and forth. When the pressure on the handle 3421-2 is released, the U-shaped slide-block bracket 3421-3 restores its original shape, and the positioning tooth groove 3421-1 is locked on the positioning block 3422 to provide a function of restricting back-and-forth movement of the slide block 3421, as shown in FIG. 8-1.

The tongue-side connection end of the elastic retractor 2 is fixed to the U-shaped slide-block bracket 3421-3, so that when the slide block 3421 is pulled forward, the pull force of the elastic retractor 2 can be increased; and on the contrary, when the slide block 3421 moves backward, the pull force of the elastic retractor 2 can be reduced.

Embodiment 9: Elastic Tongue-Dorsum Retraction Device of the Present Invention that is Adjustable Through an Elastic Retractor Referring to FIG. 9, a difference of this embodiment lies in that: in this embodiment, more than one tongue-side connection hole 21-1 or more than one tooth-side connection hole 22-1 are provided at different positions on the elastic retractor 2, and different retraction forces are obtained by fixing the tongue-side connection holes 21-1 that are at different positions to the tongue dorsum connection mechanism 1.

In this embodiment, the elastic retractor 2 is made of a medical elastic film, where the medical elastic film is selected from a group consisting of medical elastic materials such as a medical silica gel film, a medical latex film, a medical polyurethane film, and a medical rubber film, and the medical elastic film has a thickness of 0.01 mm to 3 mm. The elastic retractor 2 is generally made of a 0.10 mm to 0.30 mm medical latex film or medical silica gel film.

The elastic retractor 2 may be manufactured into a Y-shape.

The two upper ends of the Y-shaped elastic retractor 2 serve as ends, connected to tooth-side fasteners 3, of the elastic retractor 2. A through hole Y1, a through hole Y2, and a through hole Y3 are provided at different positions of the two upper ends of the Y-shape. The through hole Y1, or the through hole Y2, or the through hole Y3 forms a tooth-side connection hole 22-1, and the tooth-side connection hole 22-1 can be sleeved over the positioning convex step 32-2 of the tooth-side fastener 3.

The lower end of the Y-shaped elastic retractor 2 service as an end, connected to the tongue dorsum connection mechanism 1, of the elastic retractor 2. A through hole S1, a through hole S2, and a through hole S3 are provided at different positions of the lower end of the Y-shaped elastic retractor 2. The through hole S1, or the through hole S2, or the through hole S3 serves as a tongue-side connection hole 21-1, and the tongue-side connection hole 21-1 can be removably mounted on the connection convex step 12-2 of the tongue dorsum connection mechanism 1.

When different tongue-side connection holes 21-1 are connected to the tongue dorsum connection mechanism 1, the elastic retractor 2 undergoes different amounts of elastic deformation, so that different retraction forces can be obtained. Likewise, when different tooth-side connection holes 22-1 are connected to the tooth-side fastener 3, different retraction forces can also be obtained. In this way, an elastic tongue-dorsum retraction device of the present invention that is adjustable through an elastic refractor is obtained.

Embodiment 10: Under-the-Tongue-Mucosa Epithelialized Tunnel-Type Elastic Tongue-Dorsum Retraction Device of the Present Invention Referring to FIG. 10 and FIG. 10-1, in this embodiment, an under-the-tongue-mucosa tunnel-type retraction mechanism 100 that can pull up the sagging tongue is used as the tongue dorsum connection mechanism 1. The under-the-tongue-mucosa tunnel-type retraction mechanism 100 may be formed in the following manner:

Through a minimally invasive surgery under local anesthesia, at positions on two sides that are about 1 cm to 4 cm in front of circumvallate papillae and are at a distance of about 1 cm to 3 cm from the midline, the tongue mucosa is perforated, and an implant 100-2 that can form an under-the-tongue-mucosa tunnel, which is generally a medical silica gel tube, is implanted at the tongue dorsum, so that most of the medical silica gel tube is implanted under the mucosa of the tongue dorsum, and two ends of the medical silica gel tube are exposed out of the left and right sides of the mucosa of the tongue dorsum, and are knotted to form a ring. After 15 days to 45 days after the surgery, if the patient does not feel pain or discomfort when the medical silica gel tube is pulled, the medical silica gel tube implanted under the mucosa of the tongue dorsum can be pulled out. After the medical silica gel tube is pulled out, an epithelialized tunnel 100-1 is formed at the position on the tongue dorsum where the medical silica gel tube is implanted. The under-the-tongue-mucosa epithelialized tunnel 100-1 may serve as the under-the-tongue-mucosa tunnel-type retraction mechanism 100 of the present invention, and the elastic retractor 2 is passed through the under-the-tongue-mucosa epithelialized tunnel 100-1 to pull up and forward the sagging tongue, as shown in FIG. 10-1.

This embodiment is advantageous in that: after the under-the-tongue-mucosa epithelialized tunnel 100-1 is formed at the tongue dorsum, no implant exists at the tongue dorsum, causing no foreign body sensation or discomfort to the patient. Before sleep, when the tongue dorsum needs to be retracted, the elastic retractor 2 can be passed through the under-the-tongue-mucosa epithelialized tunnel 100-1 and fixed to the tooth-side fastener 3, so that the sagging tongue can be pulled up and forward to enlarge the airway at the glossopharyngeal portion, thereby treating snoring and OSAHS. After getting up, the elastic retractor 2 can be removed from the tooth-side fastener 3, and the elastic retractor 2 can also be pulled out from the under-the-tongue-mucosa epithelialized tunnel 100-1, thereby allowing free movement of the tongue.

The elastic retractor 2 in this embodiment is generally made of a medical latex film or medical silica gel film having good elasticity and has a thickness of about 0.03 mm to 0.10 mm. Alternatively, a medical latex tube or a medical silica gel tube may be selected as the elastic retractor 2. Alternatively, a medical latex wire or a medical silica gel wire may be used as the elastic retractor 2. Compared with a thin-film strip-shaped elastic retractor 2, the wire-like elastic retractor 2 can be passed through the under-the-tongue-mucosa epithelialized tunnel 100-1 more easily, and is more convenient to use.

This embodiment is disadvantageous in that: the under-the-tongue-mucosa epithelialized tunnel 100-1 lacks a supporting force and is generally in collapsed state; as a result, it is difficult to pass the strip-shaped elastic retractor 2 through the under-the-tongue-mucosa epithelialized tunnel 100-1, and the strip-shaped elastic retractor 2 needs to be passed through the under-the-tongue-mucosa epithelialized tunnel 100-1 with the assistance of a special tool, that is, a line guide 200.

Embodiment 11: Thin-Walled Tube-Shaped Under-the-Tongue-Mucosa Tunnel-Type Elastic Tongue-Dorsum Retraction Device of the Present Invention Referring to FIG. 11 and FIG. 11-1, this embodiment is an improvement to Embodiment 10. A thin-walled tube-shaped implant 100-4 is implanted under the tongue mucosa. The thin-walled tube-shaped implant 100-4 is a medical titanium metal thin-walled tube bent into an arc shape. After 15 days to 60 days after the medical titanium metal thin-walled tube is implanted under the tongue mucosa, the medical titanium metal thin-walled tube is fixed into the tongue tissues under the tongue mucosa, and only tube openings at two ends of the medical titanium metal thin-walled tube remain outside the tongue mucosa. Such an under-the-tongue-mucosa tunnel supported by a thin-walled tube forms an under-the-tongue-mucosa tunnel 100-3 of the present invention that has a thin-walled tube-shaped implant.

Supported by the metal thin-walled tube, the under-the-tongue-mucosa tunnel 100-3 having a thin-walled tube-shaped implant does not collapse, which facilitates passing of the elastic retractor 2 therethrough. This overcomes the disadvantage that the under-the-tongue-mucosa epithelialized tunnel 100-1 in Embodiment 10 lacks a supporting force and is easy to collapse, making it difficult for the elastic retractor 2 to pass therethrough.

To further facilitate passing of the elastic retractor 2 through the under-the-tongue-mucosa tunnel 100-3 having a thin-walled tube-shaped implant, the tube opening part of the thin-walled tube-shaped implant 100-4, which is exposed outside the tongue mucosa, may be provided with a step or a horn opening. This not only facilitates insertion and passing of the elastic retractor 2, but also helps fix the thin-walled tube-shaped implant 100-4 to prevent displacement and falling, as shown in FIG. 11-2.

Embodiment 12: Coil Spring-Shaped Under-the-Tongue-Mucosa Tunnel-Type Elastic Tongue-Dorsum Retraction Device of the Present Invention Referring to FIG. 12, this embodiment is a further improvement to Embodiment 11. A difference of this embodiment lies in that, the thin-walled tube implant 100-4 is a densely arranged spiral tube made of a titanium-nickel shape memory alloy having a shape memory function, which replaces the titanium alloy thin-walled tube used in Embodiment 11.

After being implanted under the tongue mucosa, the medical densely arranged coil spring tube is fixed into the tongue tissues under the tongue mucosa, and only tube openings of the densely arranged spiral tube are exposed to two sides of the tongue mucosa. The densely arranged spiral tube fixed under the tongue mucosa forms an under-the-tongue-mucosa tunnel 100-3 of the present invention that has a thin-walled tube-shaped implant. Supported by the densely arranged coil spring tube, the under-the-tongue-mucosa tunnel 100-3 having a thin-walled tube-shaped implant does not collapse, which facilitates passing of the elastic retractor 2. In addition, compared with the titanium metal thin-walled tube, the densely arranged coil spring tube has good flexibility, which further improves comfort to the tongue, as shown in FIG. 12.

The densely arranged coil spring tube is generally made of a titanium-nickel shape memory alloy wire, and is thermally set so that the geometrical shape of the densely arranged coil spring tube meets physiological requirements on the position for implantation of the tongue dorsum. Further, a horn opening is provided at the tube opening, which not only facilitates insertion and passing of the elastic retractor 2, but also helps fix the thin-walled tube-shaped implant 100-4 to prevent displacement and falling, as shown in FIG. 12.

Embodiment 13: Elastic Tongue-Dorsum Retraction Device of the Present Invention that has a Ferromagnetic Fully-Implantable Connector Referring to FIG. 13 and FIG. 13-1, in this embodiment, the implant 101, which is fixed to the tongue, of the tongue dorsum connection mechanism 1 implanted at the tongue dorsum is a fully-implantable connector 102 fully implanted under the tongue mucosa. The fully-implantable connector 102 is a flat object 102-1.

The fully-implantable connector 102 is made of a ferromagnetic medical metal material, for example, is made of a ferromagnetic medical stainless steel plate having a thickness of 0.30 mm to 0.60 mm. The ferromagnetic medical stainless steel plate is manufactured into a flat object 102-1 having a dimension of about 8 mm by 20 mm, which serves as the fully-implantable connector 102 of the tongue dorsum connection mechanism 1, and is implanted at the tongue dorsum.

Through a minimally invasive surgery under local anesthesia, one flat object 102-1 is implanted under the tongue mucosa at each of positions on two sides that are about 1 cm to 4 cm in front of circumvallate papillae and are at a distance of about 1 cm to 2 cm from the midline, so that the flat objects 102-1 are completely covered by the tongue mucosa.

After 15 days to 60 days after the surgery, after the implanted ferromagnetic flat object 102-1 is completely fixed in the tongue tissues under the tongue mucosa, elastic retraction to the tongue dorsum can be carried out.

An elastic retractor 2 having a magnetic material is selected for elastic retraction to the ferromagnetic fully-implantable connector 102.

The tongue-side connection mechanism 21 of the elastic refractor 2 has a magnetic material. Such an elastic retractor 2 having a magnetic material can be attracted to the ferromagnetic fully-implantable connector 102, the elastic retractor 2 is spaced from the fully-implantable connector 102 by tongue mucosa tissues, and a magnetic connection is formed between the elastic retractor 2 and the fully-implantable connector 102.

Then, the tooth-side connection mechanism 22 of the elastic retractor 2 is fixed to the tooth-side fastener 3. In this way, by using the tooth-side fastener 3 as the supporting point, the sagging tongue can be pulled up through the magnetic connection between the elastic retractor 2 and the tongue dorsum connection mechanism 1, so as to enlarge the airway at the glossopharyngeal portion, thereby treating snoring and OSAHS.

Figure 13:
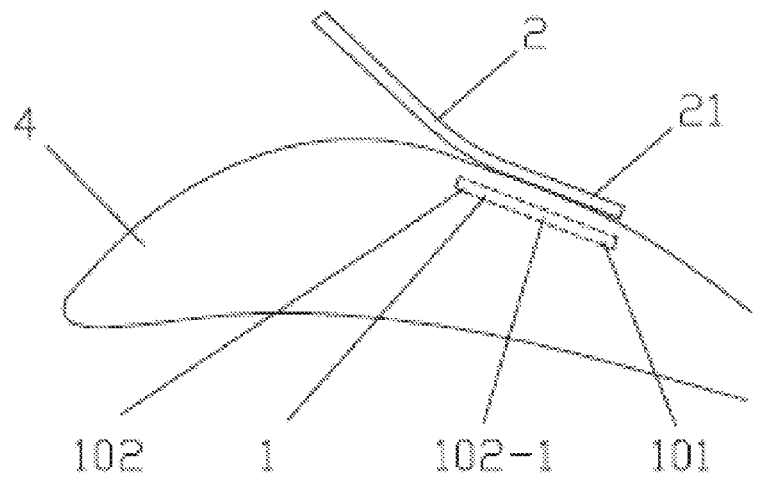
FIG. 13 is a schematic structural view of an elastic tongue-dorsum retraction device of the present invention that has a magnetic connection-type fully-implantable connector.
Figures 1, 13:
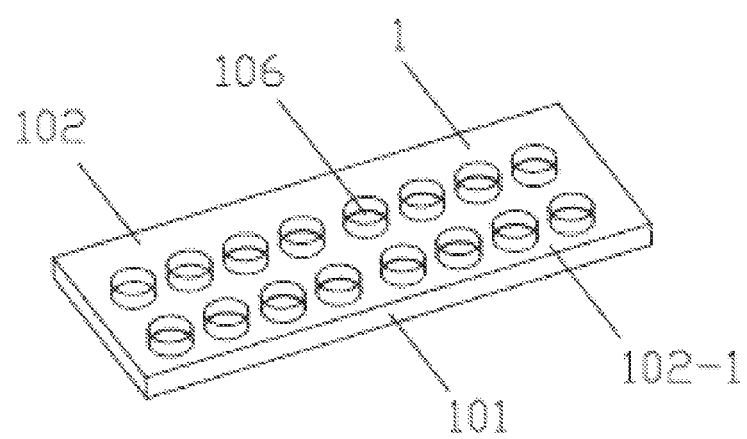

To prevent the fully-implantable connector 102 implanted under the tongue mucosa from displacing in the tongue tissues, through holes 106 may be provided on the fully-implantable connector 102. Growth and attachment of the tongue tissues in the through holes 106 can prevent the fully-implantable connector 102 from displacing in the tongue tissues, as shown in FIG. 13-1.

Embodiment 14: Magnetic Connection-Type Elastic Tongue-Dorsum Retraction Device of the Present Invention Referring to FIG. 14 to FIG. 14-4, in this embodiment, Embodiment 13 is further improved.

To improve the adaptability of the magnetic fully-implantable connector 102 implanted at the tongue dorsum to movement of the tongue, the magnetic fully-implantable connector 102 is improved.

In this embodiment, the fully-implantable connector 102 serving as the tongue dorsum connection mechanism 1 is a flat object 102-1. The flat object 102-1 uses a composite structure in which magnetic units 1021-1 are completely wrapped in a base body 1021-2, as shown in FIG. 14-2 and FIG. 14-3.

Figure 14:
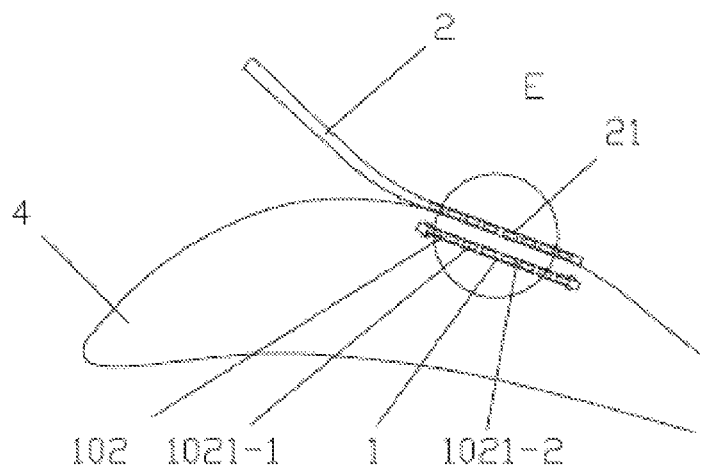
FIG. 14 is a schematic structural view of a magnetic connection-type elastic tongue-dorsum retraction device of the present invention.
Figures 1, 14:
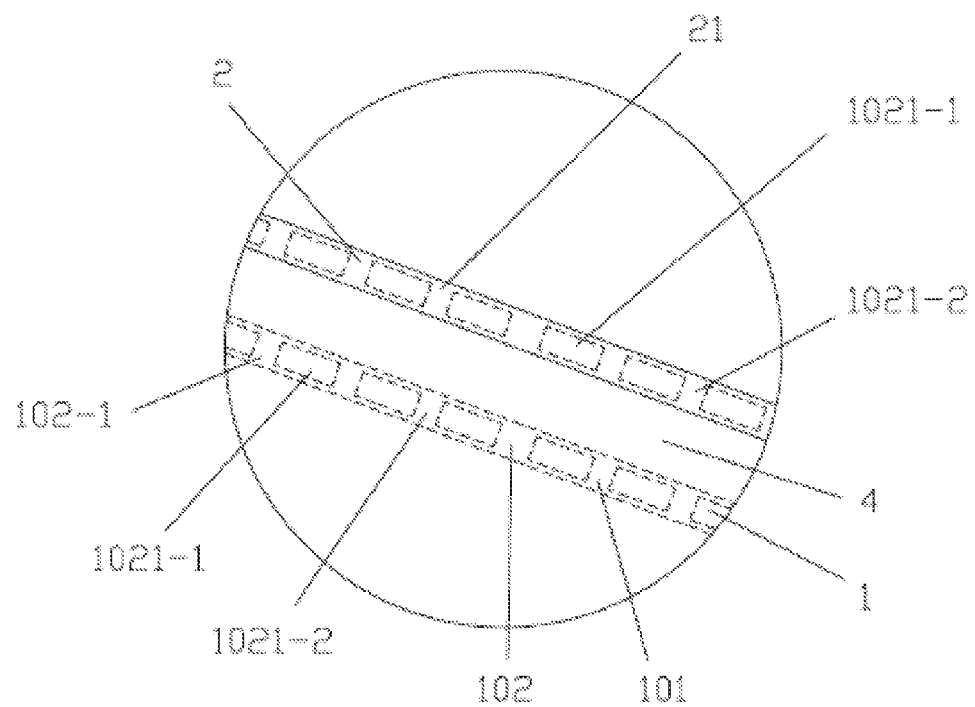
Figures 2, 14:
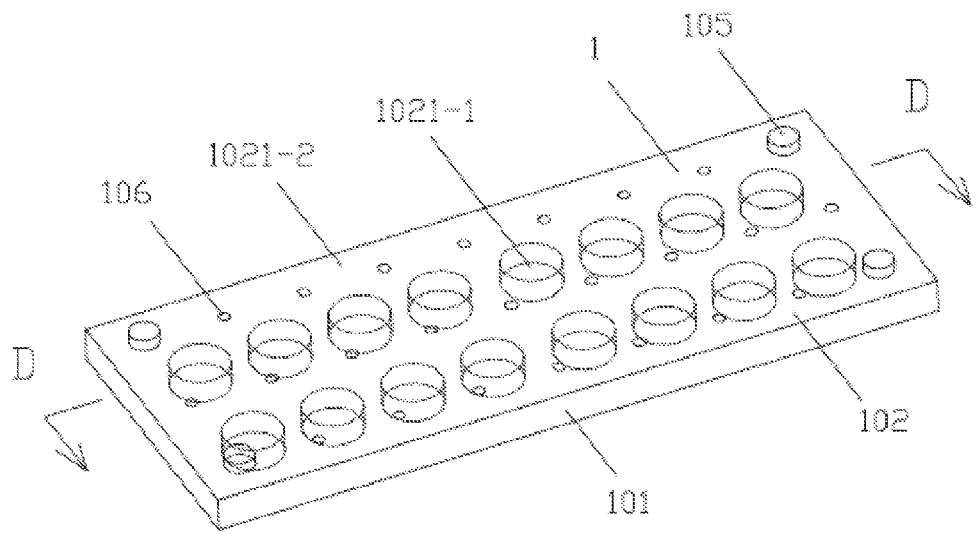
Figures 3, 14:
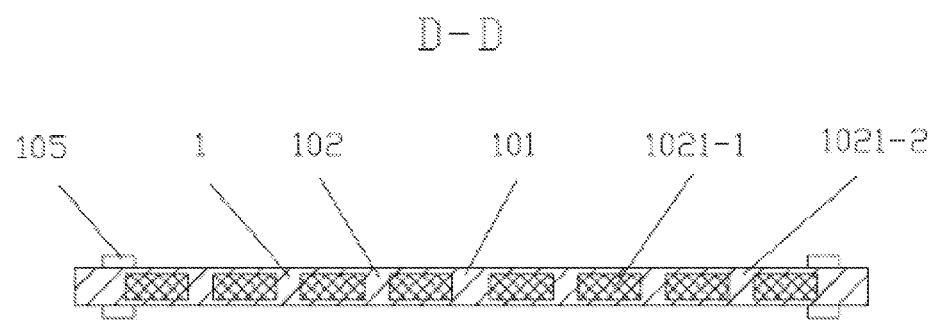
Figures 4, 14:
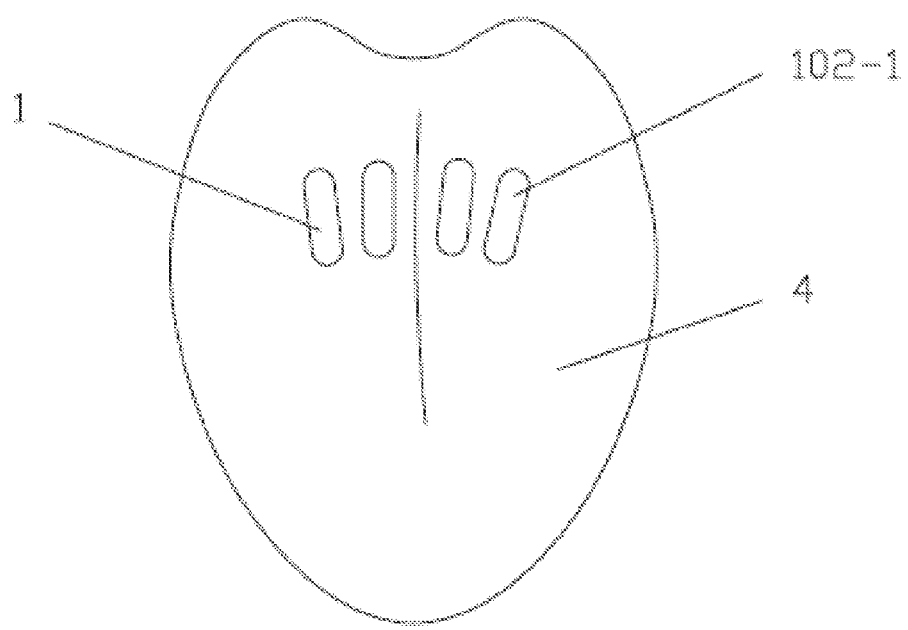

Medical silica gel is selected as the base body 1021-2; alternatively, other flexible medical materials such as medical polyurethane that can be implanted in the human body for a long term may also be selected as the raw material of the base body 1021-2, as shown in FIG. 14-2 and FIG. 14-3.

A neodymium-iron-boron permanent magnetic material is selected as the magnetic units 1021-1. Generally, neodymium-iron-boron magnetic sheets having a large contact area are used as the magnetic units 1021-1; alternatively, neodymium-iron-boron magnetic powder, or particles or powder of other permanent magnetic materials may be used as the magnetic units 1021-1, as shown in FIG. 14-2 and FIG. 14-3.

In a mold, according to a common process of wrapping metal powder with medical silica gel, the magnetic units 1021-1 which are neodymium-iron-boron magnetic sheets are completely wrapped in the base body 1021-2 of medical silica gel, to obtain a magnetic medical silica gel strip, which can be used as the fully-implantable connector 102 of the tongue dorsum connection mechanism 1 after cutting, cleaning and sterilizing.

The magnetic units 1021-1 of the magnetic medical silica gel strip are completely wrapped in the base body 1021-2 of medical silica gel. The magnetic medical silica gel strip has magnetic properties due to the existence of the magnetic units 1021-1 and has good elasticity and deformability due to the existence of the base body 1021-2 of medical silica gel, and not only can be used as the fully-implantable connector 102, but also can be used as the elastic retractor 2; particularly, the tongue-side connection mechanism 21 of the elastic retractor 2 may be made of this material, so that magnetic connection can be achieved, as shown in FIG. 14 and FIG. 14-1.

In this embodiment, the tongue-side connection mechanism 21 of the elastic retractor 2 may also be made of such a magnetic medical silica gel material in which the base body 1021-2 completely wraps the magnetic units 1021-1, so as to enable the tongue-side connection mechanism 21 of the elastic refractor 2 to have magnetic properties.

Since the tongue tissues cannot be easily attached to the implant made of the medical silica gel material to fix it, through holes 106 and convex steps 105 may be provided on the flat object 102-1 used as the fully-implantable connector 102, so as to prevent displacement of the implanted flat object 102-1 by means of growth and attachment of the tongue tissues in the through holes 106 and the convex steps 105, as shown in FIG. 14-1 and FIG. 14-2.

Through a minimally invasive surgery under local anesthesia, more than one magnetic flat object 102-1 is implanted under the tongue mucosa at each of positions on two sides that are about 1 cm to 4 cm in front of circumvallate papillae and are at a distance of about 1 cm to 2 cm from the midline, so that the magnetic flat objects 102-1 are completely covered by the tongue mucosa, as shown in FIG. 14-4.

After 15 days to 60 days after the surgery, after the implanted magnetic flat object 102-1 is completely fixed in the tongue tissues under the tongue mucosa, elastic retraction to the tongue dorsum can be carried out.

Before sleep, the magnetic elastic retractor 2 is selected to retract the magnetic fully-implantable connector 102 of the tongue dorsum connection mechanism 1.

The fully-implantable connector 102 implanted under the mucosa of the tongue dorsum has magnetic properties, one end of the elastic retractor 2 is fixed to the tooth-side fastener 3, and the tongue-side connection mechanism 21 at the other end of the elastic retractor 2 also has magnetic properties; therefore, a magnetic connection can be established by simply inserting the tongue-side connection mechanism 21 of the magnetic elastic refractor 2 to a position adjacent to the tongue dorsum where the implant is implanted, because they have opposite poles and attract each other, as shown in FIG. 14 and FIG. 14-1. In this way, by using the tooth-side fastener 3 as the supporting point, the sagging tongue can be pulled up through the magnetic connection between the elastic retractor 2 and the tongue dorsum connection mechanism 1, so as to enlarge the airway at the glossopharyngeal portion, thereby treating snoring and OSAHS.

After getting up, by applying a force to separate the tongue-side connection mechanism 21 of the magnetic elastic retractor 2 from the tongue dorsum to which it is attracted, the magnetic connection can be released, thereby releasing elastic retraction to the tongue.

Embodiment 15: Elastic Tongue-Dorsum Retraction Device of the Present Invention that is Adhered to the Tongue Dorsum Referring to FIG. 15, in this embodiment, the connector 101, which is fixed to the tongue, of the tongue dorsum connection mechanism 1 is a mucosa-surface-fixed-type connector 104. The mucosa-surface-fixed-type connector 104 includes a support base 104-1 that can be adhered or adsorbed to the surface of the mucosa of the tongue dorsum, and a connection mechanism 104-2 connected to the elastic retractor 2. The connection mechanism 104-2 is a connection convex step 1042-2, and the connection mechanism 104-2 is disposed on the support base 104-1.

Figure 15:
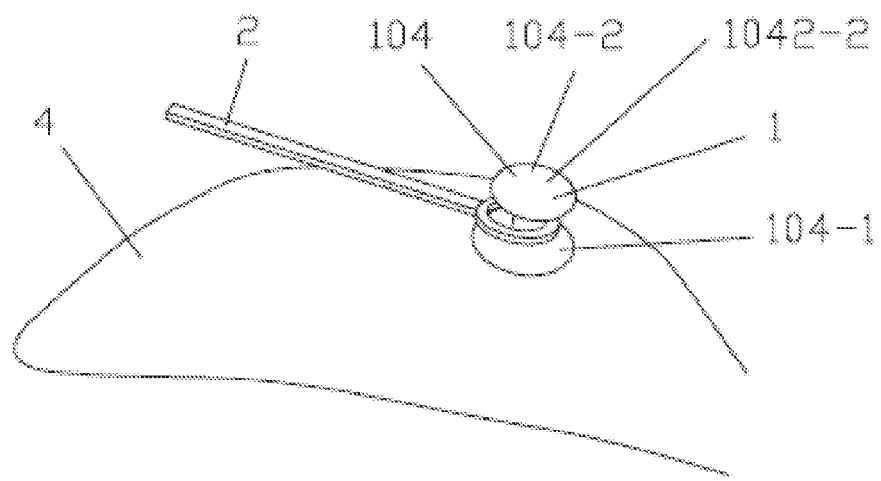
FIG. 15 is a schematic structural view of an elastic tongue-dorsum retraction device of the present invention that is adhered to the tongue dorsum.
Figures 1, 15:
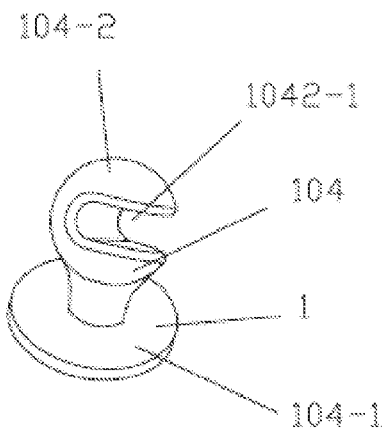
Figures 2, 15:
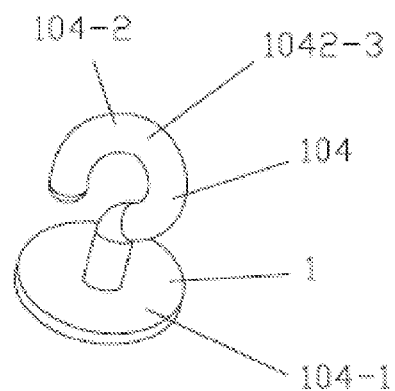
Figures 3, 15:
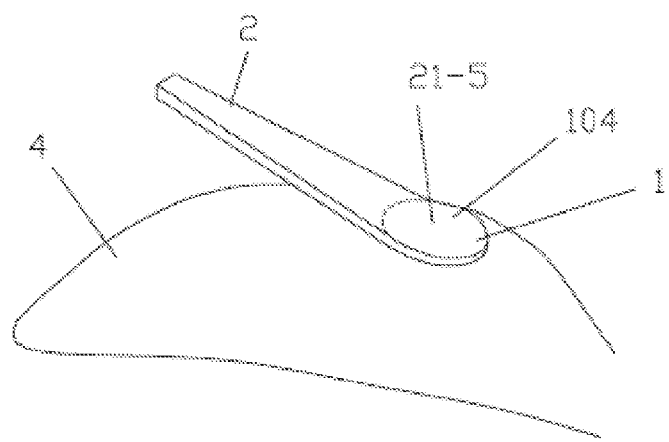

The mucosa-surface-fixed-type connector 104 may be adhered to the surface of the mucosa of the tongue dorsum by using a medical adhesive, as shown in FIG. 15. The elastic retractor 2 may be sleeved over the connection convex step 1042-2, and retraction to the sagging tongue can be achieved by using a pull force of the elastic retractor 2.

The connection mechanism 104-2 may be a connection concave groove 1042-1 as shown in FIG. 15-1, the connection convex step 1042-2 as shown in FIG. 15, or a connecting hook 1042-3 as shown in FIG. 15-2.

In addition, the support base 104-1 on the surface of the mucosa of the tongue dorsum may be made of a soft medical silica gel material, and the support base 104-1 is adsorbed to the surface of the mucosa of the tongue dorsum by negative pressure suction, as shown in FIG. 15.

Referring to FIG. 15-3, at a distal end of the elastic retractor 2, that is, an end portion 21-5 at one end adjacent to the tongue side, a medical adhesive is applied on a surface of the end portion 21-5 for contact with the mucosa of the tongue dorsum, and the end portion 21-5 is directly adhered to the surface of the mucosa of the tongue dorsum. In this case, the end portion 21-5 is not only a part of the elastic retractor 2, but is also equivalent to the mucosa-surface-fixed-type connector 104 of the tongue dorsum connection mechanism 1.

Embodiment 16: Elastic Tongue-Dorsum Retraction Device of the Present Invention that is Adhered Outside the Lip Referring to FIG. 16, in this embodiment, the tongue dorsum connection mechanism 1 is an elliptical ring-shaped connector 101 that is fixed to the tongue dorsum in a semi-implanted manner. The elliptical ring-shaped connector 101 has one part implanted under the tongue mucosa, and the other part exposed out of the mucosa of the tongue dorsum.

The elastic retractor 2 is an elongated elastic thin-film strip made of a medical latex film, and a medical adhesive is applied on two ends of the strip-shaped elastic retractor 2 to form a medical plaster-type structure.

Figure 16:
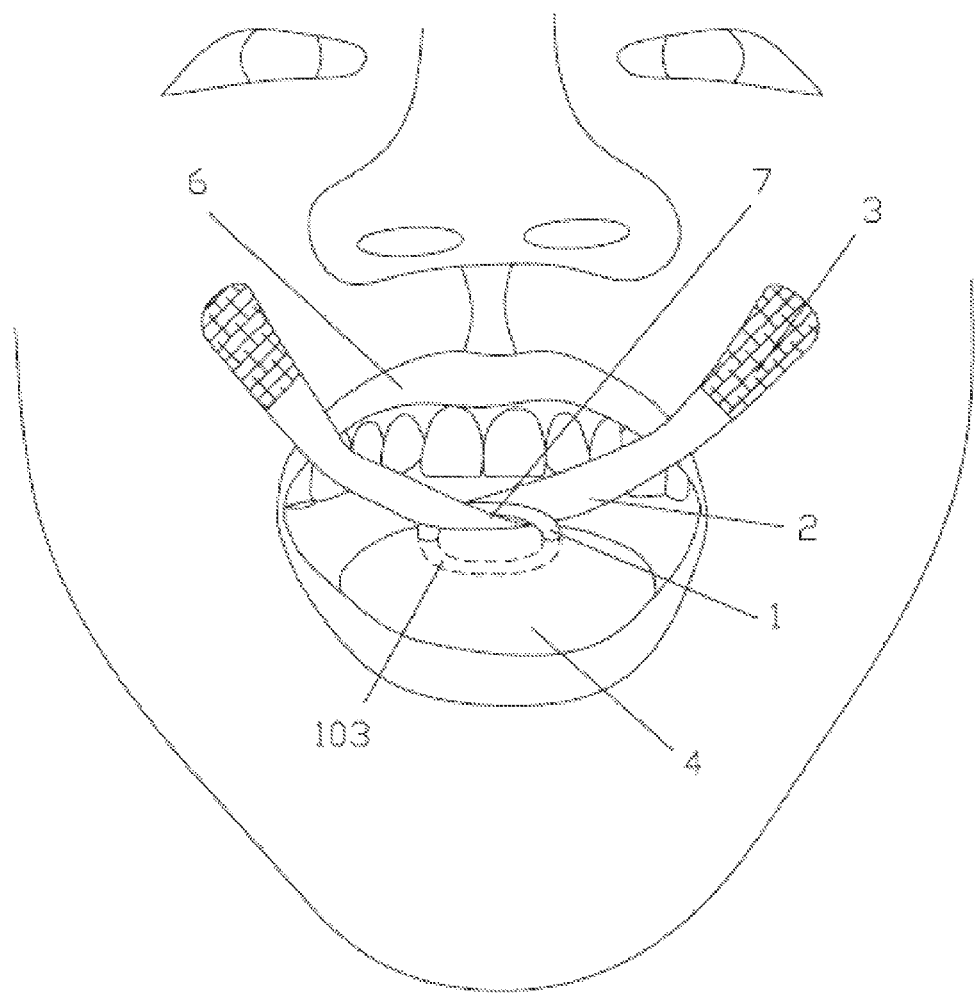
FIG. 16 is a schematic structural view of an elastic tongue-dorsum retraction device of the present invention that is adhered outside the lip.

After the strip-shaped elastic retractor 2 is passed through the elliptical ring-shaped connector 101, a protective film is torn, and the two ends of the strip-shaped elastic retractor 2 are respectively adhered to the cheek outside the lip, so that elastic retraction to the tongue dorsum can be achieved, and the airway at the glossopharyngeal portion can be enlarged, thereby treating snoring and OSAHS. In this case, the two ends of the elastic retractor 2 on which the medical adhesive is applied are equivalent to the tooth-side fasteners 3, as shown in FIG. 16.

Embodiment 17: Elastic Tongue-Dorsum Retraction Device of the Present Invention that Uses a Silica Gel Tunnel-Type Tongue Dorsum Connection Mechanism Referring to FIG. 17, in this embodiment, the tongue dorsum connection mechanism 1 is a tunnel-type tongue dorsum connection mechanism 100 made of medical silica gel. The elastic retractor 2 is a strip-shaped elastic retractor made of medical silica gel and having a plurality of tooth-side connection holes 22-1 at two ends thereof. The tooth-side fastener 3 is a tooth-side fastener 3 that can be adhesively fixed to the surface of teeth. The two tooth-side fasteners 3 are respectively adhesively fixed to the outer side of teeth at proper positions on two sides of incisors, and after the retractor 2 is passed through a center hole 100-4-3 of the tunnel-type tongue dorsum connection mechanism 100, the two ends of the retractor 2 are respectively fixed to the tooth-side fasteners 3 through the tooth-side connection holes 22-1. Thus, an elastic tongue-dorsum retraction device of the present invention that uses a silica gel tunnel-type tongue dorsum connection mechanism is formed.

Figure 17:
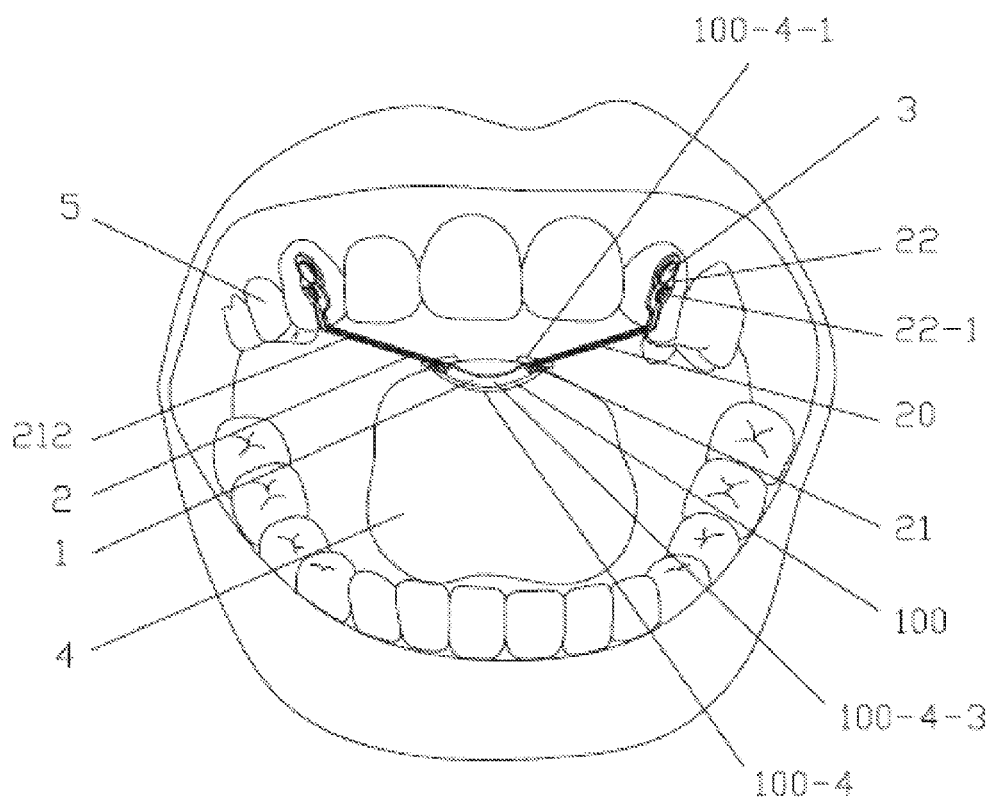
FIG. 17 is a schematic view depicting the working principle of a tunnel-type tongue dorsum connection mechanism of the present invention.
Figures 1, 17:
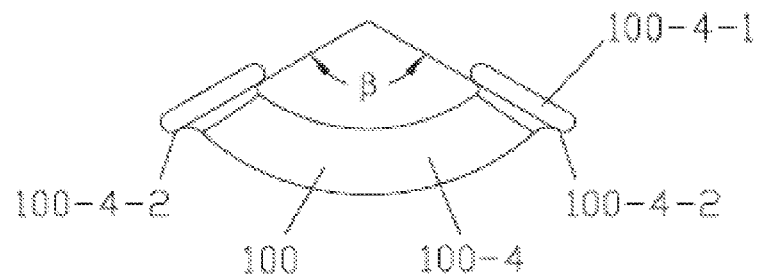
Figures 2, 17:
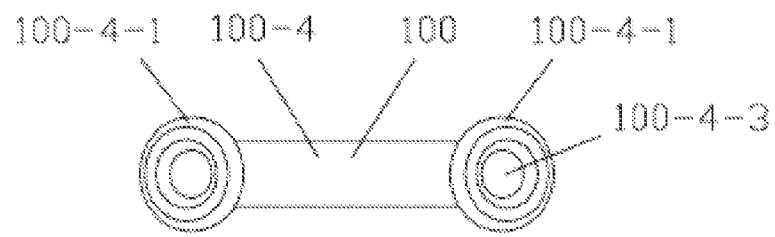
Figures 3, 17:
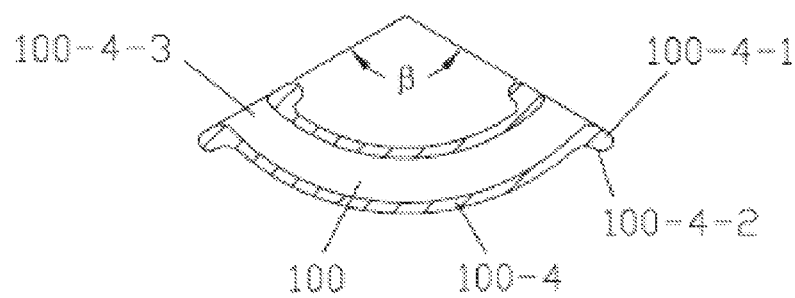

Referring to FIG. 17-1 to FIG. 17-3, in this embodiment, the tunnel-type tongue dorsum connection mechanism 100 is a thin-walled tube-shaped implant 100-4 made of medical silica gel. Two ends of the thin-walled tube-shaped implant 100-4 are each provided with an anti-slip positioning convex step 100-4-1, and the bottom of the anti-slip positioning convex step 100-4-1 has a smooth surface 100-4-2 matching the surface of the tongue mucosa. An angle β between the two smooth surfaces 100-4-2 of the positioning convex steps 100-4-1 at the two ends is 100° to 150°.

When the thin-walled tube-shaped implant 100-4 is implanted under the tongue mucosa, surface contact can be achieved between the tongue mucosa and the smooth surface 100-4-2 that is under the positioning convex step 100-4-1 and matches the surface of the tongue mucosa, so as to prevent the thin-walled tube-shaped implant 100-4 from sliding off from under the tongue mucosa. In addition, since the positioning convex step 100-4-1 is in surface contact with the tongue mucosa, irritation of the positioning convex step 100-4-1 to the surface of the tongue mucosa is reduced, so that comfort to the user can be enhanced.

An angle β of 100° to 150° is formed between the two smooth surfaces 100-4-2 of the positioning convex steps 100-4-1 at the two ends. The biological shape of the tongue body is an arch structure having a certain angle; therefore, after the thin-walled tube-shaped implant 100-4 is implanted under the tongue mucosa, the angle β allows the positioning convex step 100-4-1 to better conform to the mucosa on the surface of the tongue body, thereby improving comfort to the patient in use.

In addition, since the tunnel-type tongue dorsum connection mechanism 100 is made of medical silica gel, the shape can be changed at will when the tunnel-type tongue dorsum connection mechanism 100 is implanted under the tongue mucosa, so as to desirably adapt to the channel under the tongue mucosa. The soft material also provides better flexibility when the positioning convex step 100-4-1 contacts tongue mucosa tissues, which alleviates irritation to tongue mucosa tissues, thereby improving compliance of the patient.

During clinical use, first, through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, the thin-walled tube-shaped implant 100-4 of the tunnel-type tongue dorsum connection mechanism 100 is implanted and fixed, so that the positioning convex steps 100-4-1 at the two ends of the thin-walled tube-shaped implant 100-4 are exactly exposed out of the surface of the tongue mucosa. After 15 days to 60 days after the surgery, if the patient does not feel pain or discomfort when the thin-walled tube-shaped implant 100-4 is pulled, retraction to the tongue dorsum can be carried out.

Step 2: According to different specific structures to be used for the tooth-side fastener 3, the selected tooth-side fastener 3 is mounted and fixed by using teeth, the alveolar bone, the maxilla, the mandible, or positions outside the maxilla and mandible lips as supporting and fixing points of the tooth-side fastener 3. In this embodiment, the used tooth-side fastener 3 is adhesively fixed to the outer side of teeth, as shown in FIG. 17.

Step 3: Before sleep, the integral-type elastic retraction mechanism 212 is passed through the center hole 100-4-3 of the tunnel-type tongue dorsum connection mechanism of the present invention by using an auxiliary tool, and then two ends of the integral-type elastic retraction mechanism 212 are fixed to the tooth-side fastener 3. By using the tooth-side fastener 3 as a fulcrum, the integral-type elastic retraction mechanism 212 exerts an elastic pull force on the tunnel-type tongue dorsum connection mechanism 100 of the present invention. Under the effect of an elastic restoring force of the integral-type elastic retraction mechanism 212, the collapsed tongue root is pulled up forward, so as to enlarge the airway at the glossopharyngeal portion, thereby achieving the objective of treating OSAHS, as shown in FIG. 17.

When the integral-type elastic retraction mechanism 212 is mounted by using the tunnel-type tongue dorsum connection mechanism 100 of the present invention, the following aspects require special attention:

To adjust the magnitude of an elastic retraction force of the elastic deformation mechanism 20 of the integral-type elastic retraction mechanism 212, one of the tooth-side connection holes 22-1 on the tooth-side connection mechanism 22 of the integral-type elastic retraction mechanism 212 needs to be selected first. In this embodiment, the tooth-side connection hole 22-1 numbered 2 is selected from the tooth-side connection holes 22-1 numbered 1 to 4. Then, the integral-type elastic retraction mechanism 212 is fixed to the tooth-side fastener 3 through the selected tooth-side connection hole 22-1.

When a proper elastic retraction force of the elastic deformation mechanism 20 of the integral-type elastic retraction mechanism 212 is ensured, the tongue dorsum connection mechanism 1 of the integral-type elastic retraction mechanism 212 can be maintained exactly in the center hole 100-4-3 of the thin-walled tube-shaped implant 100-4 of the tunnel-type tongue dorsum connection mechanism 100; and the positions of the tongue-side connection mechanisms 21 at two sides of the tongue dorsum connection mechanism 1 of the integral-type elastic retraction mechanism 212 are basically consistent with the positions of the positioning convex steps 100-4-1 at two ends of the thin-walled tube-shaped implant 100-4 of the tunnel-type tongue dorsum connection mechanism 100 of the present invention. The elastic deformation mechanism 20 of the elastic retractor 2 of the integral-type elastic retraction mechanism 212 is exposed to a space between the positioning convex steps 100-4-1 of the tunnel-type tongue dorsum connection mechanism 100 of the present invention and the tooth-side fastener 3. Along with the movement of the tongue, the elastic deformation mechanism 20 can deform freely, and exerts a proper elastic retraction force on the tongue dorsum all the time.

Step 4: After getting up, the integral-type elastic retraction mechanism 212 is taken off from the tooth-side fastener 3, and drawn out from the center hole 100-4-3 of the tunnel-type tongue dorsum connection mechanism of the present invention, so as to release retraction to the tongue dorsum, as shown in FIG. 17.

Embodiment 18: Elastic Tongue-Dorsum Retraction Device of the Present Invention where a Connection Convex Step of a Tongue Dorsum Connection Mechanism is Provided with Longitudinal Connection Concave Grooves Referring to FIG. 18 to FIG. 18-13, a difference of this embodiment lies in that: in this embodiment, the elastic-retractor tongue dorsum connection mechanism 12, which is connected to the elastic retractor 2, on the tongue dorsum connection mechanism 1 uses the structure of a connection convex step 12-2, and the connection convex step 12-2 is provided with longitudinal connection concave grooves 12-1-2. By providing the longitudinal connection concave grooves 12-1-2, the reliability of connection between the elastic retractor 2 and the tongue dorsum connection mechanism 1 can be enhanced, so that the elastic retractor 2 does not slip out of the connection convex steps 12-2 even in the case of violent movement of the tongue, as shown in FIG. 18-1.

Figure 18:
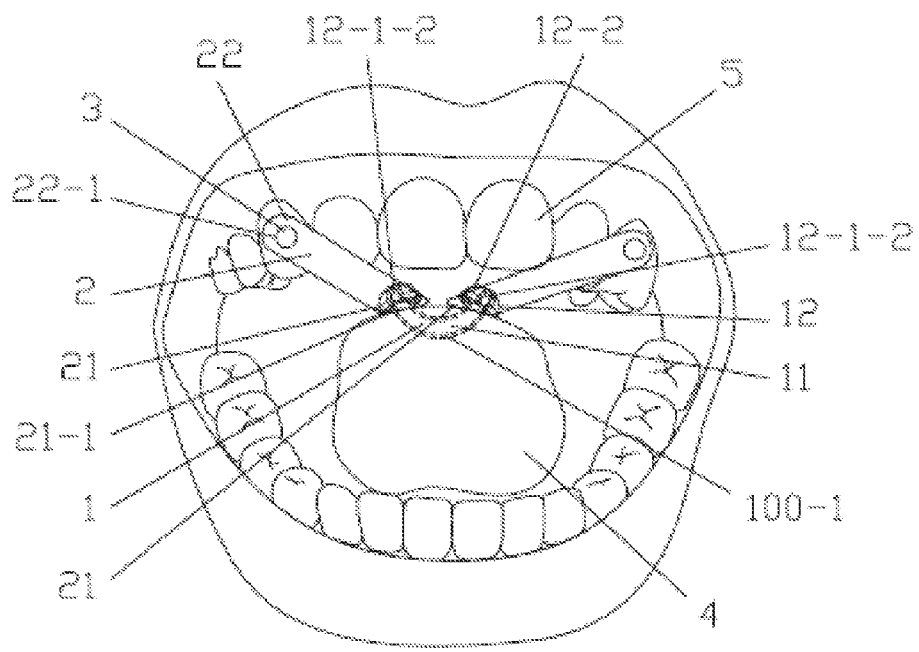
FIG. 18 is a schematic structural view of an elastic tongue-dorsum retraction device of the present invention where a connection convex step is provided with longitudinal connection concave grooves.
Figures 1, 18:
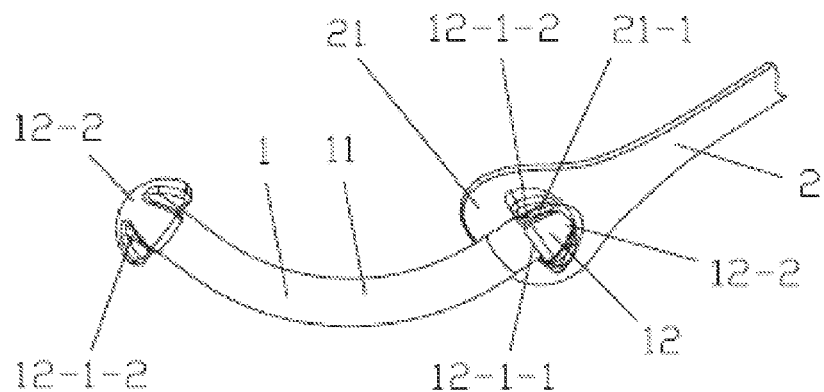
Figures 2, 18:
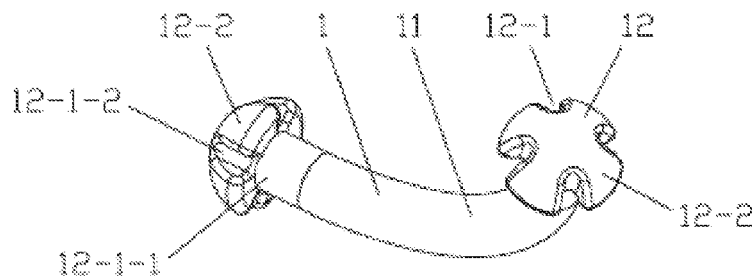
Figures 3, 18:
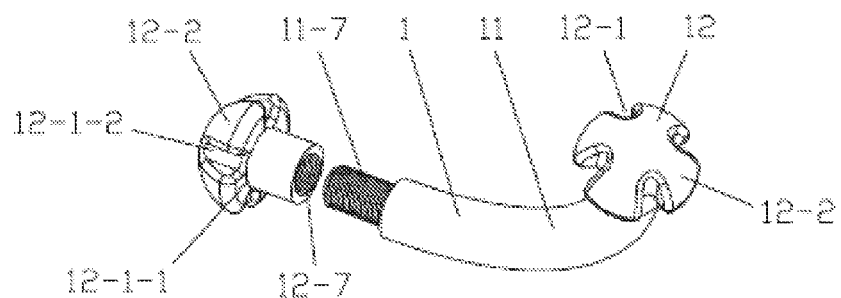
Figures 4, 18:
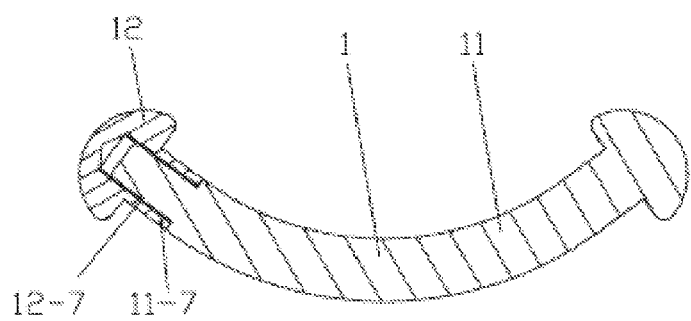
Figures 5, 18:
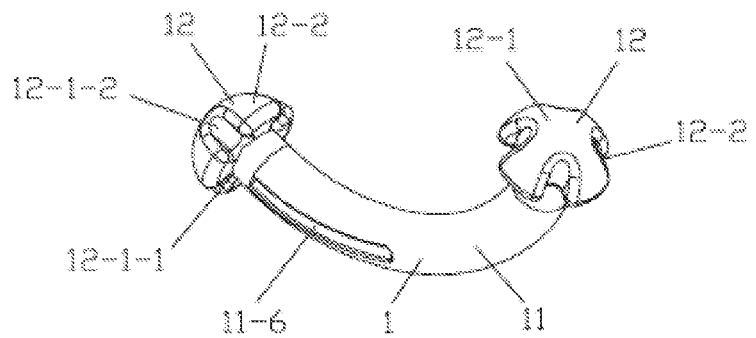
Figures 6, 18:
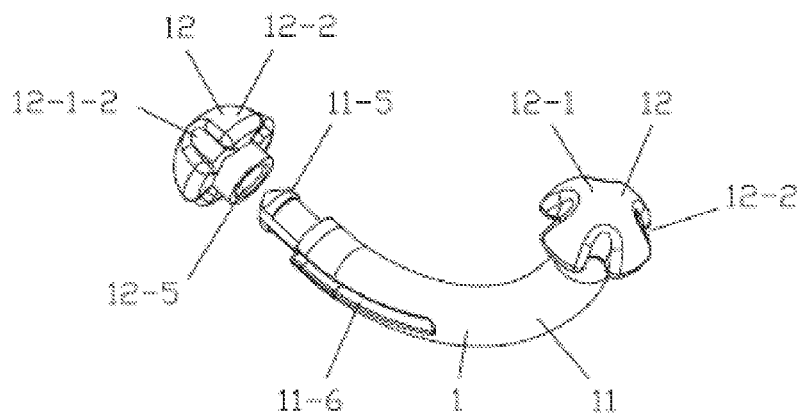
Figures 7, 18:
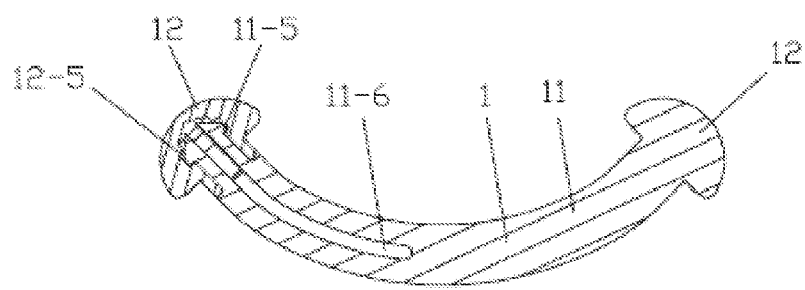
Figures 8, 18:
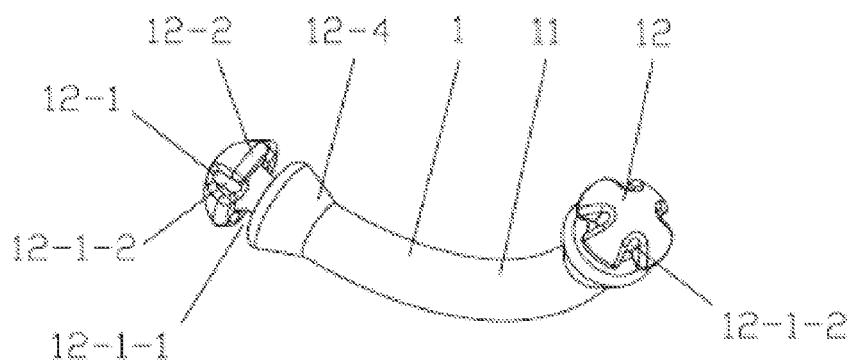

Referring to FIGS. 18-8 to 18-13, the tongue dorsum connection mechanism 1 includes a support 11, and an elastic-retractor tongue dorsum connection mechanism 12 connected to the elastic retractor 2. The support 11 is an arc-shaped cylinder, and a conical transition mechanism 12-4 is provided at each of two ends of the arc-shaped cylinder. The conical transition mechanism 12-4 enables surface contact between the tongue dorsum connection mechanism 1 and the mucosa on the surface of the tongue, which alleviates irritation to the mucosa on the surface of the tongue, and can improve comfort of the implanted tongue dorsum connection mechanism 1.

Referring to FIG. 18-1 to FIG. 18-10, the elastic-retractor tongue dorsum connection mechanism 12 connected to the elastic retractor is formed by a connection convex step 12-2 and connection concave grooves 12-1. The connection convex step 12-2 of the tongue dorsum connection mechanism 1 is semispherical. The connection concave grooves 12-1 of the tongue dorsum connection mechanism 1 include one transverse connection concave groove 12-1-1 and four longitudinal connection concave grooves 12-1-2. The four longitudinal connection concave grooves 12-1-2 are evenly distributed on the connection convex step 12-2 of the tongue dorsum connection mechanism. The transverse connection concave groove 12-1-1 is formed by a concave groove formed between the bottom of the connection convex step 12-2 and an end portion of the conical transition mechanism 12-4. The connection convex step 12-2, the transverse connection concave groove 12-1-1 and the longitudinal connection concave grooves 12-1-2 jointly fix the elastic retractor 2.

Referring to FIG. 18, during clinical use, first, through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, the support 11 of the tongue dorsum connection mechanism 1 is buried under the tongue mucosa, and the elastic-retractor tongue dorsum connection mechanism 12 is exposed out of the surface of the tongue mucosa. After 15 days to 60 days after the surgery, if the patient does not feel pain or discomfort when the tongue dorsum connection mechanism 1 is pulled by hand, retraction to the tongue dorsum can be carried out.

Step 2: According to different specific structures to be used for the tooth-side fastener 3, the selected tooth-side fastener 3 is mounted and fixed by using teeth, the alveolar bone, the maxilla, the mandible, or positions outside the maxilla and mandible lips as supporting and fixing points of the tooth-side fastener 3. In this embodiment, the used tooth-side fastener 3 is adhesively fixed to the outer side of teeth, as shown in FIG. 18.

Step 3: Before sleep, first, one end of the elastic retractor 2 is fixed to the elastic-retractor tongue dorsum connection mechanism 12 of the tongue dorsum connection mechanism 1 of the present invention, and then the other end of the elastic retractor 2 is fixed to the tooth-side fastener 3. By using the tooth-side fastener 3 as a fulcrum, the elastic retractor 2 exerts an elastic pull force on the tongue dorsum connection mechanism 1 of the present invention. Under the effect of an elastic restoring force of the elastic retractor 2, the collapsed tongue root is pulled up forward, so as to enlarge the airway at the glossopharyngeal portion, thereby achieving the objective of treating snoring or OSAHS, as shown in FIG. 18.

Step 4: After getting up, by using the elasticity of the elastic retractor 2, the tooth-side connection hole 22-1 of the elastic retractor 2 is enlarged, and the elastic retractor 2 is taken off from the tooth-side fastener 3. Similarly, the elastic retractor 2 is also separated and removed from the elastic-retractor tongue dorsum connection mechanism 12 of the tongue dorsum connection mechanism 1, so as to release retraction to the tongue dorsum, as shown in FIG. 18.

In this embodiment, the transverse connection concave groove 12-1-1 and the longitudinal connection concave grooves 12-1-2 can transversely and longitudinally fix the tongue-side connection mechanism 21 of the elastic retractor 2 of the elastic tongue-dorsum retraction device. Generally, the elastic retractor 2 has a strip-shaped structure, and when the tongue-side connection mechanism 21 of the elastic retractor 2 having a strip-shaped structure is a tongue-side connection hole 21-1, the tongue-side connection hole 21-1 is passed through the connection convex step 12-2 and then fixed into the transverse connection concave groove 12-1-1 under the connection convex step 12-2. Moreover, when the elastic retractor 2 having a strip-shaped structure is pulled tight toward the tooth side, since the four longitudinal connection concave grooves 12-1-2 are provided, the edge of the tongue-side connection hole 21-1 can be automatically locked in the longitudinal connection concave grooves 12-1-2 on the connection convex step 12-2, so as to achieve combined-type fixing through space intersection of the transverse connection concave groove 12-1-1 and the longitudinal connection concave grooves 12-1-2, as shown in FIG. 18-1 to FIG. 18-10.

In addition, the connection convex step 12-2 of the tongue dorsum connection mechanism 1 may be provided with two longitudinal connection concave grooves 12-1-2, three longitudinal connection concave grooves 12-1-2, or five longitudinal connection concave grooves 12-1-2, which may be selected according to specific clinical demands, as shown in FIG. 18-11, FIG. 18-12 and FIG. 18-13 respectively.

In addition to the form that the longitudinal connection concave grooves 12-1-2 are perpendicular to the transverse connection concave groove 12-1-1 according to this embodiment, the longitudinal connection concave groove 12-1-2 may also form a space intersection angle with the transverse connection concave groove 12-1-1, and the space intersection angle is generally 10° to 90°.

Embodiment 18-1: 4-Groove Thread-Type Tongue Dorsum Connection Mechanism of an Elastic Tongue-Dorsum Retraction Device of the Present Invention Referring to FIG. 18-2, FIG. 18-3 and FIG. 18-4, this embodiment still uses the optimized tongue dorsum connection mechanism 1 of Embodiment 18 where the connection convex step is provided with four longitudinal connection concave grooves, so that the elastic retractor 2 is desirably fixed and connected by means of the joint positioning function of the connection convex step 12-2, the longitudinal connection concave grooves 12-1-2 and the transverse connection concave groove 12-1-1; a difference between this embodiment and Embodiment 18 lies in that: the connection convex step 12-2 of the tongue dorsum connection mechanism 1 of this embodiment and the support 11 form a removable thread connection structure.

In this embodiment, the tongue dorsum connection mechanism 1 includes the support 11 and the elastic-retractor tongue dorsum connection mechanism 12 connected to the elastic retractor. The support 11 is an arc-shaped cylinder, and the elastic-retractor tongue dorsum connection mechanism 12 connected to the elastic retractor is formed by a connection convex step 12-2 and connection concave grooves 12-1. The connection convex step 12-2 is connected to an end portion of the support 11 through thread connection. A connecting nut 12-7 on the connection convex step 12-2 is screwed onto a connecting bolt 11-7 at the end portion of the support 11, thereby connecting the elastic-retractor tongue dorsum connection mechanism 12 to the support 11. On the contrary, the connecting nut 12-7 is rotated and unscrewed from the connecting bolt 11-7, thereby disconnecting the elastic-retractor tongue dorsum connection mechanism 12 from the support 11. The removable thread connection-type tongue dorsum connection mechanism is conveniently mounted under and removed from the mucosa of the tongue dorsum.

In this embodiment, the removable thread connection structure used at the left side of the tongue dorsum connection mechanism 1 achieves combined-type connection of the elastic-retractor tongue dorsum connection mechanism 12 and the support 11. The right side of the tongue dorsum connection mechanism 1 is integrally manufactured, thereby facilitating clamping and mounting using clamping pliers.

Embodiment 18-2: 4-Groove Concave-Convex Engagement-Type Tongue Dorsum Connection Mechanism of an Elastic Tongue-Dorsum Retraction Device of the Present Invention Referring to FIG. 18-5, FIG. 18-6 and FIG. 18-7, this embodiment still uses the optimized tongue dorsum connection mechanism 1 of Embodiment 18 where the connection convex step is provided with four longitudinal connection concave grooves, so that the elastic retractor 2 is desirably fixed and connected by means of the joint positioning function of the connection convex step 12-2, the longitudinal connection concave grooves 12-1-2 and the transverse connection concave groove 12-1-1; a difference between this embodiment and Embodiment 18 and Embodiment 18-1 lies in that: the connection convex step 12-2 of the tongue dorsum connection mechanism 1 of this embodiment and the support 11 form a removable concave-convex engagement structure.

Assembly can be completed simply by locking a concave-convex engagement mounting convex step 11-5 on the support 11 into a concave-convex engagement mounting convex groove 12-5 on the connection convex step 12-2 of the elastic-retractor tongue dorsum connection mechanism 12 connected to the elastic retractor. When releasing is required, the slot hole 11-6 on the support 11 is pressed inward to enable the slot hole 11-6 to shrink inward, so as to enable the concave-convex engagement mounting convex step 11-5 to shrink centripetally, so that the concave-convex engagement mounting convex step 11-5 can be released from the concave-convex engagement mounting convex groove 12-5, thereby completing removal.

Embodiment 19: Three-Stage Elastic Retractor of an Elastic Tongue-Dorsum Retraction Device of the Present Invention Referring to FIG. 19 to FIG. 19-2, an elastic retractor 2 for use in an elastic tongue-dorsum retraction device is disclosed in this embodiment, where the elastic retractor 2 is integrally made of a medical silica gel material by using a molding technology.

The three-stage elastic retractor 2 includes a tongue-side connection mechanism 21, a tooth-side connection mechanism 22 and an elastic deformation mechanism 20.

Figure 19:
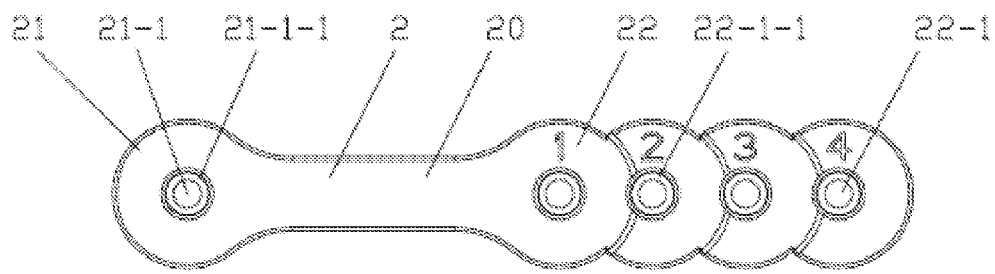
FIG. 19 is a schematic structural view of a three-stage elastic retractor of the present invention, where in this embodiment, the three-stage elastic refractor 2 includes a tooth-side connection mechanism 22, a tongue-side connection mechanism 21 and an elastic deformation mechanism 20, the tooth-side connection mechanism 22 is provided with four tooth-side connection holes 22-1, and the tongue-side connection mechanism 21 is provided with only one tongue-side connection hole 21-1.
Figures 1, 19:
Figures 2, 19:
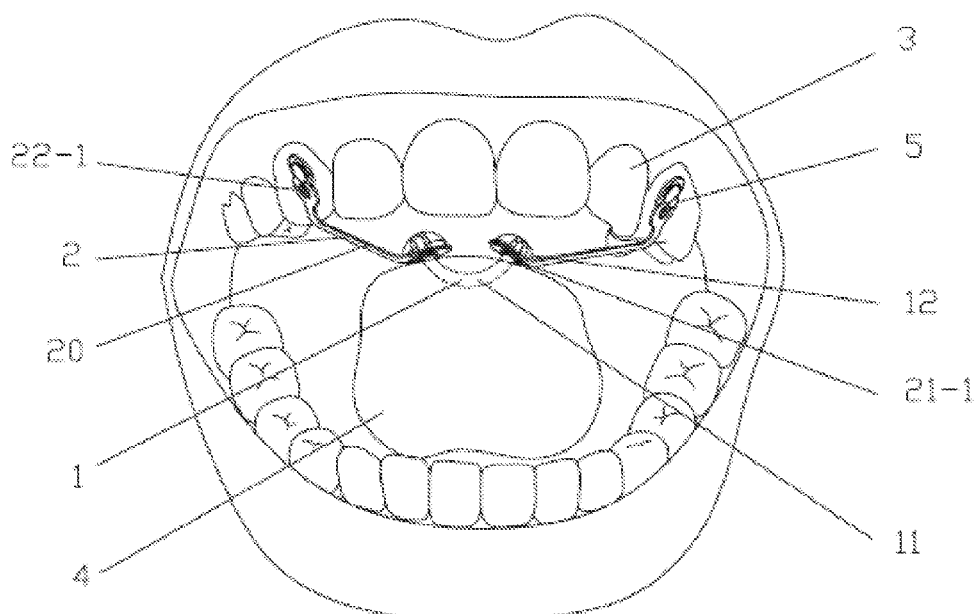

Referring to FIG. 19 to FIG. 19-1, the tongue-side connection mechanism 21 and the tooth-side connection mechanism 22 are separately disposed at two ends of the three-stage elastic retractor 2. The tongue-side connection mechanism 21 is provided with one tongue-side connection hole 21-1. The tooth-side connection mechanism 22 is provided with four tooth-side connection holes 22-1 for adjusting the magnitude of a retraction force of the three-stage elastic retractor, where the tooth-side connection holes 22-1 are arranged at an interval distance of about 3 mm to 5 mm. The elastic deformation mechanism 20 is disposed between the tongue-side connection mechanism 21 and the tooth-side connection mechanism 22.

The three-stage elastic retractor 2 is an elongated sheet-like elastic object. By means of the variable cross-section of the three-stage elastic retractor 2 integrally made of a medical elastic material, it is achieved that when the elastic deformation mechanism 20 undergoes elastic deformation, the tongue-side connection mechanism 21 or the tooth-side connection mechanism 22 almost does not undergo elastic deformation.

Further, a protruding edge 21-1-1 capable of increasing the tensile resistance is provided around the tongue-side connection hole 21-1 provided on the tongue-side connection mechanism 21. The protruding edge 21-1-1 can effectively encircle the tongue dorsum connection mechanism 2, so as to prevent the three-stage elastic retractor 2 from accidentally falling off from the tongue dorsum connection mechanism 1.

In this embodiment, the tooth-side connection mechanism 22 is provided with four tooth-side connection holes 22-1, where the tooth-side connection holes 22-1 are arranged at an interval distance of 5 mm, and a position number is marked near each tooth-side connection hole 22-1 by using an Arabic numeral. When the tooth-side connection holes 22-1 having different position numbers are fixed to the tooth-side fastener 3, the magnitude of the elastic retraction force of the three-stage elastic retractor 2 of the present invention to the tongue can be adjusted. The closer the tooth-side connection hole 22-1 is adjacent to the elastic deformation mechanism 20, the larger the generated elastic retraction force is when the tooth-side connection hole 22-1 is fixed to the tooth-side fastener 3. On the contrary, the more distant the tooth-side connection hole 22-1 is from the elastic deformation mechanism 20, the smaller the generated elastic retraction force is when the tooth-side connection hole 22-1 is fixed to the tooth-side fastener 3.

Further, a protruding edge 22-1-1 capable of increasing the tensile resistance is provided around each tooth-side connection hole 22-1. The protruding edge 22-1-1 can effectively encircle the tooth-side fastener 3, so as to prevent the three-stage elastic refractor 2 from accidentally falling off from the tooth-side fastener 3.

In a working state, the elastic deformation mechanism 20 undergoes elastic deformation, and exerts an elastic retraction force on the tongue, so that not only the collapsed tongue root can be pulled up forward to avoid OSAHS caused by collapse of the tongue root, but also movement of the tongue is not affected. In this way, good language ability is maintained while treating OSAHS, thereby improving comfort to the patient.

Further, the elastic retraction force exerted by the elastic deformation mechanism 20 in the working state on the tongue depends on individual differences and clinical treatment requirements of OSAHS patients, and the elastic retraction force is generally less than 300 g, and is usually 30 g to 200 g. The magnitude of the elastic retraction force of the elastic deformation mechanism 20 can be adjusted by using the tooth-side connection holes 22-1 having different position numbers in the tooth-side connection mechanism 22.

Referring to FIG. 19-2, during clinical use, first, the tongue dorsum connection mechanism 1 is implanted in front of circumvallate papillae of the tongue.

Through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, the tongue dorsum connection mechanism 1 is implanted and fixed, so that the support 11 of the tongue dorsum connection mechanism 1 is buried under the tongue mucosa, and the elastic-retractor tongue dorsum connection mechanism 12 is exposed out of the surface of the tongue mucosa. After 15 days to 60 days after the surgery, if the patient does not feel pain or discomfort when the surgically implanted tongue dorsum connection mechanism 1 is pulled by hand, retraction to the tongue dorsum can be carried out.

Step 2: The tooth-side fastener 3 is fixed.

Two tooth-side fasteners 3 are respectively fixed to the inner side of one upper tooth on the left and the inner side of one upper tooth on the right by using a medical adhesive. Generally, the fourth upper tooth counted leftward starting from incisors or the fourth upper tooth counted rightward starting from incisors is used as an adhesive fixing point of the tooth-side fastener 3.

Step 3: Before sleep, the three-stage elastic retractor 2 is worn.

Before sleep, the tongue-side connection mechanism 21 of the elastic retractor 2 is fixed to the tongue dorsum connection mechanism 1, the tooth-side connection mechanism 22 is fixed to the tooth-side fastener 3, and by using the tooth-side fastener 3 as a fulcrum, the elastic retractor 2 exerts an elastic pull force on the tongue dorsum connection mechanism 1. Under the effect of an elastic restoring force of the elastic retractor 2, the tongue is pulled up forward.

Step 4: After getting up, the three-stage elastic retractor 2 is removed.

After getting up, the three-stage elastic retractor 2 is taken off from the tooth-side fastener 3, and the three-stage elastic refractor 2 is also separated and removed from the tongue dorsum connection mechanism 1, so as to release retraction to the tongue dorsum.

Embodiment 20: Integral-Type Elastic Retraction Mechanism of an Elastic Tongue-Dorsum Retraction Device of the Present Invention Referring to FIG. 20 to FIG. 20-5, in this embodiment, the tongue dorsum connection mechanism 1 and the elastic retractor 2 of the tongue dorsum the elastic retraction mechanism of the present invention are combined to form an integral part, thereby forming the integral-type elastic retraction mechanism 212. The integral-type elastic retraction mechanism 212 includes the tongue dorsum connection mechanism 1 and the elastic retractor 2, and is integrally made of medical silica gel by using a molding technology.

Figure 20:
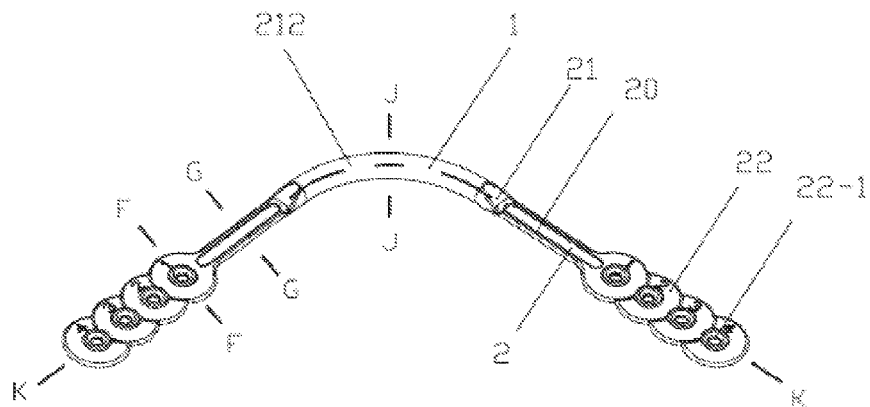
FIG. 20 is a schematic structural view of an integral-type elastic retraction mechanism of the present invention, where in this embodiment, the integral-type elastic retraction mechanism 212 includes two tooth-side connection mechanisms 22, one tongue dorsum connection mechanism 1 and two elastic deformation mechanisms 20, the tooth-side connection mechanism 22 is provided with four tooth-side connection holes 22-1, and the four tooth-side connection holes 22-1 are respectively used for adjusting the elastic restoring force of the elastic deformation mechanism 20.
Figures 1, 20:
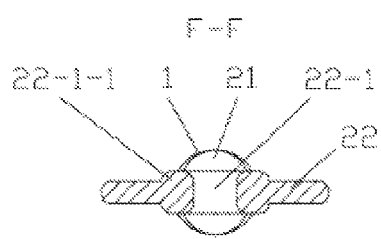
Figures 2, 20:
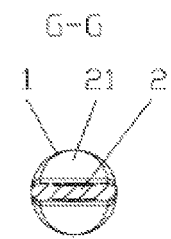
Figures 3, 20:
Figures 4, 20:
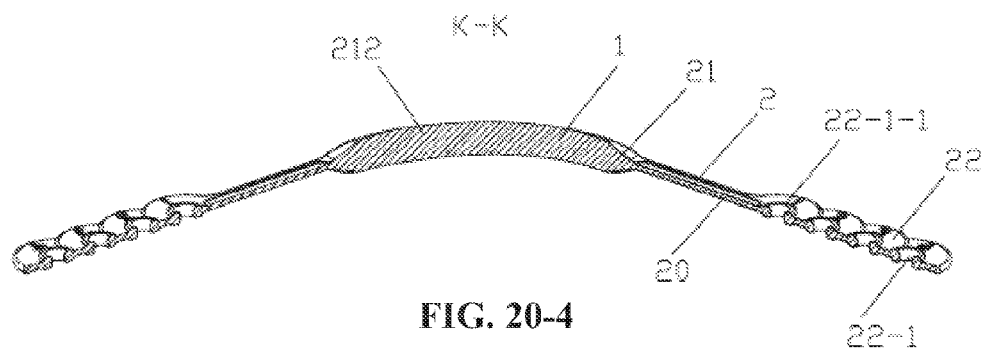
Figures 5, 20:
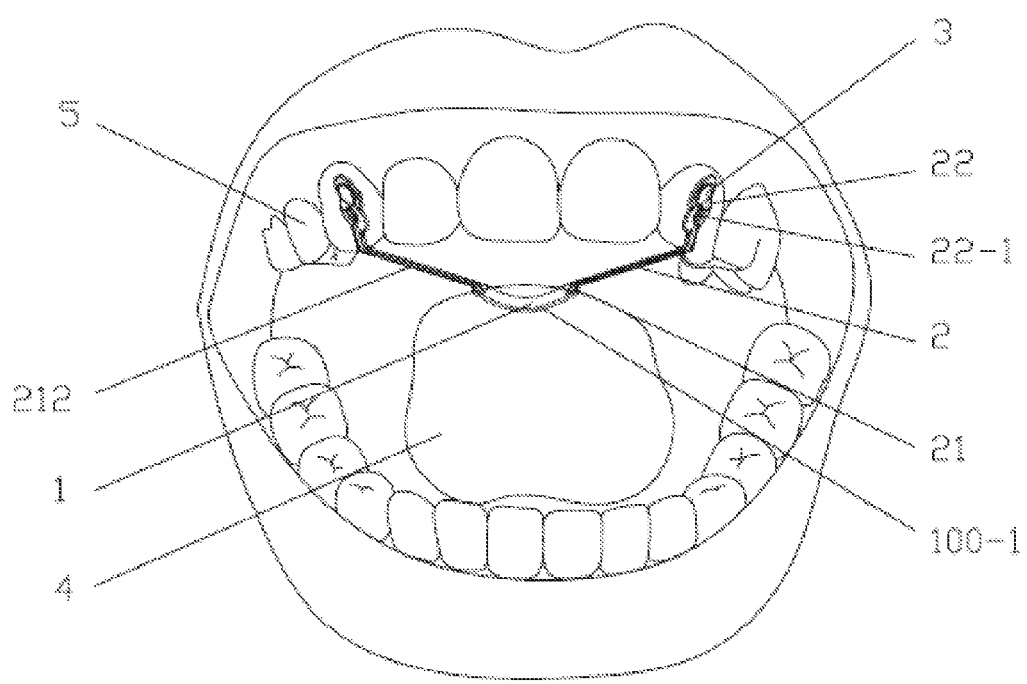

Referring to FIG. 20 to FIG. 20-4, the integral-type elastic retraction mechanism 212 of the present invention includes a tongue dorsum connection mechanism 1 and an elastic retractor 2. The elastic retractor 2 includes a tooth-side connection mechanism 22, an elastic deformation mechanism 20, and a tongue-side connection mechanism 21. The tooth-side connection mechanism 22, the elastic deformation mechanism 20, the tongue-side connection mechanism 21 and the tongue dorsum connection mechanism 1 of the integral-type elastic retraction mechanism 212 are arranged in the following order:

the tooth-side connection mechanism 22-the elastic deformation mechanism 20-the tongue-side connection mechanism 21-the tongue dorsum connection mechanism 1-the tongue-side connection mechanism 21-the elastic deformation mechanism 20-the tooth-side connection mechanism 22.

The integral-type elastic refraction mechanism 212 is based on a design concept of variable cross-section, so that under the same force conditions, various functional modules of the elastic body have different amounts of elastic deformation.

The area of the cross-section of the elastic deformation mechanism 20 is not only less than the area of the cross-section of the tooth-side connection mechanism 22, but also is less than the area of the cross-section of the tongue dorsum connection mechanism 1. In this embodiment, the area of the cross-section of the elastic deformation mechanism 20 is only 30% or less of the area of the cross-section of the tooth-side connection mechanism 22 or the tongue dorsum connection mechanism 1. In this embodiment, for the integral-type elastic retraction mechanism 212 of the present invention, under the same force conditions, the amount of elastic deformation of the elastic deformation mechanism 20 that undergoes elastic deformation reaches more than three times the amount of elastic deformation of the tooth-side connection mechanism 22 or the tongue dorsum connection mechanism 1. In other words, the deformation resistance of the elastic deformation mechanism 20 is less than the deformation resistance of the tooth-side connection mechanism 22 or the tongue dorsum connection mechanism 1.

In a working state in which a pull force of below 300 g is exerted on the integral-type elastic retraction mechanism 212, the elastic deformation mechanism 20 undergoes elastic deformation, and the tooth-side connection mechanism 22 or the tongue dorsum connection mechanism 1 almost does not undergo elastic deformation.

Further, the tooth-side connection mechanism 22 is provided with four tooth-side connection holes 22-1, where the tooth-side connection holes 22-1 are arranged at an interval distance of 5 mm, and a position number is marked near each tooth-side connection hole 22-1 by using an Arabic numeral. When the tooth-side connection holes 22-1 having different position numbers are fixed to the tooth-side fastener 3, the magnitude of an elastic retraction force of the integral-type elastic refraction mechanism 212 of the present invention to the tongue can be adjusted. The closer the tooth-side connection hole 22-1 is adjacent to the elastic deformation mechanism 20, the larger the generated elastic retraction force is when the tooth-side connection hole 22-1 is fixed to the tooth-side fastener 3. On the contrary, the more distant the tooth-side connection hole 22-1 is from the elastic deformation mechanism 20, the smaller the generated elastic retraction force is when the tooth-side connection hole 22-1 is fixed to the tooth-side fastener 3.

In addition, a protruding edge 22-1-1 capable of increasing the tensile resistance is provided around each tooth-side connection hole 22-1. The protruding edge 22-1-1 can effectively encircle the tooth-side fastener 3, so as to prevent the integral-type elastic retraction mechanism 212 from accidentally falling off from the tooth-side fastener 3.

In the working state, the elastic deformation mechanism 20 undergoes elastic deformation, and exerts an elastic retraction force on the tongue, so that the collapsed tongue root can be pulled up forward to avoid OSAHS caused by collapse of the tongue root. Since the elastic retraction manner is used, the pull force exerted by the integral-type elastic retraction mechanism 212 on the tongue dorsum is gentle and elastic, and movement of the tongue is not affected. In this way, good language ability is maintained while treating OSAHS, thereby improving comfort to the patient.

Further, the elastic retraction force exerted by the elastic deformation mechanism 20 in the working state on the tongue depends on individual differences and clinical treatment requirements of OSAHS patients, and the elastic retraction force is generally less than 300 g, and is usually 30 g to 200 g. The magnitude of the elastic retraction force of the elastic deformation mechanism 20 can be adjusted by using the tooth-side connection holes 22-1 having different position numbers in the tooth-side connection mechanism 22.

The tongue dorsum connection mechanism 1 of the integral-type elastic retraction mechanism 212 of the present invention is placed and maintained in an epithelialized tunnel 100-1 under the tongue mucosa of the tongue dorsum, and has an arc segment matching the under-the-tongue-mucosa epithelialized tunnel 100-1. In the working state, the tongue dorsum connection mechanism 1 almost does not undergo elastic deformation, and can effectively support and fix the under-the-tongue-mucosa epithelialized tunnel 100-1, so as to ensure the force receiving area of the tongue dorsum during retraction, thereby improving the effect of enlarging the airway at the glossopharyngeal portion.

During clinical use, first, an under-the-tongue-mucosa epithelialized tunnel 100-1 that can bear a certain pull force is formed under the tongue mucosa of the tongue dorsum.

Through a minimally invasive surgery under local anesthesia, on two sides that are about 0 cm to 5 cm in front of circumvallate papillae on the surface of the mucosa of the tongue dorsum and are at a distance of about 1 cm to 3 cm from the midline, a surgical instrument is used to perforate the tongue mucosa to form a tunnel. Then, an implant that can form an under-the-tongue-mucosa tunnel is implanted and fixed, so that two ends of the implant are exposed out of the tongue mucosa. After 15 days to 60 days after the surgery, after the implant is removed, the under-the-tongue-mucosa epithelialized tunnel 100-1 that can bear a certain pull force can be formed under the mucosa of the tongue dorsum.

Step 2: The tooth-side fastener 3 is fixed.

Two tooth-side fasteners 3 are respectively fixed to the fourth upper tooth counted leftward starting from incisors and the fourth upper tooth counted rightward starting from incisors by using a medical adhesive.

Step 3: Before sleep, the integral-type elastic retractor of the present invention is worn.

Before sleep, by using an auxiliary tool, the integral-type elastic retraction mechanism 212 is passed through the under-the-tongue-mucosa epithelialized tunnel 100-1 formed at the tongue dorsum. After the integral-type elastic retraction mechanism 212 is passed through the under-the-tongue-mucosa epithelialized tunnel 100-1, the tooth-side connection holes 22-1 having different position numbers may be selected according to individual differences of patients. In this embodiment, the tooth-side connection hole 22-1 having position number 2 is selected, and the tooth-side connection holes 22-1 at position 3 and position 4 are cut off along the mark line of position number 2. The two ends of the elastic retractor 2 are fixed to the tooth-side fastener 3 by the tooth-side connection hole 22-1, thereby completing the process of mounting and wearing the elastic tongue-dorsum retraction device of the present invention.

Step 4: After getting up, the integral-type elastic retractor of the present invention is removed.

The integral-type elastic retraction mechanism 212 is taken off from the tooth-side fastener 3, and drawn out from the under-the-tongue-mucosa epithelialized tunnel 100-1, so as to release retraction to the tongue dorsum.

Embodiment 21: Tripod-Type Tooth-Side Fastener that is Fixed Outside the Lip of an Elastic Tongue-Dorsum Retraction Device of the Present Invention Referring to FIG. 21 to FIG. 21-4, in this embodiment, a tooth-side fastener 3 of an elastic tongue-dorsum retraction device of the present invention is disclosed. The tooth-side fastener 3 uses a tripod structure, is fixed to mouth corners between the maxilla and the mandible, and is an outside-the-lip type tooth-side fastener 3. The outside-the-lip type tooth-side fastener 3 includes a support bracket 31 capable of supporting the outside-the-lip type tooth-side fastener 3, an elastic-retractor tooth-side connection mechanism 32 that can be connected to the elastic retractor 2, and a tooth-side fastening mechanism 33 capable of fixing the outside-the-lip type tooth-side fastener 3 to the outside of the maxilla and mandible. A surface of the tooth-side fastening mechanism 33 in contact with the skin surface is a smooth curved surface. The elastic-retractor tooth-side connection mechanism 32 and the tooth-side fastening mechanism 33 are disposed on the support bracket 31.

The elastic-retractor tooth-side connection mechanism 32 includes a positioning concave groove 32-1 and a positioning convex step 32-2 that are capable of fixing the tooth-side fastener of the elastic retractor 2, and the positioning convex step 32-2 uses a smooth conical structure.

The outside-the-lip type tooth-side fastener 3 includes three support brackets 31-4 fixed outside the lip, and the support bracket 31-4 fixed outside the lip is an arch structure. The support bracket 31-4 fixed outside the lip has one end intersecting with and connected to the elastic-retractor tooth-side connection mechanism 32, and the other end provided with the tooth-side fastening mechanism 33. The outside-the-lip type tooth-side fastener 3 forms a radiated arch structure that uses the elastic-retractor tooth-side connection mechanism 32 as the center, uses the support brackets 31-4 fixed outside the lip as arch-shaped supporting legs, and uses smooth curved surfaces 33-1 at the bottom of the tooth-side fastening mechanisms 33 that are in contact with the skin outside the maxilla and mandible as supporting points.

The outside-the-lip type tooth-side fastener 3 includes three support brackets 31-4 fixed outside the lip: a support bracket 31-4-1 fixed outside the maxilla lip, a support bracket 31-4-2 fixed outside the mandible lip, and a support bracket 31-4-3 at the lip corner. An angle $\gamma$ between the support bracket 31-4-1 fixed outside the maxilla lip and the support bracket 31-4-2 fixed outside the mandible lip is greater than or equal to an angle $\epsilon$ between the support bracket 31-4-1 fixed outside the maxilla lip and the support bracket 31-4-3 at the lip corner; the angle $\gamma$ between the support bracket 31-4-1 fixed outside the maxilla lip and the support bracket 31-4-2 fixed outside the mandible lip is greater than or equal to an angle $\theta$ between the support bracket 31-4-2 fixed outside the mandible lip and the support bracket 31-4-3 at the lip corner.

The length of the support bracket 31-4-1 fixed outside the maxilla lip or the support bracket 31-4-2 fixed outside the mandible lip is greater than or equal to the length of the support bracket 31-4-3 at the lip corner.

Figures 4, 21:
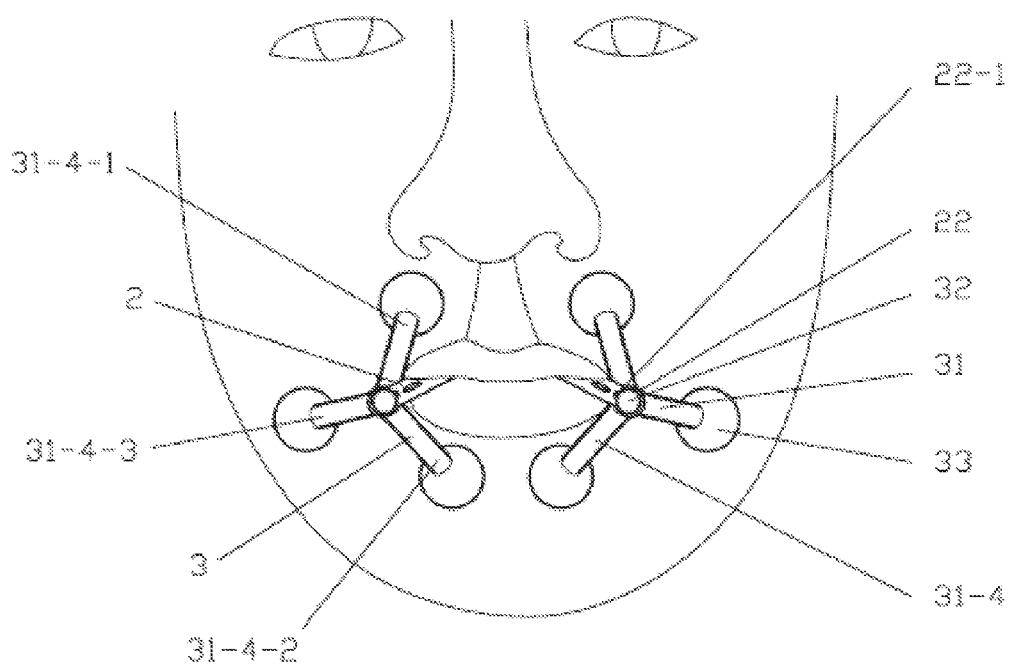

In a working state, the elastic retractor 2 is fixed in the positioning concave groove 32-1 by using the smooth conical structure of the positioning convex step 32-2, and for the outside-the-lip type tooth-side fastener 3, the support bracket 31-4-1 fixed outside the maxilla lip, the support bracket 31-4-2 fixed outside the mandible lip and the support bracket 31-4-3 at the lip corner are respectively supported outside the maxilla lip, outside the mandible lip and outside the lip corner, to form a triangular supporting structure. The outside-the-lip type tooth-side fastener 3 is fixed outside the maxilla and mandible of the patient by an elastic retraction force exerted by the elastic deformation mechanism 20 of the elastic retractor 2, thereby completing the process of wearing the elastic retractor 2 on the outside-the-lip type tooth-side fastener 3, as shown in FIG. 21-4.

Embodiment 22: I-Shaped Tooth-Side Fastener of an Elastic Tongue-Dorsum Retraction Device of the Present Invention Referring to FIG. 22 to FIG. 22-2, in this embodiment, a tooth-side fastener 3 of an elastic tongue-dorsum retraction device of the present invention is an I-shaped tooth-side fastener 3 that can be adhesively fixed to teeth. The tooth-side fastener 3 is formed by a support bracket 31, an elastic-retractor tooth-side connection mechanism 32 and a tooth-side fastening mechanism 33. The elastic-retractor tooth-side connection mechanism 32 and the tooth-side fastening mechanism 33 are disposed on the support bracket 31. The elastic-retractor tooth-side connection mechanism 32, the support bracket 31 and the tooth-side fastening mechanism 33 form an I-shaped cross-section. The tooth-side fastening mechanism 33 is adhesively fixed to the surface of teeth.

The tooth-side connection mechanism 32 includes a positioning concave groove 32-1 capable of fixing the elastic retractor 2 and a spherical crown-shaped positioning convex step 32-2 having a smooth surface. Since the tooth-side connection mechanism 32 uses the spherical crown-shaped design having a smooth surface, when the tooth-side connection mechanism 32 is fixed to the surface of teeth, contact between the tooth-side connection mechanism 32 and mucosa tissues in the oral cavity of the human body is smooth surface contact, which can minimize irritation to mucosa tissues in the oral cavity of the human body, thereby ensuring comfort to the patient in long-term use.

The support bracket 31 is a smooth column. When the elastic retractor 2 is connected to the tooth-side fastener 3 through the tooth-side connection mechanism 22, the tooth-side connection hole 22-1 of the tooth-side connection mechanism 22 can encircle the support bracket 31 and be embedded in the positioning concave groove 32-1. Since the support bracket 31 uses the design of a smooth column, the smooth surface does no harm to the tooth-side connection hole 22-1 of the elastic retractor 2, thereby improving safety of the elastic retractor 2 in use.

The tooth-side fastening mechanism 33 is a housing 33-1 having a radian matching the surface of teeth. Since the part of the tooth-side fastening mechanism 33 adhered to teeth has a radian matching the surface of teeth, the tooth-side fastening mechanism 33 can better conform to the surface of teeth, which better ensures the reliability of adhesion of the tooth-side fastening mechanism 33 to the surface of teeth, thereby improving safety of the tooth-side fastener 3 in use.

The housing 33-1 having a radian matching the surface of teeth of the tooth-side fastening mechanism 33 is provided with glue accommodating holes 33-1-1. Since the housing 33-1 of the tooth-side fastening mechanism 33 is provided with the glue accommodating holes 33-1-1, the contact area between the adhesive and the tooth-side fastening mechanism 33 during adhesion of the tooth-side fastening mechanism 33 to the surface of teeth can be increased, so that the tooth-side fastening mechanism 33 is adhered to the surface of teeth more firmly, thereby better ensuring safety of the tooth-side fastener 3 in use.

The tooth-side fastener 3 is made of a medical titanium alloy, which not only ensures biological safety of the material, so that no harmful effect will be produced upon the human body even in the case of long-term contact with human tissues, but also can ensure that mechanical properties of the material meet requirements, thereby ensuring safety of the tooth-side fastener 3 in long-term use by the patient.

Figure 22:
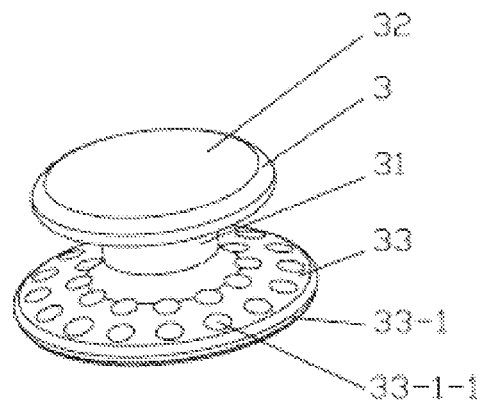
FIG. 22 is a three-dimensional schematic structural view of an I-shaped tooth-side fastener of the present invention.
Figures 1, 22:
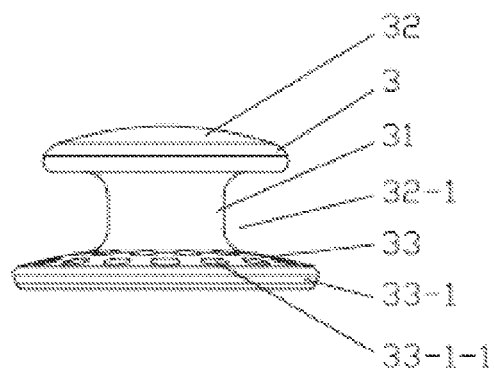
Figures 2, 22:
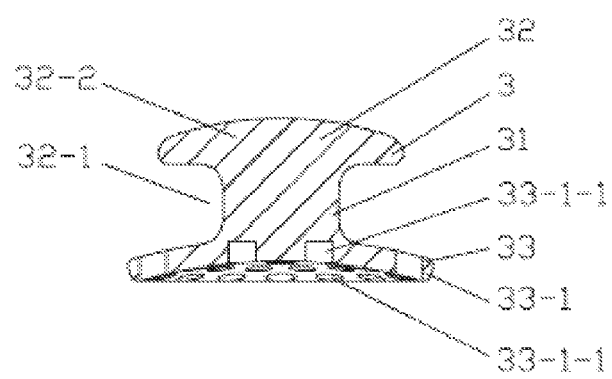
Figures 3, 22:
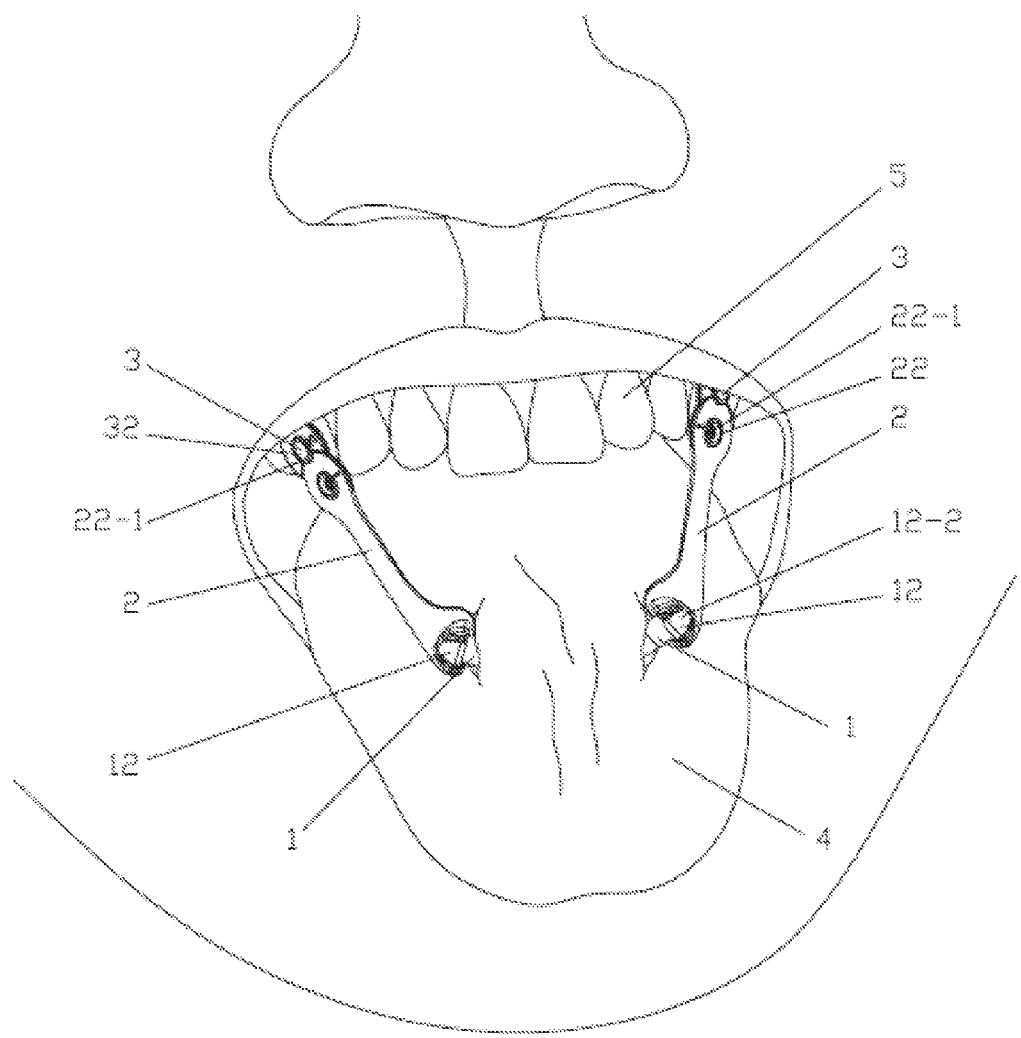

Referring to FIG. 22-3, in a working state, first, the tooth-side fastener 3 is adhered to the surface of teeth through the housing 33-1 having a radian matching the surface of teeth of the tooth-side fastening mechanism 33. After firm adhesion, the spherical crown-shaped positioning convex step 32-2 having a smooth surface of the elastic retractor 2 encircles the support bracket 31 and is embedded in the positioning concave groove 32-1, thereby completing the process of wearing the elastic retractor 2 on the tooth-side fastener 3.

Embodiment 23: Clamping Pliers for Mounting an Elastic Tongue-Dorsum Retraction Device of the Present Invention Referring to FIG. 23 to FIG. 23-15, in this embodiment, clamping pliers for mounting a 4-groove thread-type tongue dorsum connection mechanism 1 of an elastic tongue-dorsum retraction device of the present invention are disclosed. The clamping pliers 400 can be used in combination with the 4-groove thread-type tongue dorsum connection mechanism 1 of an elastic tongue-dorsum retraction device that is disclosed in Embodiment 18-1. The clamping pliers 400 include a right arm 401, a left arm 402, a rotating shaft 403, a restoring spring 404, a self-lock mechanism 405 and a mounting groove 406 for mounting the self-lock mechanism 405.

Figures 3, 23:
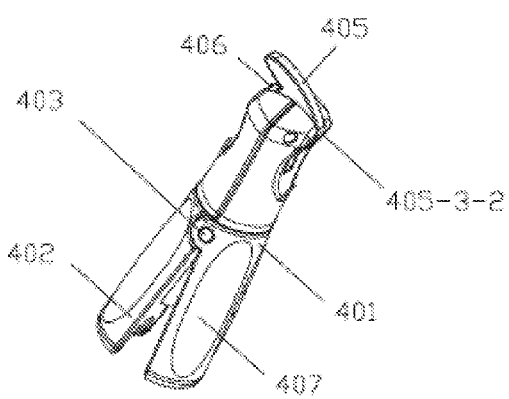
Figures 4, 23:
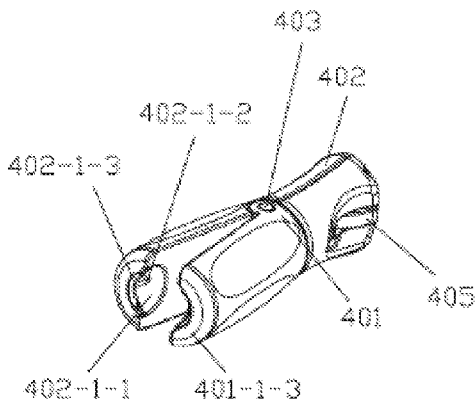
Figures 5, 23:
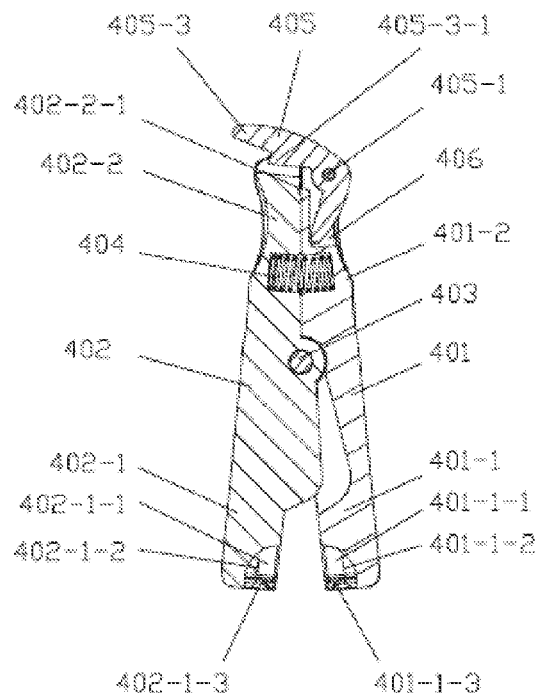
Figures 6, 23:
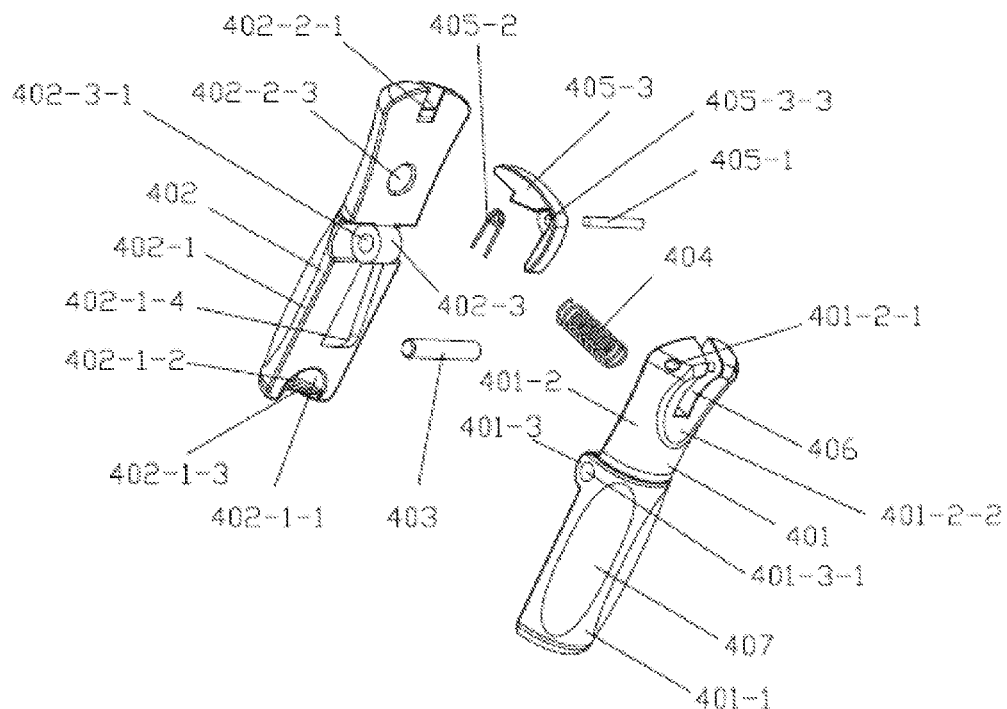
Figures 7, 23:
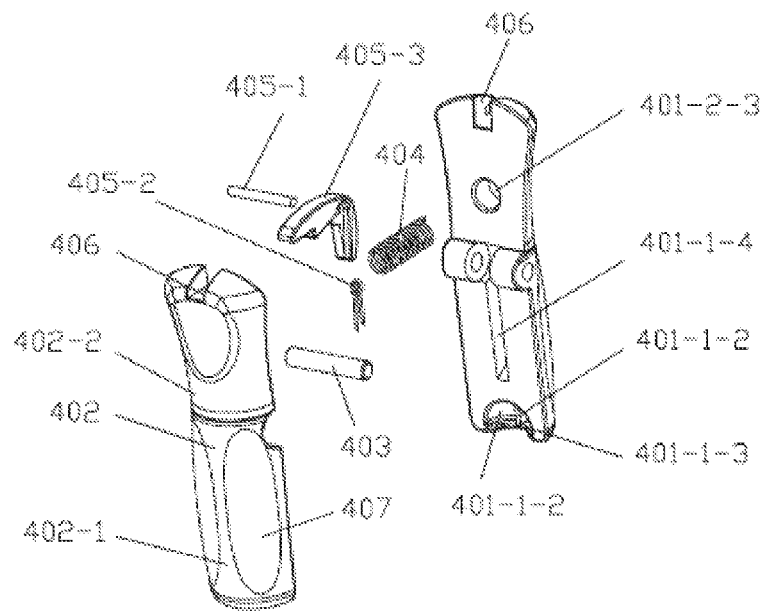
Figures 16, 23:
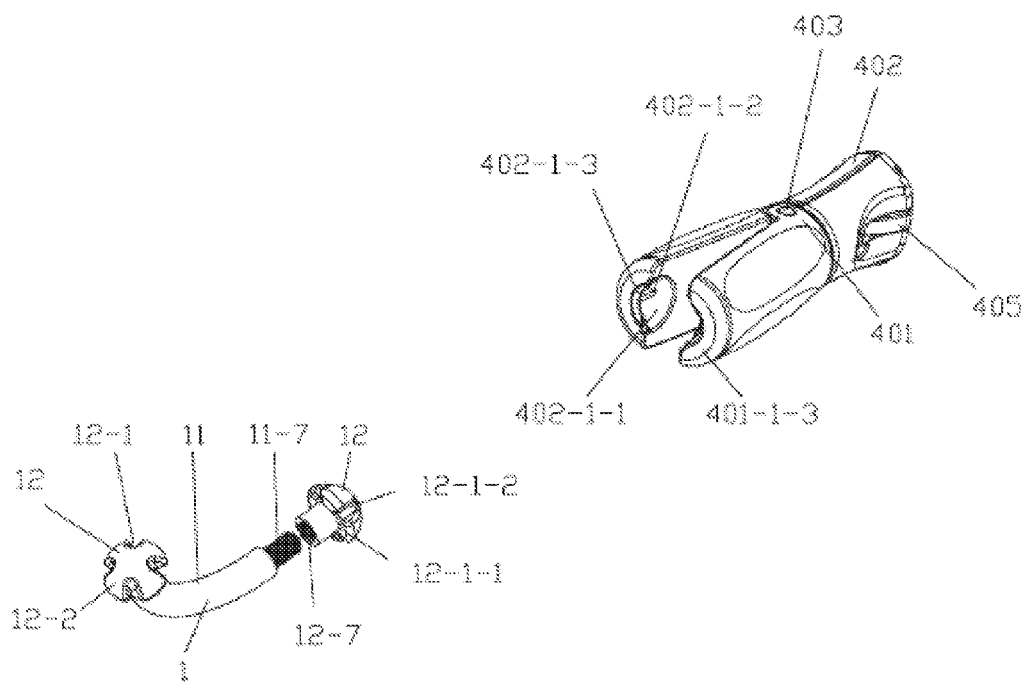
FIG. 23 is a schematic structural view of clamping pliers of the present invention in a closed state, where in this embodiment, a restoring spring 404 of the clamping pliers 400 is disposed between a right-arm tail 401-2 and a left-arm tail 402-2, and has one end supported on the right-arm tail 401-2, and the other end supported on the left-arm tail 402-2.
Figures 17, 23:
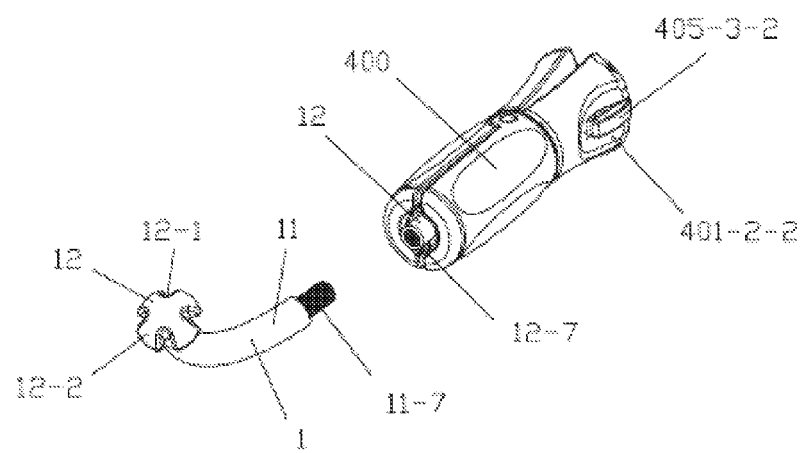
Figures 18, 23:
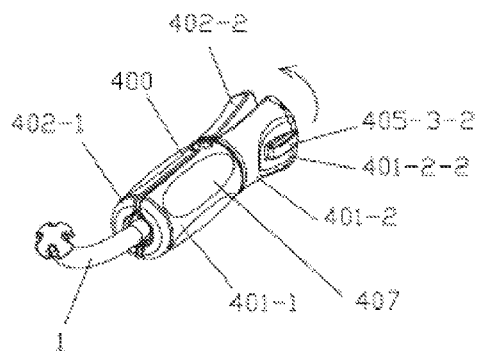
Figures 19, 23:
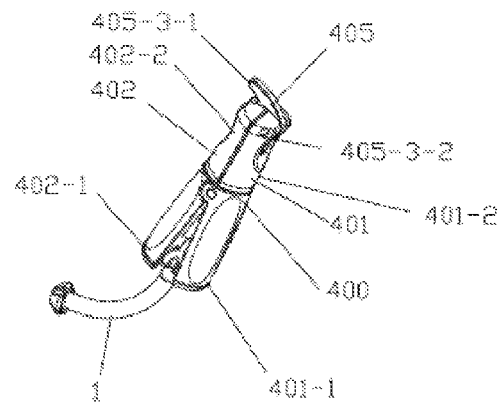
Figures 21, 23:
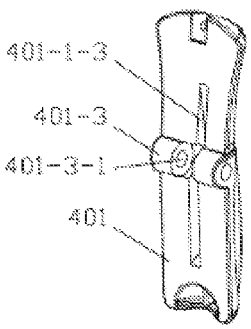
FIG. 21 is a schematic structural view of a tripod-type tooth-side fastener that is fixed outside the lip of the present invention.
Figures 20, 23:
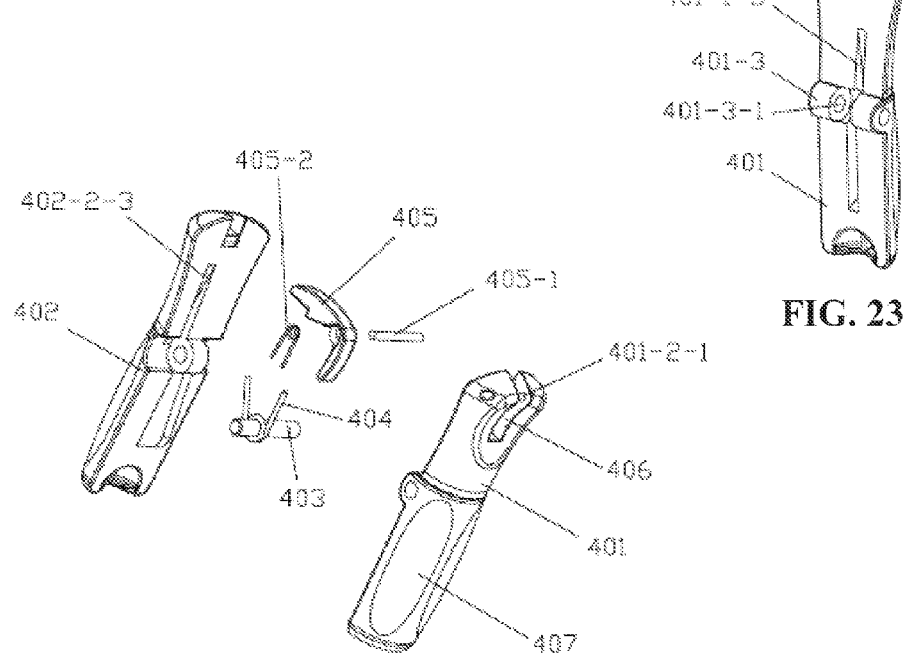

The right arm 401 includes a right clamp head 401-1, a right-arm tail 401-2, and a right-arm rotating-shaft mounting convex step 401-3. The right clamp head 401-1 includes a right working groove 401-1-1, right anti-detachment restricting convex steps 401-1-3, and one right rotation restricting convex step 401-1-2. The right-arm rotating-shaft mounting convex step 401-3 is provided with a through hole 401-3-1 for mounting the rotating shaft. The right-arm tail 401-2 is provided with a right restoring-spring mounting groove 401-2-3. The right arm 401 of the clamping pliers is further provided with a positioning and guiding groove 401-1-4. The mounting groove 406 is disposed at an end portion of the right-arm tail 401-2, as shown in FIG. 23.

The left arm 402 includes a left clamp head 402-1, a left-arm tail 402-2, and a left-arm rotating-shaft mounting convex step 402-3. The left clamp head 402-1 includes a left working groove 402-1-1, left anti-detachment restricting convex steps 402-1-3, and one left rotation restricting convex step 402-1-2. The left-arm rotating-shaft mounting convex step 402-3 is provided with a through hole 402-3-1 for mounting the rotating shaft. The left-arm tail 402-2 is provided with a left restoring-spring mounting groove 402-2-3. The left arm 402 of the clamping pliers is further provided with a positioning and guiding block 402-1-4. The mounting groove 406 is disposed at an end portion of the left-arm tail 402-2, as shown in FIG. 23

The rotating shaft 403 is a cylinder, and its diameter can form an interference fit with the through hole 401-3-1 on the right rotating-shaft mounting convex step, so as to fix the rotating shaft 403 to the through hole 401-3-1. The inner diameter of the through hole 402-3-1 on the left rotating-shaft mounting convex step is greater than the diameter of the rotating shaft 403, so that the left arm 402 can rotate around the rotating shaft 403 through the through hole 402-3-1, as shown in FIG. 23-6 and FIG. 23-7.

The restoring spring 404 of the clamping pliers 400 is a coil spring. The restoring spring 404 is disposed between the right-arm tail 401-2 and the left-arm tail 402-2, and has one end supported in the right restoring-spring mounting groove 401-2-3 of the right-arm tail 401-2, and the other end supported in the left restoring-spring mounting groove 402-2-3 of the left-arm tail 402-2. The restoring spring 404 exerts an opening force on the right-arm tail 401-2 and the left-arm tail 402-2, so that the clamp heads of the clamping pliers 400 are maintained in a closed state, as shown in FIG. 23-2, FIG. 23-5, FIG. 23-6 and FIG. 23-7.

The self-lock mechanism 405 of the clamping pliers 400 includes a pin 405-1, a torsion spring 405-2, and a self-lock positioning block 405-3, and is mounted in the mounting groove 406 of the self-lock mechanism of the clamping pliers 400.

Further, the pin 405-1 is a cylinder, forms an interference fit with the pin hole 401-2-1, and is firmly fixed.

The torsion spring 405-2 is wound on the pin 405-1, and the torsion spring 405-2 has one end supported on the right-arm tail 401-2, and the other end supported in the torsion-spring mounting groove 405-3-4 of the self-lock positioning block 405-3, to provide a downward closing force for a lock tooth 405-3-1 of the self-lock positioning block 405-3.

The self-lock positioning block 405-3 includes a lock tooth 405-3-1, a self-lock switch 405-3-2, a mounting through hole 405-3-3, and a torsion-spring mounting groove 405-3-4. The self-lock positioning block 405-3 has an L-shaped plate structure, where the lock tooth 405-3-1 is at a front end of the self-lock positioning block 405-3, the self-lock switch 405-3-2 is at the tail of the self-lock positioning block 405-3, the mounting through hole 405-3-3 is at the L-shaped corner of the self-lock positioning block 405-3, and the torsion-spring mounting groove 405-3-4 is adjacent to the mounting through hole 405-3-3. The lock tooth 405-3-1 forms concave-convex engagement with a positioning convex step 402-2-1 of the mounting groove 406 of the self-lock mechanism on the left-arm tail 402-2. The self-lock switch 405-3-2 protrudes out of an unlocking groove 401-2-2, and the pin 405-1 can be passed through the mounting through hole 405-3-3, so as to movably mount the self-lock positioning block 405-3 into the mounting groove 406 of the right arm 401, as shown in FIG. 23-2, FIG. 23-5, FIG. 23-6, FIG. 23-7, FIG. 23-14 and FIG. 23-15.

Assembly of the clamping pliers 400 is divided into two steps, namely, mounting of the main body of the clamping pliers 400, and mounting of the self-lock mechanism 405.

During assembly, first, mounting of the main body of the clamping pliers 400 is carried out. One end of the restoring spring 404 is disposed in the right restoring-spring mounting groove 401-2-3 of the right-arm tail 401-2. Then, the right arm 401 and the left arm 402 are assembled by means of concave-convex engagement of the right-arm rotating-shaft mounting convex step 401-3 and the left-arm rotating-shaft mounting convex step 402-3, and the other end of the restoring spring 404 is disposed in the left restoring-spring mounting groove 402-2-3 of the left-arm tail 402-2. After the right arm 401 and the left arm 402 are assembled, the rotating shaft 403 is sequentially passed through the through hole 401-3-1 on the right rotating-shaft mounting convex step and the through hole 402-3-1 on the left rotating-shaft mounting convex step, and then enters the through hole 401-3-1 on the right rotating-shaft mounting convex step; the rotating shaft 403 is fixed to the through hole 401-3-1 on the right rotating-shaft mounting convex step by interference fit. The inner diameter of the through hole 402-3-1 on the left rotating-shaft mounting convex step is greater than the diameter of the rotating shaft 403, so that the left arm 402 can rotate around the rotating shaft 403. Through the rotating shaft 403, the right arm 401 and the left arm 402 are assembled. In this way, assembly of the main body of the clamping pliers 400 is completed.

Next, assembly of the self-lock mechanism 405 is carried out. First, the pin 405-1 is inserted into the pin hole 401-2-1 of the right-arm tail 401-2, so that the pin 405-1 sequentially passes through the torsion spring 405-2 and the mounting through hole 405-3-3 of the self-lock positioning block 405-3, and then enters the pin hole 401-2-1. The pin 405-1 is fixed firmly by interference fit of the pin 405-1 and the pin hole 401-2-1. Since the inner diameter of the through hole 405-3-3 on the self-lock positioning block 405-3 is greater than the diameter of the pin 405-1, the self-lock positioning block 405-3 can rotate around the pin 405-1. Finally, one end of the torsion spring 405-2 is disposed in the torsion-spring mounting groove 405-3-4 of the self-lock positioning block 405-3, and the other end of the torsion spring 405-2 is supported on the right-arm tail 401-2. Under the effect of an elastic force of the torsion spring 405-3, the lock tooth 405-3-1 of the self-lock positioning block 405-3 is disposed in the positioning convex step 402-2-1 of the mounting groove 406 of the self-lock mechanism on the left-arm tail 402-2 to form concave-convex engagement, and form a downward closing force. In this way, assembly of the self-lock mechanism 405 is completed. Thus, assembly of the clamping pliers of the present invention is completed, as shown in FIG. 23-6 and FIG. 23-7.

Referring to FIG. 23-16 to FIG. 23-19, in use, first, the self-lock switch 405-3-2 of the self-lock positioning block is pressed down to lift the lock tooth 405-3-1 of the self-lock positioning block of the clamping pliers up from the positioning convex step 402-2-1 of the mounting groove of the self-lock mechanism on the left-arm tail, so that the clamp heads of the clamping pliers 400 are maintained in an open state. Then, the connection convex step 12-2 of the tongue dorsum connection mechanism is received in a cavity formed by the right working groove 401-1-1 and the left working groove 402-1-1 of the clamping pliers. When the clamping pliers 400 is being closed, the connection convex step 12-2 of the tongue dorsum connection mechanism is slightly rotated, so that the right rotation restricting convex step 401-1-2 and the left rotation restricting convex step 402-1-2 can be embedded in the longitudinal connection concave grooves 12-1-2 of the tongue dorsum connection mechanism 1, and the right anti-detachment restricting convex steps 401-1-3 and the left anti-detachment restricting convex steps 402-1-3 are embedded in the transverse connection concave groove 12-1-1 of the tongue dorsum connection mechanism 1. In this way, the preparatory work for screwing the connection convex step of the tongue dorsum connection mechanism into the support of the tongue dorsum connection mechanism through thread connection is finished.

The clamping pliers 400 are rotated, so as to fix the connecting nut 12-7 of the connection convex step 12-2 of the tongue dorsum connection mechanism 1 to the connecting bolt 11-7 of the support 11 of the tongue dorsum connection mechanism 1 through thread connection, thereby finishing the thread-connection mounting work.

The self-lock switch 405-3-2 of the self-lock positioning block is pressed down to lift the lock tooth 405-3-1 of the self-lock positioning block of the clamping pliers up from the positioning convex step 402-2-1 of the mounting groove of the self-lock mechanism on the left-arm tail, so that the clamp heads of the clamping pliers 400 are maintained in an open state. The clamping pliers of the present invention are withdrawn.

In addition, the technical solution provided by the present invention may also be specifically designed in other manners. For example, a torsion spring is used as the restoring spring 404 instead of the coil spring, the clamping pliers of the present invention may also be manufactured by winding a torsion-spring type restoring spring 404 onto the rotating shaft 403, with one end supported in the right restoring-spring mounting groove 401-2-3 of the right-arm tail 401-2 and the other end supported in the left restoring-spring mounting groove 402-2-3 of the left-arm tail 402-2, as shown in FIG. 23-20 and FIG. 23-21.

Embodiment 24: Installation Pliers for Mounting an Elastic Retractor of an Elastic Tongue-Dorsum Retraction Device of the Present Invention Referring to FIG. 24 to FIG. 24-3, in this embodiment, installation pliers 500 for mounting an elastic retractor of an elastic tongue-dorsum retraction device are disclosed. The installation pliers 500 can be used in combination with the three-stage elastic retractor in Embodiment 19 and the integral-type elastic retraction mechanism in Embodiment 20.

The installation pliers 500 include an opening end 501 and a handle end 502. The opening end 501 includes two symmetrically distributed brackets 501-1. A distance d501 between the two symmetrically distributed brackets 501-1 is greater than the greatest diameter of the connection convex step 12-2 of the elastic-retractor tongue dorsum connection mechanism 12.

The bracket 501-1 is provided with a groove 501-1-1 that can prevent the tongue-side connection mechanism 21 of the elastic retractor 2 from falling. After the tongue-side connection mechanism 21 of the elastic retractor 2 is disposed on the brackets 501-1 of the installation pliers 500, the tongue-side connection mechanism 21 of the elastic retractor 2 does not fall off from the installation pliers during movement of the installation pliers 500 because the grooves 501-1-1 on the brackets 501-1 of the installation pliers 500 provide a positioning function, thereby making the installation pliers 500 safer and more convenient in the working process.

A surface of the handle end 502 is provided with an anti-slip groove, an anti-slip fin or an anti-slip pattern 502-1, which can effectively prevent the installation pliers 500 from slipping out of the hand of the operator in use.

The installation pliers 500 are made of a medical polymer material, so that when the installation pliers 500 are used to mount the elastic retractor 2, no harmful effect will be produced upon the user even if the brackets 500-1 of the installation pliers 500 often directly contact tongue mucosa tissues of the human body.

Figures 4, 24:
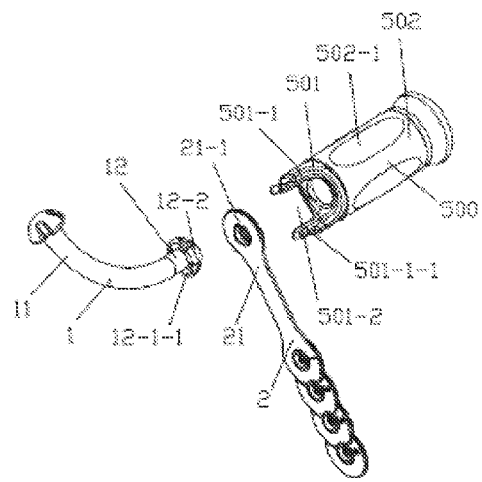
Figures 5, 24:
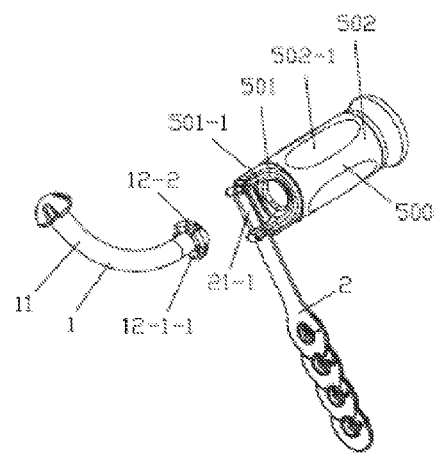
Figures 6, 24:
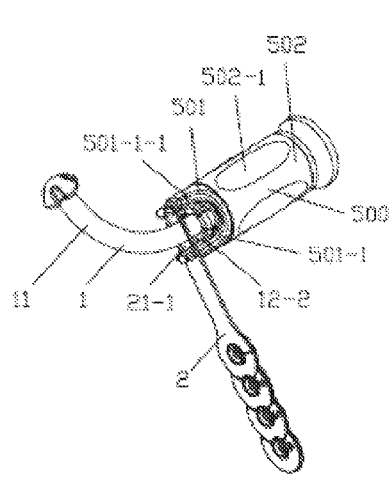
Figures 7, 24:
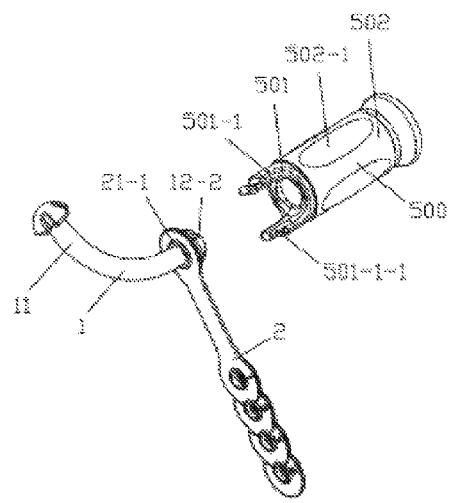
Figures 8, 24:
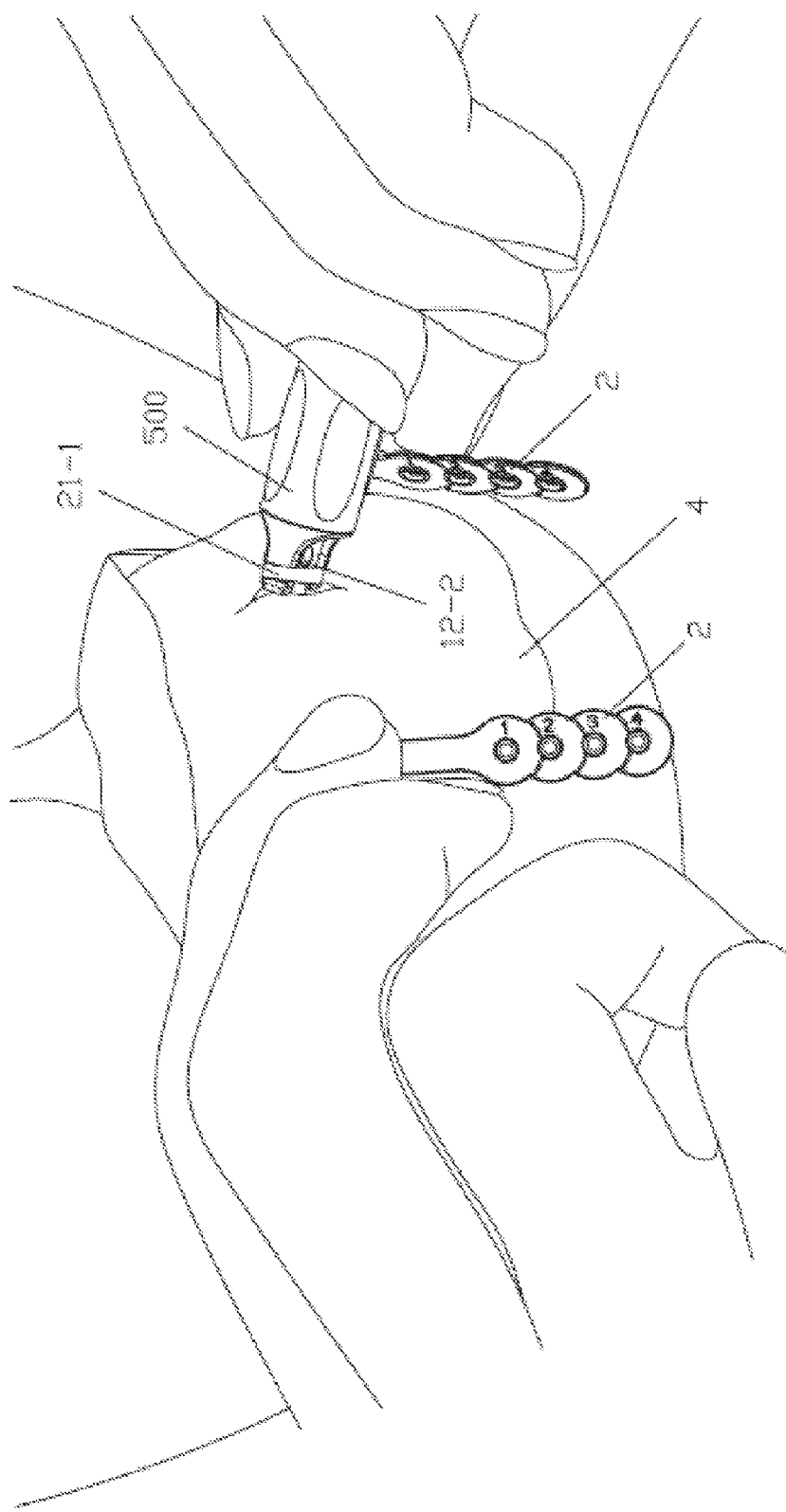

Referring to FIG. 24-4 to FIG. 24-8, when the installation pliers of the present invention are used to mount the elastic retractor 2, the tongue-side connection hole 21-1 of the elastic retractor 2 is elastically stretched and enlarged, and then sleeved over two symmetrical brackets 501-1. The handle end 502 of the installation pliers 500 is grasped, and the installation pliers 500 are moved to enable the tongue-side connection mechanism 21 of the elastic retractor 2 to approach the connection convex step 12-2 of the elastic-retractor tongue dorsum connection mechanism 12. The connection convex step 12-2 on the tongue dorsum connection mechanism 1 is disposed in the enlarged tongue-side connection hole 21-1. The installation pliers 500 are removed, so that the tongue-side connection hole 21-1 of the elastic retractor 2 slips off from the bracket 501-1, and is then embedded in the transverse connection concave groove 12-1-1 of the connection convex step 12-2 of the tongue dorsum connection mechanism 1. In this way, connection of the elastic retractor 2 to the tongue dorsum connection mechanism 1 is completed.

Figure 25:
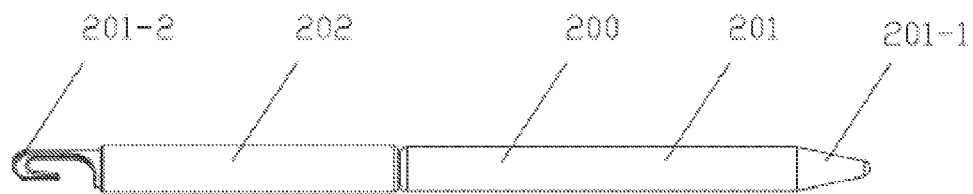
FIG. 25 is a schematic structural view of an integral-type elastic-retraction-mechanism line guide of the present invention.
Figures 1, 25:
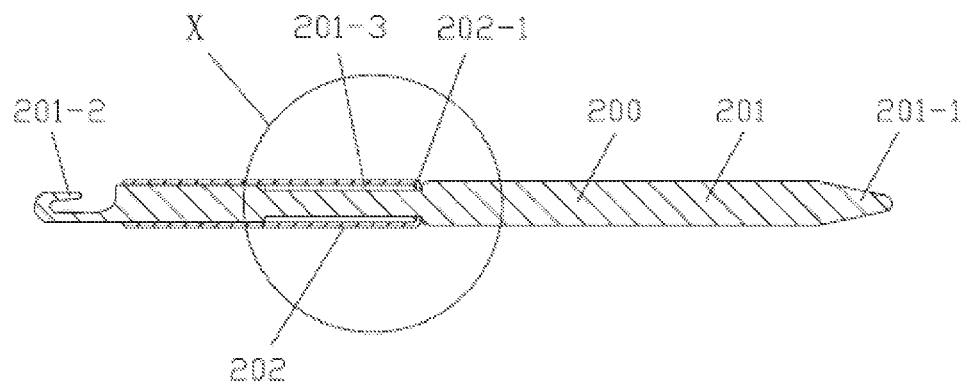
Figures 2, 25:
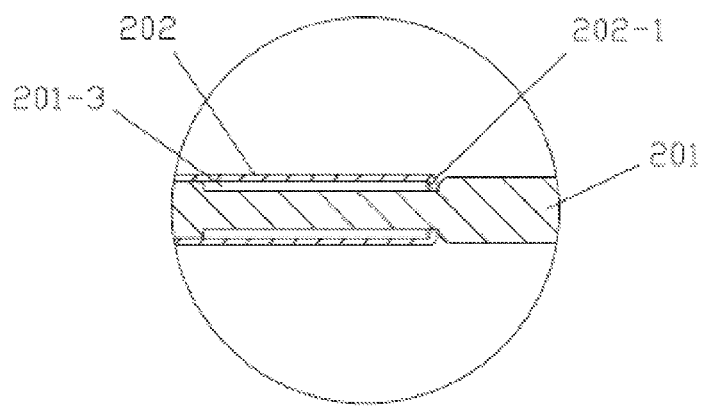
Figures 3, 25:
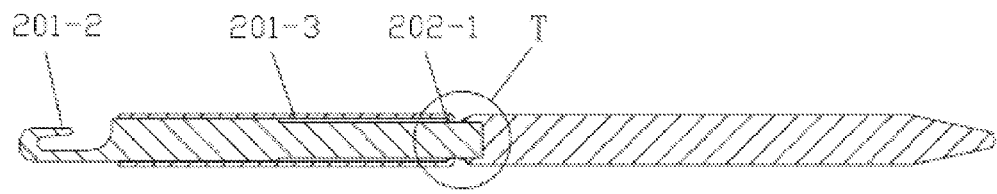
Figures 4, 25:
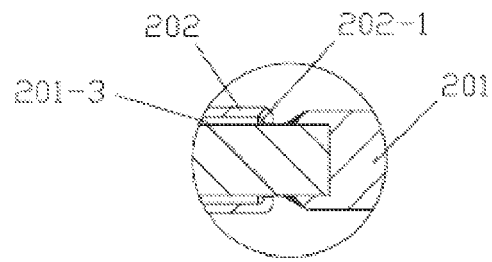
Figures 5, 25:
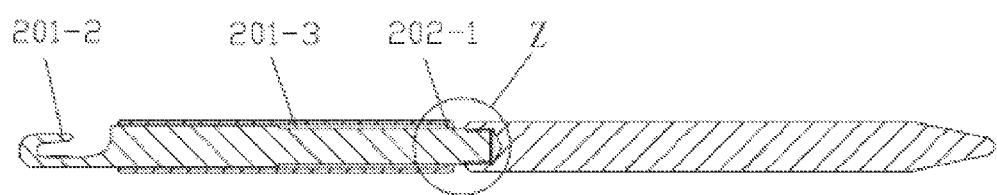
Figures 6, 25:
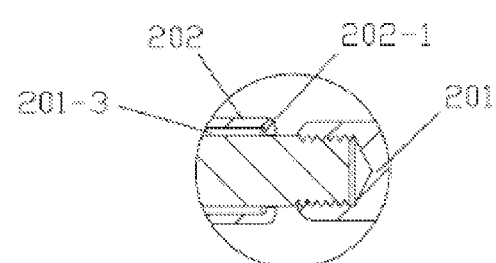

Embodiment 25: Line Guide for Mounting an Integral-Type Elastic Retraction Mechanism of an Elastic Tongue-Dorsum Retraction Device of the Present Invention Referring to FIG. 25 to FIG. 25-8, in this embodiment, a line guide 200 for mounting an integral-type elastic retraction mechanism of an elastic tongue-dorsum retraction device of the present invention is disclosed. The line guide 200 can be used in combination with the integral-type elastic retraction mechanism 212 of an elastic tongue-dorsum retraction device in Embodiment 20.

The line guide 200 for the integral-type elastic retraction mechanism includes a line guiding rod 201 and a slide block 202. The line guiding rod 201 includes a smooth guide head 201-1, a mounting hook 201-2 for mounting the elastic retractor 2, and a limiting groove 201-3 for limiting a sliding distance of the slide block 202. The slide block 202 includes a smoothly transitional sliding convex step 202-1, and the sliding convex step 202-1 of the slide block 202 can slide in the limiting groove 201-3 of the line guiding rod 201. When the sliding convex step 202-1 is located at one end of the limiting groove 201-3 adjacent to the guide head 201-1, the slide block 202 cannot cover the mounting hook 201-2; when the sliding convex step 202-1 is located at one end of the limiting groove 201-3 adjacent to the mounting hook 201-2, the slide block 202 can completely cover the mounting hook 201-2.

In a working state, first, the slide block 202 is slid to an end portion of the limiting groove 201-3 adjacent to the guide head 201-1, and the tooth-side connection hole 22-1 of the integral-type elastic retraction mechanism 212 is disposed in the mounting hook 201-2. Then, the slide block 202 is slid to an end portion of the limiting groove 201-3 adjacent to the mounting hook 201-2, and the mounting hook 201-2 is completely covered by the slide block 202. The assembled line guide 200 for the integral-type elastic retraction mechanism 212 is smoothly passed through the under-the-tongue-mucosa epithelialized tunnel 100-1 by using the guide head 201-1; after the integral-type elastic retraction mechanism 212 is guided out, the slide block 202 is slid to the end portion of the limiting groove 201-3 adjacent to the guide head 201-1 to expose the mounting hook 201-2; then, the tooth-side connection hole 22-1 of the integral-type elastic retraction mechanism 212 is removed from the mounting hook 201-2, thereby completing the process of guiding out the integral-type elastic retraction mechanism 212 by using the line guide 200.

Since the slide block 202 uses an inwardly flanged structure to form the sliding convex step 202-1, smooth transition of the sliding convex step 202-1 is achieved, which alleviates irritation to the mucosa on the surface of the tongue, and can improve comfort in the working process of the line guide 200.

The top end of the guide head 201-1 is a cone having a smooth surface; therefore, in the process of guiding out the integral-type elastic refraction mechanism 212 by using the line guide 200, the guide head 201-1 is in surface contact with the under-the-tongue-mucosa epithelialized tunnel 100-1, which can effectively alleviate irritation to the mucosa on the surface of the tongue. Moreover, when the line guide 200 is obstructed in the process of guiding out the integral-type elastic retraction mechanism 212, the guide head 201-1 can easily bypass the obstruction, thereby achieving a smooth guiding process.

In the working state, by sliding the slide block 202, the mounting hook 201-2 can be completely covered, and the integral-type elastic retraction mechanism 212 can be desirably fixed to the mounting hook 201-2, so that when the line guide 200 is passed through the under-the-tongue-mucosa epithelialized tunnel 100-1, the integral-type elastic retraction mechanism 212 does not fall off from the mounting hook 201-2. Moreover, since the mounting hook 201-2 is not exposed out of the slide block 202, the mounting hook 201-2 is effectively prevented from directly contacting and irritating the surface of the tongue mucosa, thereby greatly improving comfort and smoothness of the guiding process.

The embodiments introduced above are not unique structures for implementing the present invention. Persons skilled in the art should know that these embodiments are merely described by way of example, and persons skilled in the art may make various changes, improvements, and replacements without departing from the present invention.

Figure 26:
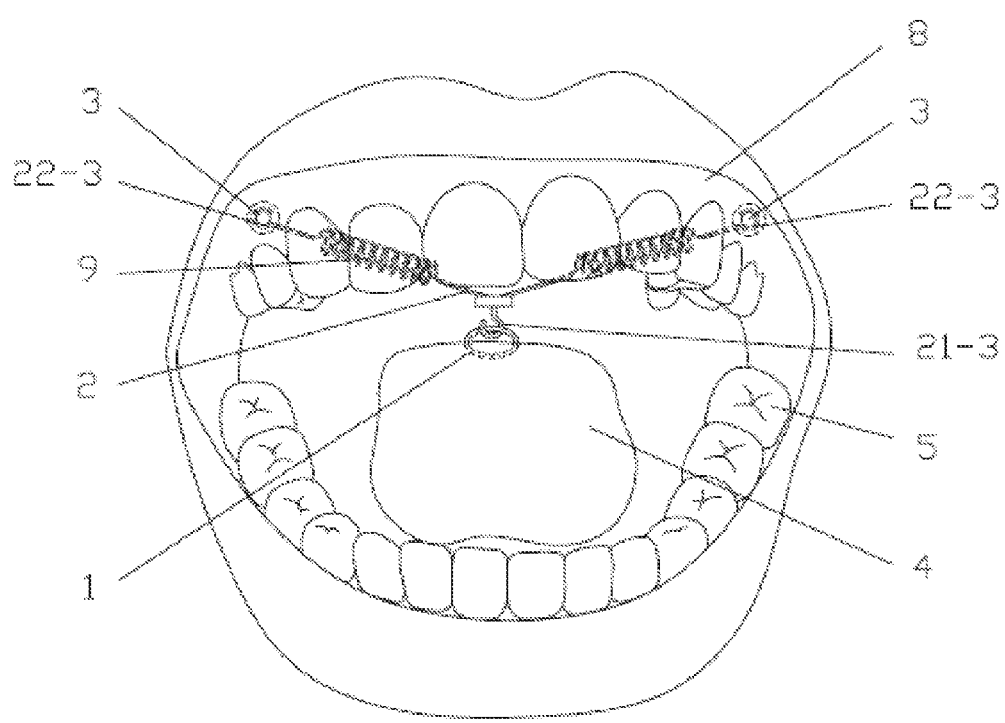
FIG. 26 is a schematic structural view of an elastic tongue-dorsum retraction device of the present invention that includes a spring and is fixed to the inner side of the alveolar bone by using a dental nail.

For example, in FIG. 26, an elastic tongue-dorsum retraction device of the present invention that is fixed to the inner side of gums by using a dental nail is shown. The elastic retractor 2 is made of a medical titanium-nickel shape memory alloy wire. The elastic retractor 2 includes a coil spring 9. The tongue-side connection mechanism 21 of the elastic retractor 2 uses a tongue-side connecting hook 21-3. The tooth-side connection mechanism 22 of the elastic retractor 2 also uses a tooth-side connecting hook 22-3. The tongue dorsum connection mechanism 1 is an elliptical ring-shaped support bracket, and the tongue-side connecting hook 21-3 can be conveniently hooked to the tongue dorsum connection mechanism 1. The elastic tongue-dorsum refraction device of the present invention having this structure is quite convenient to use.

Figures 1, 27:
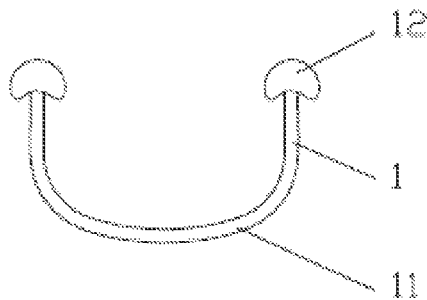
Figures 2, 27:
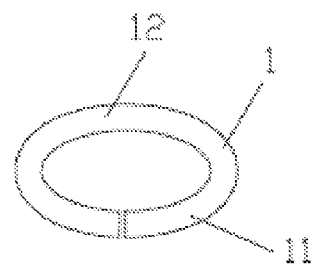
Figures 3, 27:
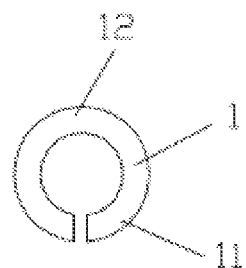
Figures 4, 27:
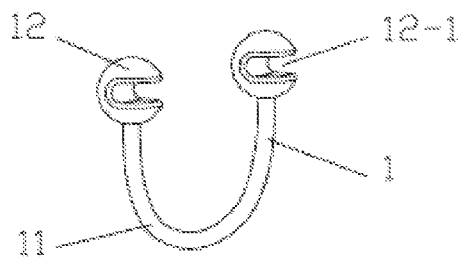
Figures 5, 27:
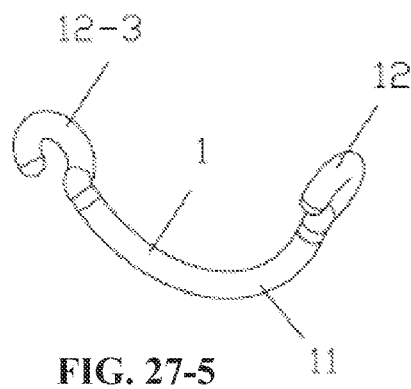
Figures 6, 27:
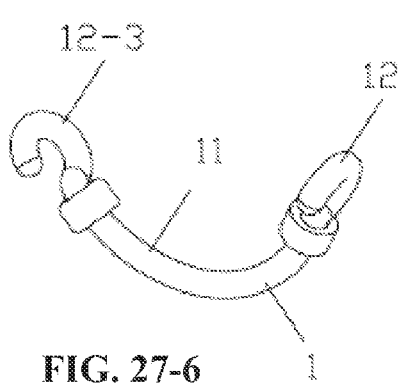
Figures 7, 27:
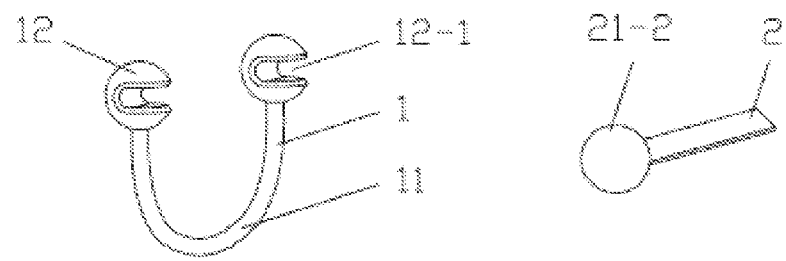
Figures 8, 27:
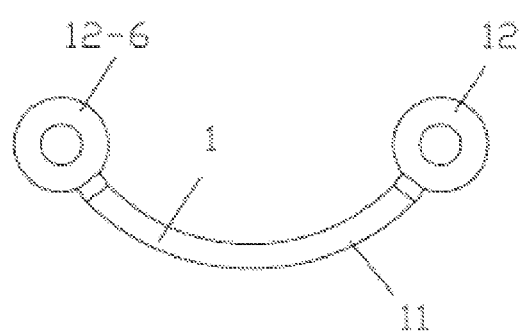
Figures 9, 27:
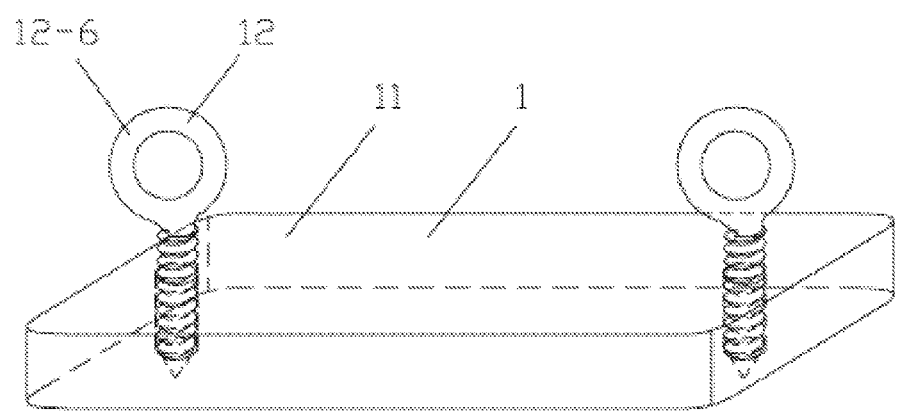

In the Following Embodiments, Some Changes to the Tongue Dorsum Connection Mechanism 1 are Shown:

Referring to FIG. 27-1, a tongue dorsum connection mechanism 1, which has a U-shaped support, of a tongue dorsum retraction device of the present invention is shown herein. The support 11 of the tongue dorsum connection mechanism 1 having a U-shaped support is U-shaped, and the elastic-retractor tongue dorsum connection mechanism 12 is a connection convex step 12-2. The connection convex step 12-2 and the support 11 are integrally manufactured. Moreover, the connection convex step 12-2 may also be manufactured as an independent part, and then fixed to two ends of the U-shape of the support 11 by thread connection, concave-convex engagement, interference fit, or adhesion.

Referring to FIG. 27-2, a tongue dorsum connection mechanism 1, which has an elliptical ring-shaped support, of a tongue dorsum retraction device of the present invention is shown herein. The tongue dorsum connection mechanism 1 is formed by bending a same titanium metal wire, a part of the elliptical ring shape that is implanted under the tongue mucosa forms the support 11 of the tongue dorsum connection mechanism 1, and a part of the elliptical ring shape that is exposed out of the tongue mucosa forms the elastic-refractor tongue dorsum connection mechanism 12 of the tongue dorsum connection mechanism 1.

Referring to FIG. 27-3, a tongue dorsum connection mechanism 1, which has a circular ring-shaped support, of a tongue dorsum retraction device of the present invention is shown herein. The tongue dorsum connection mechanism 1 is formed by bending a same titanium metal wire, a part of the circular ring shape that is implanted under the tongue mucosa forms the support 11 of the tongue dorsum connection mechanism 1, and a part of the circular ring shape that is exposed out of the tongue mucosa forms the elastic-retractor tongue dorsum connection mechanism 12 of the tongue dorsum connection mechanism 1.

Referring to FIG. 27-4, a difference between this embodiment and the embodiment of FIG. 27-1 lies in that: the elastic-retractor tongue dorsum connection mechanism 12 of the tongue dorsum connection mechanism 1 uses connection concave grooves 12-1. A strip-shaped elastic retractor 2 made of a medical film can be conveniently fixed to the connection concave grooves 12-1, and can also be conveniently removed from the connection concave grooves 12-1.

Referring to FIG. 27-5, a difference between this embodiment and the embodiment of FIG. 27-1 lies in that: the elastic-retractor tongue dorsum connection mechanism 12 of the tongue dorsum connection mechanism 1 uses connecting hooks 12-3. The tongue dorsum connection mechanism 1 is formed by bending a single titanium metal wire. An arc-shaped support 11 is implanted under the tongue mucosa, and the connecting hooks 12-3 at two ends are exposed out of the tongue mucosa. A strip-shaped elastic retractor 2 made of a medical film can be conveniently fixed to the connecting hooks 12-3, and can also be conveniently removed from the connecting hooks 12-3.

Referring to FIG. 27-6, a difference between this embodiment and the embodiment of FIG. 27-5 lies in that: the elastic-retractor tongue dorsum connection mechanism 12 of the tongue dorsum connection mechanism 1 uses connecting hooks 12-3. An arc-shaped support 11 of the tongue dorsum connection mechanism 1 is formed by bending a single titanium metal wire, and is implanted under the tongue mucosa. The connecting hooks 12-3 at two ends are connected to the support 11 by using screws, and are exposed out of the tongue mucosa.

Referring to FIG. 27-7, in this embodiment, the elastic-retractor tongue dorsum connection mechanism 12 of the tongue dorsum connection mechanism 1 uses a connection concave groove 12-1. The tongue-side connection mechanism 21 on the elastic refractor 2 uses a tongue-side connection convex step 21-2. The tongue-side connection convex step 21-2 is embedded in the connection concave groove 12-1 of the tongue-side fastener, thereby forming a removable fixed connection.

Referring to FIG. 27-8, in this embodiment, the elastic-retractor tongue dorsum connection mechanism 12 of the tongue dorsum connection mechanism 1 uses connecting rings 12-6. The connecting rings 12-6 are disposed at two ends of the support 11. The connecting rings 12-6 and the support 11 may be manufactured by integral molding, connected together by threads, or connected together by concave-convex engagement.

Figures 9, 18:
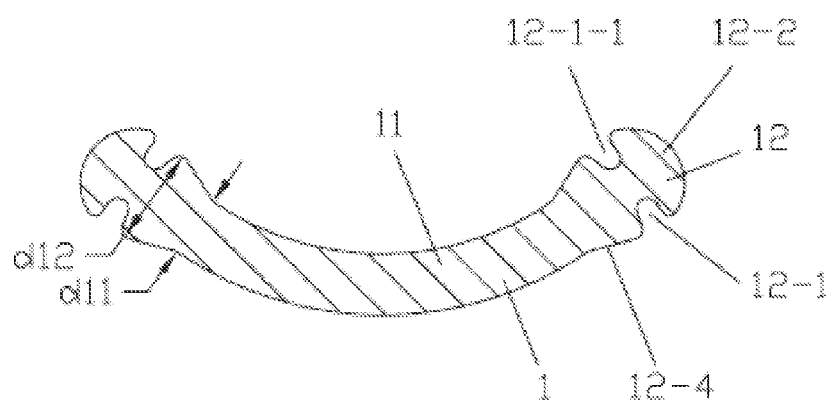
FIG. 9 is a schematic structural view of an elastic tongue-dorsum retraction device of the present invention that is adjustable through an elastic retractor.
Figures 10, 18:
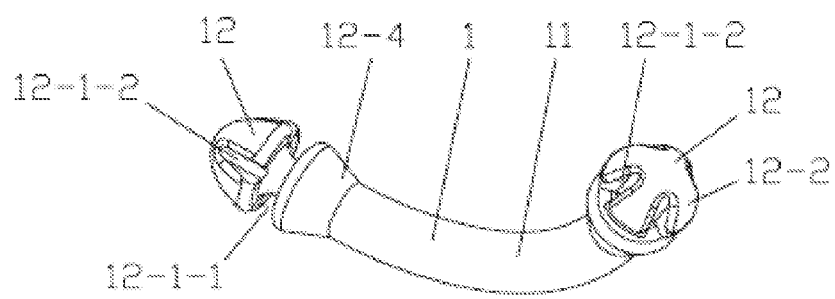
FIG. 10 is a schematic structural view of an under-the-tongue-mucosa epithelialized tunnel-type elastic tongue-dorsum retraction device of the present invention.
Figures 11, 18:
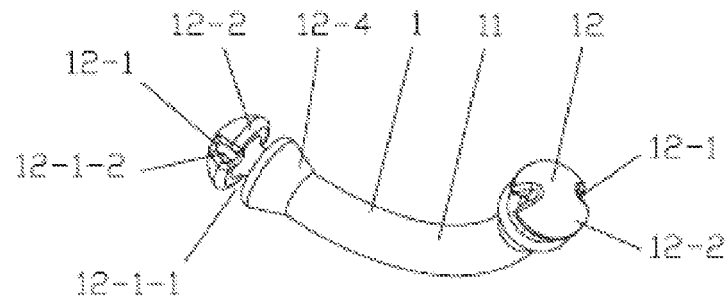
FIG. 11 is a schematic structural view of an under-the-tongue-mucosa tunnel-type elastic tongue-dorsum retraction device of the present invention that includes a thin-walled tube-shaped object.
Figures 12, 18:
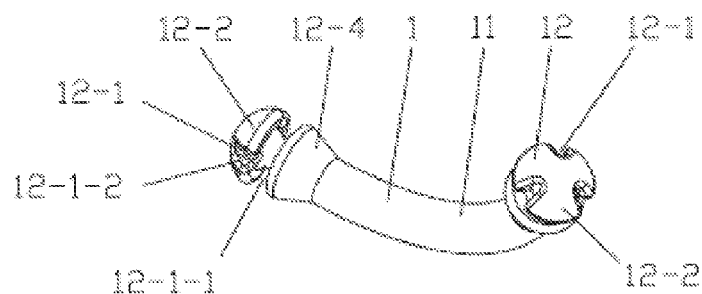
FIG. 12 is a schematic structural view of a coil spring-shaped under-the-tongue-mucosa tunnel-type elastic tongue-dorsum retraction device of the present invention.
Figures 13, 18:
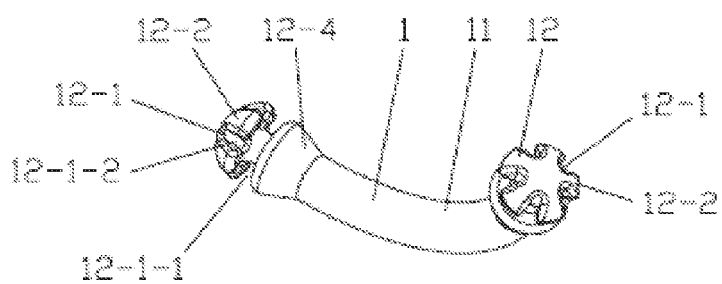

Referring to FIG. 27-9, in this embodiment, the elastic-retractor tongue dorsum connection mechanism 12 of the tongue dorsum connection mechanism 1 uses a connecting ring 12-6. The support 11 is a smoothly transitional strip, and two end portions of the support 11 are each provided with a threaded hole. The connecting ring 12-6 is connected to the threaded hole of the support 11 through a threaded rod at a lower end of the connecting ring 12-6, so that the connecting ring 12-6 is exposed out of the mucosa of the tongue dorsum, and the support 11 and the threaded rod of the connecting ring 12-6 are implanted under the mucosa of the tongue dorsum. Since the support 11 uses a smoothly transitional strip-shaped structure, the support is in surface contact with tissues of the tongue body, which increases the contact area. Therefore, when the elastic retractor 2 exerts an elastic retraction force on the tongue dorsum connection mechanism 1 to retract the tongue, the support 11 does not produce a cutting effect on the tissues of the tongue body, thereby ensuring safety and comfort of the elastic tongue-dorsum refraction device of the present invention in long-term use.

Figures 1, 2, 3, 28:
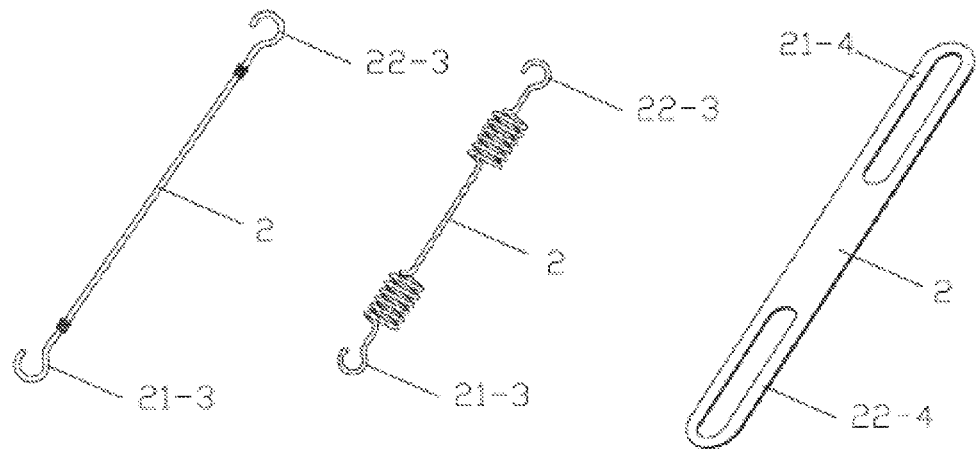
Figures 4, 5, 28:
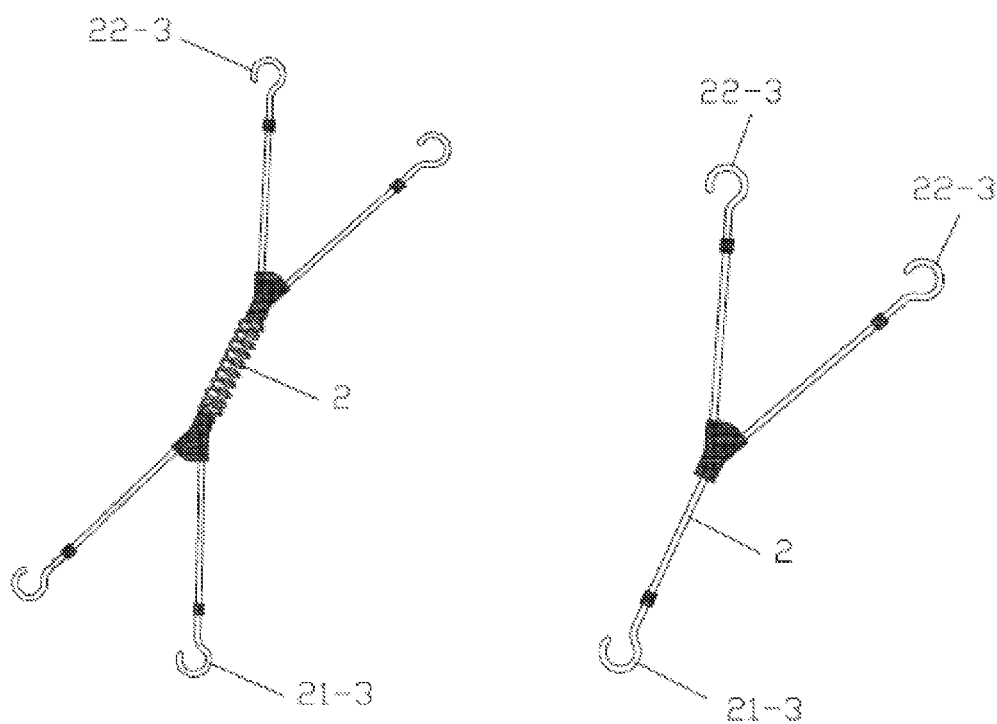

In the Following Embodiments, Some Changes to the Elastic Retractor 2 are Shown:

Referring to FIG. 28-1, in this embodiment, two ends of the elastic retractor 2 are a tooth-side connecting hook 22-3 and a tongue-side connecting hook 21-3.

Referring to FIG. 28-2, in this embodiment, the elastic retractor 2 is made of a single medical spring wire, and includes two coil springs 9. Two ends are respectively the tooth-side connecting hook 22-3 and the tongue-side connecting hook 21-3.

Referring to FIG. 28-3, in this embodiment, one end of the elastic retractor 2 is provided with a tongue-side connecting line 21-4, and the other end of the elastic retractor 2 is provided with a tooth-side connecting line 22-4. The tongue-side connecting line 21-4 can be conveniently wound on the connection concave groove 12-1, the connection convex step 12-2, or the connecting hook 12-3 of the tongue dorsum connection mechanism 1. The tooth-side connecting line 22-4 can be conveniently wound on the connection concave groove 32-1, the connection convex step 32-2, or the positioning hook 32-3 of the tooth-side fastener 3. The tongue-side connecting line 21-4 and the tooth-side connecting line 22-4 are integrally made of a medical latex film or medical silica gel.

Referring to FIG. 28-4, in this embodiment, the elastic retractor 2 includes one coil spring 9 at its middle part, the tooth-side end of the elastic retractor 2 includes two tooth-side connecting hooks 22-3, and the tongue-side end of the elastic retractor 2 includes two tongue-side connecting hooks 21-3. The tooth-side connecting hooks 22-3 and the tongue-side connecting hooks 21-3 are fixed to the coil spring 9 by riveting.

Referring to FIG. 28-5, in this embodiment, the elastic retractor 2 includes three elastic wire-like objects, where two of the elastic wire-like objects each have one end connected to the tooth-side connecting hook 22-3 by riveting or adhesion, the third elastic wire-like object has one end connected to the tongue-side connecting hook 21-3 by riveting or adhesion, and ends of the three elastic wire-like objects are connected to each other by riveting or adhesion, so that the whole elastic retractor 2 forms a Y-shape.

In the Following Embodiments, Some Changes to the Manner of Connection Between the Elastic Retractor 2 and the Tooth-Side Fastener 3 are Shown:

Referring to FIG. 29-1 and FIG. 29-2, the tooth-side fastener 3 includes a dental bone nail-type fixing support bracket 31-2, and the dental bone nail-type fixing support bracket 31-2 is made of ferromagnetic medical stainless steel. The elastic-retractor tooth-side connection mechanism 32 uses a positioning convex step 32-2 of the tooth-side fastener, and the positioning convex step 32-2 is ferromagnetic. The tooth-side connection mechanism 22 on the elastic retractor 2 is made of a magnetic material, and the tooth-side connection mechanism 22 on the elastic retractor 2 and the elastic-retractor tooth-side connection mechanism 32 on the tooth-side fastener 3 form a pair of magnetic connection members that attract each other, thereby facilitating mounting and fixing. Moreover, a tongue-side positioning hole 22-1 on the elastic retractor 2 may also form concave-convex engagement with the positioning convex step 32-2 on the tooth-side fastener 3.

Referring to FIG. 30-1 and FIG. 30-2, the tooth-side fastener 3 includes a dental bone nail-type fixing support bracket 31-2, its elastic-retractor tooth-side connection mechanism 32 uses a positioning convex step 32-2 of the tooth-side fastener, and the tooth-side connection hole 22-1 on the elastic retractor 2 is sleeved on a groove formed between two positioning convex steps 32-2 to form a connection structure.

Referring to FIG. 31-1 and FIG. 32-2, the tooth-side fastener 3 includes a dental bone nail-type fixing support bracket 31-2, its elastic-retractor tooth-side connection mechanism 32 uses a positioning hook 32-3 of the tooth-side fastener, and the tooth-side connection hole 22-1 on the elastic retractor 2 is sleeved over the positioning hook 32-3 of the tooth-side fastener to form a connection structure.

Referring to FIG. 32-1 and FIG. 32-2, in this embodiment, the tooth-side fastener 3 includes a dental bone nail-type fixing support bracket 31-2, and its elastic-retractor tooth-side connection mechanism 32 uses a positioning concave groove 32-1 of the tooth-side fastener. The tooth-side connection mechanism 22 on the elastic retractor 2 uses a tooth-side connection convex step 22-2. The tooth-side connection convex step 22-2 is embedded in the positioning concave groove 32-1 of the tooth-side fastener, thereby forming a removable fixed connection.

It should be noted that, the structures disclosed and described in the present invention may be replaced by other structure with the same effect, and the embodiments described in the present invention are not intended to limit the present invention. Though the preferred embodiments of the present invention have been introduced and described in the specification, persons skilled in the art should know that these embodiments are merely described by way of example, and persons skilled in the art may make various changes, improvements, and replacements without departing from the present invention. Therefore, the protection scope of the present invention should be defined in accordance with the spirit and scope of the appended claims of the present invention.

What is claimed is:

1. An elastic tongue-dorsum retraction device, comprising:
   a tongue dorsum connection mechanism;
   an elastic retractor; and
   a tooth-side fastener,
   wherein:
      the tongue dorsum connection mechanism is an under-the-tongue-mucosa tunnel-type retraction connection mechanism or a connector adapted to be disposed at the tongue dorsum to prevent sagging of the tongue;
      the elastic retractor is made of a medical elastic material, the elastic retractor is a medical elastic film, an elastic strip-shaped object, an elastic wire object or a spring object that can stretch and produce a restoring force under the effect of an external force and can restore its original shape after the external force released, or an elastic mechanism comprising the elastic strip-shaped object, an elastic mechanism comprising the elastic wire object, or an elastic mechanism comprising the spring object;
      the tooth-side fastener comprises a support bracket capable of supporting the tooth-side fastener, an elastic-retractor tooth-side connection mechanism that can be connected to the elastic retractor, and a tooth-side fastening mechanism capable of fixing the tooth-side fastener to teeth, the alveolar bone, the maxilla, the mandible, or the maxilla and mandible; and the elastic-retractor tooth-side connection mechanism and the tooth-side fastening mechanism are disposed on the support bracket;
      the tooth-side fastener is configured to serve as a force-bearing fulcrum and is adapted to be fixed to teeth or the alveolar bone through the tooth-side fastening mechanism, or the tooth-side fastener is adapted to be removably fixed outside the maxilla lip, the mandible lip, or the maxilla and mandible lips through the tooth-side fastening mechanism; and one end of the elastic retractor is connected to the elastic-retractor tooth-side connection mechanism of the tooth-side fastener, and the other end of the elastic retractor is connected to the tongue dorsum connection mechanism; and
      at least one of the tooth-side connection mechanism and the tongue-side connection mechanism comprises a magnetic connection mechanism.

2. The elastic tongue-dorsum retraction device according to claim 1, wherein the tongue dorsum connection mechanism is adapted to be disposed in a tongue dorsum area that is in front of circumvallate papillae of the tongue and has a longitudinal length L of 0.1 cm to 5 cm, a transverse width W of 0.2 cm to 6 cm and a depth H of 0.1 cm to 1.0 cm along the oral cavity.

3. The elastic tongue-dorsum retraction device according to claim 1, wherein the elastic retractor forms an elastic retraction force of 15 g to 300 g between the tooth-side fastener and the tongue dorsum connection mechanism.

4. The elastic tongue-dorsum retraction device according to claim 1, wherein the under-the-tongue-mucosa tunnel-type retraction connection mechanism of the tongue dorsum connection mechanism is an implant that forms an under-the-tongue-mucosa epithelialized tunnel after the implant is removed, or is a thin-walled tube-shaped implant that forms an under-the-tongue-mucosa tunnel after the thin-walled tube-shaped implant is implanted.

5. The elastic tongue-dorsum retraction device according to claim 1, wherein the connector of the tongue dorsum connection mechanism is a fully-implantable connector that can be fully implanted under the tongue mucosa, a semi-implantable connector that is partially implanted under the tongue mucosa and partially exposed out of the tongue mucosa, or a mucosa-surface-fixed-type connector that can be fixed to the mucosa of the tongue dorsum.

6. The elastic tongue-dorsum retraction device according to claim 1, wherein the elastic retractor comprises a tongue-side connection mechanism that can be connected to the tongue dorsum connection mechanism.

7. The elastic tongue-dorsum retraction device according to claim 1, wherein the elastic retractor comprises a tooth-side connection mechanism that can be connected to the tooth-side fastener.

8. The elastic tongue-dorsum retraction device according to claim 1, wherein the elastic retractor is an elastic strip-shaped object, the elastic strip-shaped object is made of a medical silica gel film, a medical latex film, a medical polyurethane film, a medical rubber film or an elastic medical material braid, and the elastic strip-shaped object has a thickness of 0.01 mm to 3 mm.

9. The elastic tongue-dorsum retraction device according to claim 1, wherein the elastic retractor is a medical elastic wire object, the medical elastic wire object is made of medical silica gel, medical latex, medical polyurethane, medical rubber or an elastic medical material braid, and the medical elastic wire object has a diameter of 0.05 mm to 5 mm.

10. The elastic tongue-dorsum retraction device according to claim 1, wherein the elastic retractor comprises a tongue-side connection mechanism, an elastic deformation mechanism and a tooth-side connection mechanism; the tongue-side connection mechanism and the tooth-side connection mechanism are separately disposed at two ends of the elastic retractor, the tongue-side connection mechanism is provided with one tongue-side connection hole, and the tooth-side connection mechanism is provided with at least one tooth-side connection hole; and the elastic deformation mechanism is disposed between the tongue-side connection mechanism and the tooth-side connection mechanism.

11. The elastic tongue-dorsum retraction device according to claim 1, wherein the tongue dorsum connection mechanism and the elastic retractor can be integrally formed by using an integral manufacturing technology so as to form an integral-type elastic retraction mechanism, and the integral-type elastic retraction mechanism comprises the tongue dorsum connection mechanism and the elastic retractor.

12. The elastic tongue-dorsum retraction device according to claim 1, wherein the tooth-side connection mechanism on the elastic retractor is connected to the tooth-side fastener by magnetic connection.

13. The elastic tongue-dorsum retraction device according to claim 1, wherein the tongue-side connection mechanism on the elastic retractor is connected to the tongue dorsum connection mechanism by magnetic connection.

14. The elastic tongue-dorsum retraction device according to claim 1, wherein the support bracket of the tooth-side fastener is a tooth-side fixing support bracket adapted to be fixed to upper teeth or lower teeth, a dental bone nail-type fixing support bracket adapted to be fixed to the alveolar bone, a dental sleeve-type fixing support bracket adapted to be removably fit to upper teeth or lower teeth, or a support bracket adapted to be removably fixed outside the upper and lower lips.

15. The elastic tongue-dorsum retraction device according to claim 1, wherein the tooth-side fastener comprises a retraction-force adjustment mechanism capable of adjusting the magnitude of the retraction force of the elastic retractor.

16. The elastic tongue-dorsum retraction device according to claim 1, wherein the elastic retractor, the tongue dorsum connection mechanism or the tooth-side fastener is in a color matching that of human tissues.

* * * * *